(12) United States Patent
Andrews et al.

(10) Patent No.: US 10,806,774 B2
(45) Date of Patent: *Oct. 20, 2020

(54) MUTATED TRUNCATED VON WILLEBRAND FACTOR

(71) Applicant: CSL BEHRING LENGNAU AG, Lengnau (CH)

(72) Inventors: Arna Andrews, Kew East (AU); Con Panousis, Bundoora (AU); Kerstin Emmrich, Preston (AU); Michael Wilson, Elwood (AU); Steve Dower, Fitzroy North (AU); Matthew Hardy, Doreen (AU); Dallas Hartman, Niddrie (AU)

(73) Assignee: CSL BEHRING LENGNAU AG, Lengnau (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/068,181

(22) PCT Filed: Jan. 6, 2017

(86) PCT No.: PCT/AU2017/050010
§ 371 (c)(1),
(2) Date: Jul. 5, 2018

(87) PCT Pub. No.: WO2017/117631
PCT Pub. Date: Jul. 13, 2017

(65) Prior Publication Data
US 2019/0015483 A1    Jan. 17, 2019

(30) Foreign Application Priority Data

Jan. 7, 2016   (AU) .............................. 2016900034

(51) Int. Cl.

| A61K 38/37 | (2006.01) |
| A61K 31/718 | (2006.01) |
| A61K 31/727 | (2006.01) |
| A61K 31/728 | (2006.01) |
| A61K 47/10 | (2017.01) |
| A61P 7/04 | (2006.01) |
| C07K 14/755 | (2006.01) |
| C07K 16/46 | (2006.01) |
| C12N 15/62 | (2006.01) |
| A61K 38/00 | (2006.01) |
| A61K 35/00 | (2006.01) |

(52) U.S. Cl.
CPC .............. *A61K 38/37* (2013.01); *A61P 7/04* (2018.01); *C07K 14/755* (2013.01); *A61K 35/00* (2013.01); *A61K 38/00* (2013.01); *C07K 2319/31* (2013.01)

(58) Field of Classification Search
None
See application file for complete search history.

(56) References Cited

U.S. PATENT DOCUMENTS

| 4,399,216 A | 8/1983 | Axel et al. |
| 4,970,300 A | 11/1990 | Fulton et al. |
| 6,403,077 B1 | 6/2002 | Strom et al. |
| 8,575,104 B2 | 11/2013 | Weimer et al. |
| 2004/0087778 A1 | 5/2004 | Feige et al. |

FOREIGN PATENT DOCUMENTS

| EP | 0 117 058 A2 | 8/1984 |
| EP | 0 117 060 A2 | 8/1984 |
| EP | 0 503 991 A1 | 9/1992 |
| EP | 0 784 632 B1 | 1/1999 |
| WO | WO 94/15625 A1 | 7/1994 |
| WO | WO 97/03193 A1 | 1/1997 |
| WO | WO 97/11957 A1 | 4/1997 |
| WO | WO 97/40145 A1 | 10/1997 |
| WO | WO 99/55306 A1 | 11/1999 |
| WO | WO 02/060951 A2 | 8/2002 |
| WO | WO 02/103024 A2 | 12/2002 |
| WO | WO 03/076567 A2 | 9/2003 |
| WO | WO 03/087355 A1 | 10/2003 |
| WO | WO 03/093313 A2 | 11/2003 |
| WO | WO 2004/058800 A2 | 7/2004 |
| WO | WO 2004/067566 A1 | 8/2004 |
| WO | WO 2004/075923 A2 | 9/2004 |
| WO | WO 2004/101740 A2 | 11/2004 |
| WO | WO 2005/000892 A2 | 1/2005 |
| WO | WO 2005/001025 A2 | 1/2005 |
| WO | WO 2005/063808 A1 | 7/2005 |
| WO | WO 2006/000448 A2 | 1/2006 |

(Continued)

OTHER PUBLICATIONS

Amano et al., "Mutation at either Arg336 or Arg562 in Factor VIII is Insufficient for Complete Resistance to Activated Protein C (APC)-mediated Inactivation: Implications for the APC Resistance Test," Thromb. Haemost, 79: 557-563 (1998).

Ananyeva et al., "Catabolism of the Coagulation Factor VIII-Can We Prolong Lifetime of fVIII in Circulation," TCM, 11(6): 251-257 (2001).

Collins et al., "Molecular cloning of the human gene for von Willebrand factor and identification of the transcription initiation site," Proc. Natl. Acad. Sci. USA, 84: 4393-4397 (1987).

(Continued)

*Primary Examiner* — Marsha Tsay
(74) *Attorney, Agent, or Firm* — Finnegan, Henderson, Farabow, Garrett & Dunner, LLP

(57) ABSTRACT

The present invention provides a modified polypeptide which binds Factor VIII. The polypeptide comprises truncated von Willebrand Factor (VWF) which comprises a sequence as shown in SEQ ID NO:3 or a fragment thereof or a sequence 90% identical thereto, wherein the truncated VWF comprises at least one modification in comparison to SEQ ID NO: 3 in at least one position selected from the group consisting of S1, S3, L1 8, V42, S43, K149, N248, S279, V320, T325, Q395 and K418.

42 Claims, 5 Drawing Sheets

Specification includes a Sequence Listing.

(56) References Cited

FOREIGN PATENT DOCUMENTS

| | | |
|---|---|---|
| WO | WO 2006/053299 A2 | 5/2006 |
| WO | WO 2006/071801 A2 | 7/2006 |
| WO | WO 2006/108590 A1 | 10/2006 |
| WO | WO 2007/090584 A1 | 8/2007 |
| WO | WO 2007/126808 A1 | 11/2007 |
| WO | WO 2007/144173 A1 | 12/2007 |
| WO | WO 2008/077616 A1 | 7/2008 |
| WO | WO 2009/062100 A1 | 5/2009 |
| WO | WO 2009/156137 A1 | 12/2009 |
| WO | WO 2011/051489 A2 | 5/2011 |
| WO | WO 2011/060242 A2 | 5/2011 |
| WO | WO 2011/124718 A1 | 10/2011 |
| WO | WO 2012/059486 A1 | 5/2012 |
| WO | WO 2012/150319 A1 | 11/2012 |
| WO | WO 2013/083858 A1 | 6/2013 |
| WO | WO 2013/093760 A2 | 6/2013 |
| WO | WO 2013/106787 A1 | 7/2013 |
| WO | WO 2013/120939 A1 | 8/2013 |
| WO | WO 2013/135896 A1 | 9/2013 |
| WO | WO 2014/011819 A1 | 1/2014 |
| WO | WO 2014/072481 A1 | 5/2014 |
| WO | WO 2014/198699 A2 | 12/2014 |
| WO | WO 2015/185758 A2 | 12/2015 |
| WO | WO 2016/000039 A1 | 1/2016 |
| WO | WO 2017/117630 A9 | 7/2017 |

OTHER PUBLICATIONS

Dang et al., "Phylogenetic and Functional Analysis of Histidine Residues Essential for pH-dependent Multimerization of von Willebrand Factor," The Journal of Biological Chemistry, 286(29): 25763-25769 (2011).

Dumont et al., "Monomeric Fc Fusions—Impact on Pharmacokinetic and Biological Activity of Protein Therapeutics," Biodrugs, 20(3): 151-160 (2006).

Federici et al., "A sensitive ristocetin co-factor activity assay with recombinant glycoprotein Ibα for the diagnosis of patients with low von Willebrand factor levels," Haematologica, 89: 77-85 (2004).

Fischer et al., Structural analysis of recombinant von Willebrand factor: identification of hetero- and homo-dimers, FEBS Letters, 351:345-348 (1994).

Gale et al., "Intrinsic stability and functional properties of disulfide bond-stabilized coagulation factor VIIIa variants," Journal of Thrombosis and Haemostasis, 4: 1315-1322 (2006).

Gething et al., "Cell-surface expression of influenza haemagglutinin from a cloned DNA copy of the RNA gene," Nature, 293: 620-625 (1981).

Graham et al., "A New Technique for the Assay of Infectivity of Human Adenovirus 5 DNA," Virology, 52: 456-467 (1973).

Haberichter et al., "Structure and Function of von Willebrand Factor," Hemostasis and Thrombosis—Basic Principles and Clinical Practice (Sixth Edition), Chapter 13, 197-207 (2013).

Hawley-Nelson et al., "LipoefectAMINE™ Reagent: A New, Higher Efficiency Polycationic Liposome Transfection Reagent," Focus, 15(3): 73-79 (1993).

International search report and the written opinion of the international search authority, issued in International Patent Application No. PCT/AU2017/050010, dated Mar. 6, 2017, 6 pages.

Kallas et al., The von Willebrand factor collagen-binding activity assay: clinical application, Ann. Hematol., 80: 466-471 (2001).

Kaufman et al., "Effect of von Willebrand Factor Coexpression on the Synthesis and Secretion of Factor VIII in Chinese Hamster Ovary Cells," Molecular and Cellular Biology, 9(3): 1233-1242 (1989).

Keown et al., "Methods for Introducing DNA into Mammalian Cells," Methods in Enzymology, 185: 527-537 (1990).

Lavergne et al., "Primary Structure of the Factor VIII Binding Domain of Human, Porcine, and Rabbit von Willebrand Factor," Biochemical and Biophysical Research Communications, 194(3); 1019-1024 (1993).

Lee et al., "An Effect of Predilution on Potency Assays of Factor VIII Concentrates," Thrombosis Research, 30: 511-519 (1983).

Lollar et al., "Characterization of Factor VIII B-Cell Inhibitory Epitopes," Thrombosis and Haemostasis, 82(2): 505-508 (1999).

Mansour et al., "Disruption of the proto-oncogene int-2 in mouse embryo-derived stem cells: a general strategy for targeting mutations to non-selectable genes," Nature, 336(24): 348-352 (1988).

Mantei et al., "Rabbit β-globin mRNA production in mouse L cells transformed with cloned rabbit β-globin chromosomal DNA," Nature, 281: 40-46 (1979).

Mather et al., "Culture of Testicular Cells in Hormone-Supplemented Serum-Free Medium," Annals New York Academy of Sciences, 383:44-68 (1982).

Mather et al., "Establishment and Characterization of Two Distinct Mouse Testicular Epithelial Cell Lines," Biology of Reproduction, 23: 243-252 (1980).

Miao et al., "Bioengineering of coagulation factor VIII for improved secretion," Blood, 103: 3412-3419 (2004).

Oh et al., "Synthesis of recombinant blood coagulation factor VIII (FVIII) heavy and light chains and reconstitution of active form of FVIII," Experimental and Molecular Medicine, 31(2): 95-100 (1999).

Pipe, "Coagulation Factors with Improved Properties for Hemophilia Gene Therapy," Seminars in Thrombosis and Hemostasis, 30(2): 227-237 (2004).

Rizza, et al., "Coagulation Assay of VIIIC and IXC", The Hemophilias, 18-38 (1982).

Rosen, "Assay of Factor VIII:C with a Chromogenic Substrate," Scand. J. Haematol., 33(40): 139-145 (1984).

Schellenberger et al., "A recombinant polypeptide extends the in vivo half-life of peptides and proteins in a tunable matter," 27(12): 1186-1190 (2009).

Sucker et al., "Determination of von Willebrand Factor Activity: Evaluation of the HaemosIL™ Assay in Comparison With Established Procedures," Clinical and Applied Thrombosis/Hemostasis, 12(3): 305-310 (2006).

Swaroop et al., "Mutagenesis of a Potential Immunoglobulin-binding Protein-binding Site Enhances Secretion of Coagulation Factor VIII," The Journal of Biological Chemistry, 272(39): 24121-24124 (1997).

Urlaub et al., "Isolation of Chinese hamster cell mutants deficient in dihydrofolate reductase activity," Proc. Natl. Acad. Sci. USA, 77(7): 4216-4220 (1980).

Varki, "Mini Review—Diversity in the sialic acids," Glycobiology, 2(1): 25-40 (1992).

Varki, "Corrigendum Diversity in the sialic acids," Glycobiology, 2(2): 169 (1992).

Vlot et al., "The Affinity and Stoichiometry of Binding of Human Factor VIII to von Willebrand Factor," Blood, 85(11); 3150-3157 (1995).

Wakabayashi et al., "A Glu1 13Ala Mutation within a Factor VIII $CA^{2+}$-Binding Site Enhances Cofactor Interactions in Factor Xase," Biochemistry, 44: 10298-10304 (2005).

Zollner et al., "Preclinical efficacy and safety of rVIII-SingleChain (CSL627), a novel recombinant single-chain factor VIII," Thrombosis Research, 132: 280-287 (2013).

Lenting et al., "An experimental model to study the in vivo survival of von Willebrand factor. Basic aspects and application to the R1205H mutation," J. Biol. Chem., 2004, 279(13):12102-12109.

Yee et al., "A von Willebrand Factor Fragment Containing the D'D3 Domains is Sufficient to Stabilize Coagulation Factor VIII in Mice," Blood, 2014, 124:445-452.

Castro-Nunez et al., "Distinct Roles of Ser-764 and Lys-773 at the N Terminus of von Willebrand factor in Complex Assembly With Coagulation Factor VII," J. Bio. Chem., 2013, 288:393-400.

MUTATED TRUNCATED VON WILLEBRAND FACTOR

FILING DATA

This application is the United States national stage entry under 35 U.S.C. § 371 of International Application No. PCT/AU2017/050010, filed on Jan. 6, 2017 and published as WO 2017/117631 A1, which claims priority to Australian Patent Application No. 2016900034, filed on Jan. 7, 2016. The contents of these applications are each incorporated herein by reference in their entirety.

FIELD OF THE INVENTION

The present invention relates to polypeptides, in particular modified truncated von Willebrand Factor which exhibits improved binding affinity to Factor VIII. The invention further relates to a complex comprising the polypeptide and FVIII, to polynucleotides encoding the polypeptides of the invention and methods of producing the polypeptides. Furthermore, the invention concerns the therapeutic or prophylactic use of the polypeptide or complex of the invention for treating blood coagulation disorders.

BACKGROUND OF THE INVENTION

There are various bleeding disorders caused by deficiencies of blood coagulation factors. The most common disorders are hemophilia A and B, resulting from deficiencies of blood coagulation factor VIII and IX, respectively. Another known bleeding disorder is von Willebrand's disease.

In plasma FVIII exists predominantly in a noncovalent complex with VWF and acts as a cofactor for activated factor IX in the membrane bound activated factor X generating complex.

Several attempts have been made to prolong the half-life of non-activated FVIII either by reducing its interaction with cellular receptors (WO 03/093313A2, WO 02/060951A2), by covalently attaching polymers to FVIII (WO 94/15625, WO 97/11957 and U.S. Pat. No. 4,970,300), by encapsulation of FVIII (WO 99/55306), by introduction of novel metal binding sites (WO 97/03193), by covalently attaching the A2 domain to the A3 domain either by peptidic (WO 97/40145 and WO 03/087355) or disulfide linkage (WO 02/103024A2) or by covalently attaching the A1 domain to the A2 domain (WO2006/108590).

Another approach to enhance the functional half-life of FVIII or VWF is by PEGylation of FVIII (WO 2007/126808, WO 2006/053299, WO 2004/075923). PEGylation of VWF (WO 2006/071801) has also been attempted in an effort to indirectly enhance the half-life of FVIII present in plasma. Also fusion proteins of FVIII have been described (WO 2004/101740, WO2008/077616 and WO 2009/156137).

VWF, which is missing, functionally defective or only available in reduced quantity in different forms of von Willebrand disease (VWD), is a multimeric adhesive glycoprotein present in plasma, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc Natl. Acad. Sci. USA 84:4393-4397. The precursor polypeptide, pre-pro-VWF, consists of a 22-residue signal peptide, a 741-residue pro-peptide and the 2050-residue polypeptide found in plasma (Fischer et al., FEBS Lett. 351: 345-348, 1994). After cleavage of the signal peptide in the endoplasmic reticulum a C-terminal disulfide bridge is formed between two monomers of VWF. During further transport through the secretory pathway 12 N-linked and 10 O-linked carbohydrate side chains are added. Importantly, VWF dimers are multimerized via N-terminal disulfide bridges and the propeptide of 741 amino acids is cleaved off by the enzyme PACE/furin in the late Golgi apparatus. The propeptide as well as the high-molecular-weight multimers of VWF (VWF-HMWM) are stored in the Weibel-Pallade bodies of endothelial cells or in the α-Granules of platelets.

Once secreted into plasma the protease ADAMTS13 cleaves VWF within the A1 domain of VWF. Plasma VWF consists of a range of multimers ranging from single dimers of 500 kDa to multimers consisting of more than 20 dimers of a molecular weight of over 10,000 kDa. Typically VWF high molecular weight multimers (VWF-HMWM) have the strongest hemostatic activity, which can be measured in ristocetin cofactor activity (VWF:RCo). The higher the ratio of VWF:RCo/VWF antigen, the higher the relative amount of high molecular weight multimers.

Defects in VWF are causal to von Willebrand disease (VWD), which is characterized by a more or less pronounced bleeding phenotype. VWD type 3 is the most severe form in which VWF is completely missing, VWD type 1 relates to a quantitative loss of VWF and its phenotype can be very mild. VWD type 2 relates to qualitative defects of VWF and can be as severe as VWD type 3. VWD type 2 has many sub forms some of them being associated with the loss or the decrease of high molecular weight multimers. Von VWD type 2a is characterized by a loss of both intermediate and large multimers. VWD type 2B is characterized by a loss of highest-molecular-weight multimers.

VWD is the most frequent inherited bleeding disorder in humans and can be treated by replacement therapy with concentrates containing VWF of plasma or recombinant origin. VWF can be prepared from human plasma as for example described in EP 05503991. EP 0784632 describes a method for producing and isolating recombinant VWF.

In plasma FVIII binds with high affinity to VWF, which protects it from premature catabolism and thus, plays in addition to its role in primary hemostasis, a crucial role in regulation of plasma levels of FVIII and as a consequence is also a central factor in the control of secondary hemostasis. The half-life of non-activated FVIII bound to VWF is about 12 to 14 hours in plasma. In von Willebrand disease type 3, where no or almost no VWF is present, the half-life of FVIII is only about 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al. 1989, Mol Cell Biol).

SUMMARY OF THE INVENTION

In the current applicant's co-pending International Patent Application no. PCT/AU2015/050369 it is disclosed that a number of modifications in domain D' of VWF can increase binding to Factor VIII. The disclosure of this application is included herein by cross-reference. The present inventors have now found that the binding of VWF to Factor VIII can be increased by other modifications in D' and in particular by modifications in the D3 domain.

The present invention therefore relates to the following embodiments [1] to [93]:

[1] A polypeptide comprising truncated von Willebrand Factor (VWF) which comprises a sequence as shown in SEQ ID NO:3 or a fragment thereof or a sequence 90% identical thereto, wherein the truncated VWF comprises at least one modification in comparison to SEQ ID NO:3 in at least one position selected from the group consisting of 51, S3, L18, V42, S43, K149, N248, S279, V320, T325, Q395 and K418; and wherein the truncated VWF binds Factor VIII (FVIII).

[2] The polypeptide as in item 1 in which the truncated VWF comprises a sequence as shown in SEQ ID NO:3, wherein the truncated VWF comprises at least one modification in comparison to SEQ ID NO:3 in at least one position selected from the group consisting of 51, S3, L18, V42, S43, K149, N248, S279, V320, T325, Q395 and K418; and wherein the truncated VWF binds Factor VIII (FVIII).

[3] The polypeptide as in item 1 or item 2 in which the truncated VWF binds to Factor VIII with an off rate lower than a reference polypeptide comprising an unmodified SEQ ID NO:3.

[4] The polypeptide as in item 3 in which the modified polypeptide binds to Factor VIII with an off rate at least 5 fold lower than the reference polypeptide.

[5] The polypeptide as in item 3 in which the modified polypeptide binds to Factor VIII with an off rate at least 10 fold lower than the reference polypeptide.

[6] The polypeptide as in item 3 in which the modified polypeptide binds to Factor VIII with a KD at least 5 fold lower than the reference polypeptide.

[7] The polypeptide as in item 6 in which the modified polypeptide binds to Factor VIII with an off rate at least 10 fold lower than the reference polypeptide.

[8] The polypeptide as in any one of items 1 to 7 in which the truncated VWF comprises at least two modifications.

[9] The polypeptide as in any one of items 1 to 8 in which the truncated VWF comprises at least three modifications.

[10] The polypeptide as in any one of items 1 to 9 in which the truncated VWF comprises SEQ ID NO:5 (S764P/S766W/V1083A).

[11] The polypeptide as in any one of items 1 to 9 in which the truncated VWF comprises SEQ ID NO:6 (S764G/S766Y/V1083A).

[12] The polypeptide as in any one of items 1 to 9 in which the truncated VWF comprises SEQ ID NO:7 (S764E/S766Y/V1083A).

[13] The polypeptide as in any one of items 1 to 9 in which the truncated VWF comprises SEQ ID NO:8 (N1011S/V1083A/K1181E).

[14] The polypeptide as in any one of items 1 to 8 in which the truncated VWF comprises SEQ ID NO:17 (S766Y/V1083A).

[15] The polypeptide as in any one of items 1 to 7 in which the truncated VWF comprises SEQ ID NO:9 (V1083A).

[16] The polypeptide as in any one of items 1 to 7 in which the truncated VWF comprises SEQ ID NO:10 (S1042T).

[17] The polypeptide as in any one of items 1 to 8 in which the truncated VWF comprises SEQ ID NO:11 (V805A/Q1158L).

[18] The polypeptide as in any one of items 1 to 8 in which the truncated VWF comprises SEQ ID NO:12 (K912E/T1088S).

[19] The polypeptide as in any one of items 1 to 7 in which the truncated VWF comprises SEQ ID NO:13 (L781P).

[20] The polypeptide as in any one of items 1 to 19 in which the truncated VWF further comprises residues 1243 to 1247 of SEQ ID NO:2.

[21] The polypeptide as in any one of items 1 to 20 in which the truncated VWF further comprises residues 1243 to 1270 of SEQ ID NO:2.

[22] The polypeptide as in any one of items 1 to 19 in which the truncated VWF lacks residues 1243 to 1247 of SEQ ID NO:2.

[23] The polypeptide as in item 22 in which the truncated VWF lacks residues 1243 to 2813 of SEQ ID NO:2.

[24] The polypeptide as in item 22 or item 23 in which SEQ ID NO:3 is modified such that the residue at position 1 is selected from the group consisting of G, P, V, E, Y, A and L.

[25] The polypeptide as in any one of items 22 to 24 in which SEQ ID NO:3 is modified such that the residue at position 3 is selected from the group consisting of Y, I, M, V, F, H, R and W.

[26] The polypeptide as in any one of items 22 to 24 in which the truncated VWF comprises SEQ ID NO:18 (S764G/S766Y).

[27] The polypeptide as in any one of items 22 to 24 in which the truncated VWF comprises SEQ ID NO:19 (5764P/57661).

[28] The polypeptide as in any one of items 22 to 24 in which the truncated VWF comprises SEQ ID NO:20 (S764P/S766M).

[29] The polypeptide as in any one of items 22 to 24 in which the truncated VWF comprises SEQ ID NO:21 (S764V/S766Y).

[30] The polypeptide as in any one of items 22 to 24 in which the truncated VWF comprises SEQ ID NO:22 (S764E/S766Y).

[31] The polypeptide as in any one of items 22 to 24 in which the truncated VWF comprises SEQ ID NO:23 (S764Y/S766Y).

[32] The polypeptide as in any one of items 22 to 24 in which the truncated VWF comprises SEQ ID NO:24 (S764L/S766Y).

[33] The polypeptide as in any one of items 22 to 24 in which the truncated VWF comprises SEQ ID NO:25 (S764P/S766W).

[34] The polypeptide as in any one of items 22 to 24 in which the truncated VWF comprises SEQ ID NO:26 (S766W/S806A).

[35] The polypeptide as in any one of items 22 to 24 in which the truncated VWF comprises SEQ ID NO:27 (S766Y/P769K).

[36] The polypeptide as in any one of items 22 to 24 in which the truncated VWF comprises SEQ ID NO:28 (S766Y/P769N).

[37] The polypeptide as in any one of items 22 to 24 in which the truncated VWF comprises SEQ ID NO:29 (S766Y/P769R).

[38] The polypeptide as in any one of items 22 to 24 in which the truncated VWF comprises SEQ ID NO:30 (S764P/S766L).

[39] A polypeptide which binds Factor VIII wherein the truncated VWF comprises a sequence as shown in SEQ ID NO:3, or a fragment thereof, in which the sequence comprises a modification in at least position 320 and at positions 1 and/or 3 such that the truncated VWF binds to Factor VIII with an off rate lower than a reference polypeptide comprising an unmodified SEQ ID NO:3.

[40] The polypeptide as in 38 in which the truncated VWF comprises modifications in at least positions 1, 3 and 320 of SEQ ID NO:3.

[41] The polypeptide as in item 38 or 39 in which SEQ ID NO:3 is modified such that the residue at position 320 is A.

[42] The polypeptide as in any one of items 38 to 40 in which SEQ ID NO:3 is modified such that the residue at position 3 is selected from the group consisting of Y, I, M, V, F, H, R and W.

[43] The polypeptide as in any one of items 38 to 41 in which SEQ ID NO:3 is modified such that the residue at position 1 is selected from the group consisting of G, P, V, E, Y, A and L.

[44] The polypeptide as in any one of items 38 to 42 in which the truncated VWF further comprises residues 1243 to 1247 of SEQ ID NO:2.

[45] The polypeptide as in any one of items 38 to 43 in which the truncated VWF further comprises residues 1243 to 1270 of SEQ ID NO:2.

[46] The polypeptide as in any one of items 38 to 43 in which the truncated VWF lacks residues 1243 to 2813 of SEQ ID NO:2.

[47] The polypeptide as in any one of items 1 to 46 in which the polypeptide further comprises a half-life extending moiety.

[48] The polypeptide as in claim 47 wherein the half-life extending moiety is a heterologous amino acid sequence fused to the truncated VWF.

[49] The polypeptide as in item 48, wherein said heterologous amino acid sequence comprises or consists of a polypeptide selected from the group consisting of immunoglobulin constant regions and portions thereof, e.g. the Fc fragment, transferrin and fragments thereof, the C-terminal peptide of human chorionic gonadotropin, solvated random chains with large hydrodynamic volume known as XTEN, homo-amino acid repeats (HAP), proline-alanine-serine repeats (PAS), albumin, afamin, alpha-fetoprotein, Vitamin D binding protein, polypeptides capable of binding under physiological conditions to albumin or immunoglobulin constant regions, and combinations thereof

[50] The polypeptide as in any one of items 47 to 49, wherein the half-life extending moiety is conjugated to the polypeptide.

[51] The polypeptide as in item 50 wherein said half-life-extending moiety is selected from the group consisting of hydroxyethyl starch (HES), polyethylene glycol (PEG), polysialic acids (PSAs), elastin-like polypeptides, heparosan polymers, hyaluronic acid and albumin binding ligands, e.g. fatty acid chains, and combinations thereof.

[52] The polypeptide as in item 49 in which the heterologous amino acid sequence comprises albumin.

[53] The polypeptide as in item 52 in which the N-terminus of the albumin is fused to the C-terminus of the modified polypeptide sequence either directly or via a spacer.

[54] The polypeptide as in item 53 in which 1 to 5 amino acids at the natural C-terminus of the polypeptide have been deleted.

[55] The polypeptide as in one of items 1 to 54 wherein the polypeptide is a glycoprotein comprising N-glycans, and wherein at least 75%, preferably at least 85%, preferably at least 90%, and more preferably at least 95% of said N-glycans comprise, on average, at least one sialic acid moiety.

[56] The polypeptide of item 55 wherein at least 60% of said N-glycans comprise, on average, at least one α-2,6-sialic acid moiety.

[57] The polypeptide as in any one of items 1 to 55 wherein the polypeptide is a dimer.

[58] A complex comprising a Factor VIII molecule and the polypeptide of any one of items 1 to 57.

[59] The polypeptide of any one of items 1 to 57 or the complex of item 58 for use in the treatment or prophylaxis of a blood coagulation disorder.

[60] The polypeptide or complex for use according to item 59 wherein the blood coagulation disorder is von Willebrand's disease (VWD) or hemophilia A.

[61] A pharmaceutical composition comprising the polypeptide of any one of items 1 to 57 or the complex of item 58

[62] A method of treating a blood coagulation disorder, comprising administering to a patient in need thereof, a pharmaceutically effective amount of the polypeptide of any one of items 1 to 57 or of the complex of item 58.

[63] The method of item 62 wherein the blood coagulation disorder is von Willebrand's disease (VWD) or hemophilia A.

[64] Use of the modified polypeptide of any one of items 1 to 57 or of the complex of item 58 in the preparation of a medicament for the treatment of a blood coagulation disorder.

[65] The use of item 64 wherein the blood coagulation disorder is von Willebrand's disease (VWD) or hemophilia A.

[66] A method of treatment of a blood coagulation disorder, said treatment comprising administering to a subject having endogenous VWF the polypeptide as in any one of items 1 to 57 and a Factor VIII (FVIII) wherein the molar ratio of the polypeptide to be administered to the FVIII to be administered is greater than 50.

[67] A method of treatment of a blood coagulation disorder, said treatment comprising administering to a subject having endogenous VWF the polypeptide as in any one of items 1 to 57 and a Factor VIII (FVIII) wherein the molar ratio of the polypeptide administered to the endogenous VWF is greater than 0.5.

[68] The method as in item 66 or 67 wherein the subject is a human.

[69] The method as in any one of items 66 to 68, wherein the polypeptide is administered intravenously.

[70] The method as in any one of items 66 to 69 wherein the mean residence time (MRT) of the FVIII is increased by the co-administration of the polypeptide as in any one of items 1 to 57, as compared to a reference treatment, wherein said reference treatment is identical to said treatment, except that the polypeptide and the FVIII are administered in equimolar amounts in said reference treatment.

[71] The method as in any one of items 66 to 70 wherein the frequency of administration of the FVIII is reduced as compared to a treatment with the FVIII alone.

[72] The method as in any one of items 66 to 71 wherein the plasma half-life of the polypeptide as in any one of items 1 to 57 is greater than that of endogenous VWF.

[73] The method as in item 73 wherein the plasma half-life of the polypeptide as in any one of items 1 to 57 is at least 25% greater than that of the endogeneous VWF.

[74] A pharmaceutical composition comprising (i) a FVIII and (ii) a polypeptide as in any one of items 1 to 57 wherein the molar ratio of the polypeptide to the FVIII in the composition is greater than 50.

[75] A pharmaceutical kit comprising (i) a FVIII and (ii) a polypeptide as defined in any one of items 1 to 57 for simultaneous, separate or sequential use in the treatment of a blood coagulation disorder, said treatment comprising administering to a subject having endogenous VWF the polypeptide and the FVIII, wherein the molar ratio of the polypeptide administered to the endogenous VWF is greater than 0.5, and/or wherein the molar ratio of the polypeptide to be administered to the FVIII to be administered is greater than 50.

[76] The use of a polypeptide as defined in any one of items 1 to 57 for improving the plasma half-life of FVIII, and/or for reducing the frequency of administration of FVIII.

[77] A method of treating a blood coagulation disorder, comprising administering to a patient having endogenous VWF an effective amount of a polypeptide as defined in any one of items 1 to 57 and a FVIII, wherein the molar ratio of the polypeptide administered to the endogenous VWF is greater than 0.5, and/or wherein the molar ratio of the polypeptide to be administered to the FVIII to be administered is greater than 50.

[78] A polynucleotide encoding the polypeptide of any one of items 1 to 57.

[79] A plasmid or vector comprising the polynucleotide of item 78.

[80] The plasmid or vector of item 79 said plasmid or vector being an expression vector.

[81] A host cell comprising the polynucleotide of item 78 or the plasmid of item 79 or 80.

[82] A method of producing a polypeptide comprising a truncated VWF, comprising:
  (i) culturing the host cells of item 81 under conditions such that the polypeptide comprising a truncated VWF is expressed; and
  (ii) optionally recovering the polypeptide comprising the truncated VWF from the host cells or from the culture medium.

[83] A method of increasing the half-life of Factor VIII the method comprising mixing the Factor VIII with the polypeptide as in any one of items 1 to 57.

[84] A method of producing a polypeptide as in any one of items 1 to 57 comprising N-glycans with increased sialylation, which method comprises (i) providing cells comprising a nucleic acid encoding the polypeptide as in any one of items 1 to 57, and (ii) culturing said cells at a temperature of less than 36.0° C.

[85] A method of producing a dimer of a polypeptide as in any one of items 1 to 57, or for increasing the dimerization of said polypeptide, which method comprises (i) providing cells comprising a nucleic acid encoding the amino acid sequence of the polypeptide as in any one of items 1 to 57, and (ii) culturing said cells at a temperature of less than 36.0° C.

[86] The method as in item 84 or 85 wherein the cells further comprise a recombinant nucleic acid encoding a sialyltransferase, preferably an α-2,6-sialyltransferase or an α-2,3-sialyltransferase.

[87] The method of any one of items 84 to 86 wherein prior to step (ii) the cells are cultured at a temperature of 37.0° C.±1.0° C., and step (ii) comprises culturing the cells at a temperature of 34.0° C.±2.0° C.

[88] The method of any one of 84 to 87 further comprising (i) subjecting the polypeptide obtained in any one of items 84 to 87 to ion exchange chromatography, whereby polypeptide with high sialylation is separated from polypeptide with low sialylation; and collecting the fractions eluted from the ion exchange column having high sialylation; or (ii) contacting the polypeptide obtained in any one of items 84 to 87 with a sialyltransferase and a sialic acid donor in vitro.

[89] The method of any one of items 84 to 88 wherein, on average, at least 75% of the N-glycans of the obtained polypeptide comprise at least one sialic acid moiety.

[90] The method of any one of items 84 to 89 wherein, on average, at least 50% of the obtained polypeptide is present as dimer.

[91] A polypeptide obtainable by a method of any one of items 84 to 90.

[92] The polypeptide as in item 91 for use in the treatment of a blood coagulation disorder, said treatment comprising administering to a subject an effective amount of said polypeptide and an effective amount of a FVIII, wherein the polypeptide is administered intravenously or subcutaneously, and the FVIII is administered intravenously.

[93] The polypeptide for use according to item 91, wherein the mean residence time (MRT) of the FVIII is increased by the co-administration of the polypeptide, as compared to a treatment with the FVIII alone; and/or wherein the frequency of administration of the FVIII is reduced as compared to a treatment with the FVIII alone.

DETAILED DESCRIPTION

Figure 1:
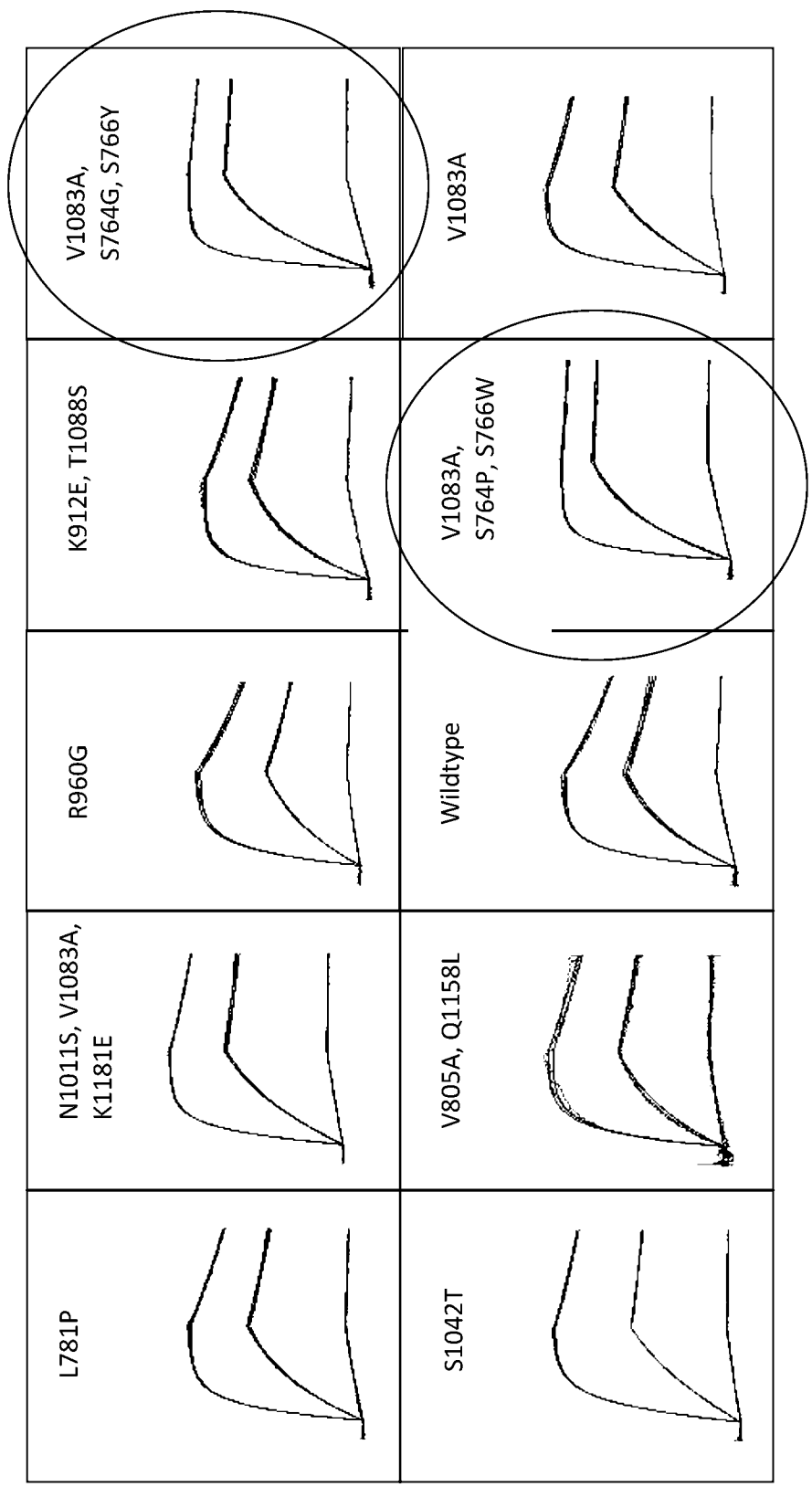
FIG. 1: Sample sensorgrams from the screen at neutral pH. The two candidates with strongest affinity and slowest off rate are circled.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

All publications mentioned in this specification are herein incorporated by reference in their entirety.

It must be noted that, as used in the subject specification, the singular forms "a", "an" and "the" include plural aspects unless the context clearly dictates otherwise. Thus, for example, reference to "an agent" includes a single agent, as well as two or more agents; reference to "a molecule" includes a single molecule, as well as two or more molecules; and so forth.

Truncated VWF

The term "von Willebrand Factor" or "VWF", as used herein, refers to any polypeptide having a biological activity of wild type VWF, in particular the ability to bind Factor VIII. The gene encoding wild type VWF is transcribed into a 9 kb mRNA which is translated into a pre-propolypeptide of 2813 amino acids with an estimated molecular weight of 310,000 Da. The pre-propolypeptide contains a 22 amino acids signal peptide, a 741 amino acid pro-polypeptide and the mature subunit. Cleavage of the 741 amino acids propolypeptide from the N-terminus results in mature VWF consisting of 2050 amino acids. The amino acid sequence of the VWF pre-propolypeptide is shown in SEQ ID NO:2. Unless indicated otherwise, the amino acid numbering of VWF residues in this application refers to SEQ ID NO:2, even if the VWF molecule does not need to comprise all residues of SEQ ID NO:2. The amino acid sequence of mature VWF is shown in SEQ ID NO:4. The term "VWF" as used herein refers to the mature form of VWF unless indicated otherwise.

The propolypeptide of wild type VWF comprises multiple domains which are arranged in the following order:

D1-D2-D'-D3-A1-A2-A3-D4-B1-B2-B3-C1-C2-CK

The D1 and D2 domain represent the propeptide which is cleaved off to yield the mature VWF. The D'-D3 domains encompass amino acids responsible for binding to Factor VIII. The amino acid sequence of at least a portion of D'-D3 domains of wild type VWF is shown in SEQ ID NO:3. The carboxy terminal 90 residues comprise the "CK" domain that is homologous to the "cysteine knot" superfamily of protein. These family members have a tendency to dimerise through disulfide bonds.

Preferably, wild type VWF comprises the amino acid sequence of mature VWF as shown in SEQ ID NO:4. Also encompassed are additions, insertions, N-terminal, C-terminal or internal deletions of VWF as long as a biological activity of VWF, in particular the ability to bind FVIII, is retained. The biological activity is retained in the sense of the invention if the VWF with deletions retains at least 10%, preferably at least 25%, more preferably at least 50%, most preferably at least 75% of the biological activity of wild-type VWF. The biological activity of wild-type VWF can be determined by the artisan using methods for ristocetin co-factor activity (Federici A B et al. 2004. Haematologica 89:77-85), binding of VWF to GP Ibα of the platelet glycoprotein complex Ib-V-IX (Sucker et al. 2006. Clin Appl Thromb Hemost. 12:305-310), or a collagen binding assay (Kailas & Talpsep. 2001. Annals of Hematology 80:466-471). Where the biological activity of VWF is the ability to bind FVIII this can be measured in a number of ways, however, it is preferably measured as described in Example 1 herein.

Factor VIII

The terms "blood coagulation Factor VIII", "Factor VIII" and "FVIII" are used interchangeably herein. "Blood coagulation Factor VIII" includes wild-type blood coagulation FVIII as well as derivatives of wild-type blood coagulation FVIII having the procoagulant activity of wild-type blood coagulation FVIII. Derivatives may have deletions, insertions and/or additions compared with the amino acid sequence of wild-type FVIII. The term FVIII includes proteolytically processed forms of FVIII, e.g. the form before activation, comprising heavy chain and light chain. Included are plasma derived and recombinant FVIII including B domain deleted FVIII. Examples of Commercial products include Advate®, Kogenate®, Xyntha®, Loctate® and Novoeight®.

The term "FVIII" includes any FVIII variants or mutants having at least 25%, more preferably at least 50%, most preferably at least 75% of the biological activity of wild-type factor VIII.

As non-limiting examples, FVIII molecules include FVIII mutants preventing or reducing APC cleavage (Amano 1998. Thromb. Haemost. 79:557-563), FVIII mutants further stabilizing the A2 domain (WO 97/40145), FVIII mutants having increased expression (Swaroop et al. 1997. JBC 272:24121-24124), FVIII mutants having reduced immunogenicity (Lollar 1999. Thromb. Haemost. 82:505-508), FVIII reconstituted from differently expressed heavy and light chains (Oh et al. 1999. Exp. Mol. Med. 31:95-100), FVIII mutants having reduced binding to receptors leading to catabolism of FVIII like HSPG (heparan sulfate proteoglycans) and/or LRP (low density lipoprotein receptor related protein) (Ananyeva et al. 2001. TCM, 11:251-257), disulfide bond-stabilized FVIII variants (Gale et al., 2006. J. Thromb. Hemost. 4:1315-1322), FVIII mutants with improved secretion properties (Miao et al., 2004. Blood 103:3412-3419), FVIII mutants with increased cofactor specific activity (Wakabayashi et al., 2005. Biochemistry 44:10298-304), FVIII mutants with improved biosynthesis and secretion, reduced ER chaperone interaction, improved ER-Golgi transport, increased activation or resistance to inactivation and improved half-life (summarized by Pipe 2004. Sem. Thromb. Hemost. 30:227-237). Another particularly preferred example is a recombinant form of FVIII as described in Zollner et al 2013, Thrombosis Research, 132:280-287. All of these FVIII mutants and variants are incorporated herein by reference in their entirety.

Preferably FVIII comprises the full length sequence of FVIII as shown in SEQ ID NO:14. Also encompassed are additions, insertions, substitutions, N-terminal, C-terminal or internal deletions of FVIII as long as the biological activity of FVIII is retained. The biological activity is retained in the sense of the invention if the FVIII with modifications retains at least 10%, preferably at least 25%, more preferably at least 50%, most preferably at least 75% of the biological activity of wild-type FVIII. The biological activity of FVIII can be determined by the artisan as described below.

A suitable test to determine the biological activity of FVIII is for example the one stage or the two stage coagulation assay (Rizza et al. 1982. Coagulation assay of FVIII:C and FIXa in Bloom ed. The Hemophilias. NY Churchhill Livingston 1992) or the chromogenic substrate FVIII:C assay (S. Rosen, 1984. Scand J Haematol 33: 139-145, suppl.). The content of these references is incorporated herein by reference.

The amino acid sequence of the mature wild-type form of human blood coagulation FVIII is shown in SEQ ID NO:14. The reference to an amino acid position of a specific sequence means the position of said amino acid in the FVIII wild-type protein and does not exclude the presence of mutations, e.g. deletions, insertions and/or substitutions at other positions in the sequence referred to. For example, a mutation in "Glu2004" referring to SEQ ID NO:14 does not exclude that in the modified homologue one or more amino acids at positions 1 through 2332 of SEQ ID NO:14 are missing.

"FVIII" and/or "VWF" within the above definition also include natural allelic variations that may exist and occur from one individual to another. "FVIII" and/or "VWF" within the above definition further includes variants of FVIII and/or VWF. Such variants differ in one or more amino acid residues from the wild-type sequence. Examples of such differences may include conservative amino acid substitutions, i.e. substitutions within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in Table 1.

TABLE 1

| (1) | Alanine | Glycine | | |
|---|---|---|---|---|
| (2) | Aspartic acid | Glutamic acid | | |
| (3) | Asparagine | Glutamine | Serine | Threonine |
| (4) | Arginine | Histidine | Lysine | |
| (5) | Isoleucine | Leucine | Methionine | Valine |
| (6) | Phenylalanine | Tyrosine | Tryptophan | |

The feature "truncated" means that the polypeptide does not comprise the entire amino acid sequence of mature VWF (amino acids 764-2813 of SEQ ID NO:2). Typically, the truncated VWF does not comprise all amino acids 764-2813 of SEQ ID NO:2 but only a fragment thereof. A truncated VWF may also be referred to as a VWF fragment, or in the plural as VWF fragments.

Typically, the truncated VWF is capable of binding to a Factor VIII. Preferably, the truncated VWF is capable of binding to the mature form of human native Factor VIII. In another embodiment, the truncated VWF is capable of binding to the single-chain Factor VIII consisting of the amino acid sequence SEQ ID NO:15.

The truncated VWF of the present invention preferably comprises or consists of (a) an amino acid sequence having a sequence identity of at least 90% to amino acids 764 to 1242 of SEQ ID NO:2, or (b) a fragment thereof, provided that the truncated VWF is still capable of binding to FVIII. More preferably, the truncated VWF consists of (a) an amino acid sequence having a sequence identity of at least 95%, at least 96%, at least 97%, at least 98%, or at least 99%, to amino acids 764 to 1242 of SEQ ID NO:2, or (b) a fragment thereof, provided that the truncated VWF is still capable of binding to FVIII. Most preferably, the truncated VWF consists of (a) amino acids 764 to 1242 of SEQ ID NO:2, or (b) a fragment thereof, provided that the truncated VWF is still capable of binding to FVIII.

As described in more detail below, the polypeptide may be prepared by a method which uses cells comprising a nucleic acid encoding the polypeptide comprising the truncated VWF. The nucleic acid is introduced into suitable host cells by techniques that are well known to those skilled in the art.

In a preferred embodiment, the nucleic acid in the host cell encodes (a) an amino acid sequence having a sequence identity of at least 90% to amino acids 1 to 1242 of SEQ ID NO:2, or (b) a fragment thereof, provided that the truncated mature VWF is still capable of binding to FVIII. More preferably, the nucleic acid encodes (a) an amino acid sequence having a sequence identity of at least 95%, at least 96%, at least 97%, at least 98%, or at least 99%, to amino acids 1 to 1242 of SEQ ID NO:2, or (b) a fragment thereof, provided that the truncated VWF is still capable of binding to FVIII. Most preferably, the nucleic acid encodes (a) amino acids 1 to 1242 of SEQ ID NO:2, or (b) a fragment thereof, provided that the truncated VWF is still capable of binding to FVIII. Especially if the polypeptide in accordance with this invention is a dimer, the nucleic acid will comprise a sequence encoding amino acids 1 to 763 of VWF (e.g. SEQ ID NO:2), even if the truncated VWF in the polypeptide does not comprise amino acids 1 to 763 of VWF (e.g. SEQ ID NO:2).

In other embodiments the truncated VWF comprises or consists of one of the following amino acid sequences, each referring to SEQ ID NO:2:
776-805; 766-805; 764-805; 776-810; 766-810; 764-810; 776-815; 766-815; 764-815; 776-820; 766-820; 764-820; 776-825; 766-825; 764-825; 776-830; 766-830; 764-830; 776-835; 766-835; 764-835; 776-840; 766-840; 764-840; 776-845; 766-845; 764-845; 76-850; 766-850; 764-850; 776-855; 766-855; 764-855; 776-860; 766-860; 764-860; 776-864; 766-864; 764-864; 776-865; 766-865; 764-865; 776-870; 766-870; 764-870; 776-875; 766-875; 764-875; 776-880; 766-880; 764-880; 776-885; 766-885; 764-885; 776-890; 766-890; 764-890; 776-895; 766-895; 764-895; 776-900; 766-900; 764-900; 776-905; 766-905; 764-905; 776-910; 766-910; 764-910; 776-915; 766-915; 764-915; 776-920; 766-920; 764-920; 776-925; 766-925; 764-925; 776-930; 766-930; 764-930; 776-935; 766-935; 764-935; 776-940; 766-940; 764-940; 776-945; 766-945; 764-945; 776-950; 766-950; 764-950; 776-955; 766-955; 764-955; 776-960; 766-960; 764-960; 776-965; 766-965; 764-965; 776-970; 766-970; 764-970; 776-975; 766-975; 764-975; 776-980; 766-980; 764-980; 776-985; 766-985; 764-985; 776-990; 766-990; 764-990; 776-995; 766-995; 764-995; 776-1000; 766-1000; 764-1000; 776-1005; 766-1005; 764-1005; 776-1010; 766-1010; 764-1010; 776-1015; 766-1015; 764-1015; 776-1020; 766-1020; 764-1020; 776-1025; 766-1025; 764-1025; 776-1030; 766-1030; 764-1030; 776-1035; 766-1035; 764-1035; 776-1040; 766-1040; 764-1040; 776-1045; 766-1045; 764-1045; 776-1050; 766-1050; 764-1050; 776-1055; 766-1055; 764-1055; 776-1060; 766-1060; 764-1060; 776-1065; 766-1065; 764-1065; 776-1070; 766-1070; 764-1070; 776-1075; 766-1075; 764-1075; 776-1080; 766-1080; 764-1080; 776-1085; 766-1085; 764-1085; 776-1090; 766-1090; 764-1090; 776-1095; 766-1095; 764-1095; 776-1100; 766-1100; 764-1100; 776-1105; 766-1105; 764-1105; 776-1110; 766-1110; 764-1110; 776-1115; 766-1115; 764-1115; 776-1120; 766-1120; 764-1120; 776-1125; 766-1125; 764-1125; 776-1130; 766-1130; 764-1130; 776-1135; 766-1135; 764-1135; 776-1140; 766-1140; 764-1140; 776-1145; 766-1145; 764-1145; 776-1150; 766-1150; 764-1150; 776-1155; 766-1155; 764-1155; 776-1160; 766-1160; 764-1160; 776-1165; 766-1165; 764-1165; 776-1170; 766-1170; 764-1170; 776-1175; 766-1175; 764-1175; 776-1180; 766-1180; 764-1180; 776-1185; 766-1185; 764-1185; 776-1190; 766-1190; 764-1190; 776-1195; 766-1195; 764-1195; 776-1200;

766-1200; 764-1200; 776-1205; 766-1205; 764-1205; 776-1210; 766-1210; 764-1210; 776-1215; 766-1215; 764-1215; 776-1220; 766-1220; 764-1220; 776-1225; 766-1225; 764-1225; 776-1230; 766-1230; 764-1230; 776-1235; 766-1235; 764-1235; 776-1240; 766-1240; 764-1240; 776-1242; 766-1242; 764-1242; 764-1247; 764-1464; 764-1250; 764-1041; 764-828; 764-865; 764-1045; 764-1035; 764-1128; 764-1198; 764-1268; 764-1270; 764-1261; 764-1264; 764-1459; 764-1463; 764-1464; 764-1683; 764-1873; 764-1482; 764-1479; 764-1672; and 764-1874.

In certain embodiments the truncated VWF has an internal deletion relative to mature wild type VWF. For example, the A1, A2, A3, D4, C1, C2, C3, C4, C5, C6 domains or combinations thereof may be deleted, and the D' domain, the D3 domain and the CK domain is retained. In further embodiments the truncated VWF does not comprise the binding sites for platelet glycoprotein Ibα (GPIbα), collagen and/or integrin αIIbβIII (RGDS sequence within the C1 domain). In other embodiments, the truncated VWF does not comprise the cleavage site (Tyr1605-Met1606) for ADAMTS13 which is located at the central A2 domain of VWF. In yet another embodiment, the truncated VWF does not comprise the binding sites for GPIbα, and/or does not comprise the binding site for collagen, and/or does not comprise the binding site for integrin αIIbβIII, and/or it does not comprise the cleavage site (Tyr1605-Met1606) for ADAMTS13 which is located at the central A2 domain of VWF.

In other embodiments the truncated VWF comprises or consists of an amino acid sequence that has a sequence identity of at least 90%, or at least 91%, or at least 92%, or at least 93%, or at least 94%, or at least 95%, or at least 96%, or at least 97%, or at least 98%, or at least 99%, to one of the amino acid sequences recited in the preceding paragraph, provided that the truncated VWF is capable of binding to FVIII.

A polypeptide of the invention is termed a "dimer" in the present invention if two monomers of polypeptide of the invention are linked covalently. Preferably the two monomeric subunits are covalently linked via at least one disulfide bridge, e.g. by one, two, three or four disulfide bridges. The cysteine residues forming the at least one disulfide bridge are preferably located within the truncated VWF portion of the polypeptide of the invention. In one embodiment, these cysteine residues are Cys-1099, Cys-1142, Cys-1222, Cys-1225, or Cys-1227 or combinations thereof.

If the polypeptide of the invention is a dimer, the truncated VWF preferably comprises or consists of two polypeptides each with an amino acid sequence having a sequence identity of at least 90% to amino acids 764 to 1099, amino acids 764 to 1142, amino acids 764 to 1222, amino acids 764 to 1225, amino acids 764 to 1227, amino acids 764 to 1242, amino acids 764 to 1247, or amino acids 764 to 1270 of SEQ ID NO:2 and is capable of binding to FVIII. In preferred embodiments the truncated VWF comprises or consists of an amino acid sequence having a sequence identity of at least 95%, at least 96%, at least 97%, at least 98%, or at least 99%, to amino acids 764 to 1099, amino acids 764 to 1142, amino acids 764 to 1222, amino acids 764 to 1225, or amino acids 764 to 1227 of SEQ ID NO:2 and is capable of binding to FVIII. Most preferably, the truncated VWF comprises or consists of amino acids 764 to 1099, amino acids 764 to 1142, amino acids 764 to 1222, amino acids 764 to 1225, amino acids 764 to 1227, amino acids 764 to 1242, amino acids 764 to 1247, or amino acids 764 to 1270 of SEQ ID NO:2.

The truncated VWF may be any one of the VWF fragments disclosed in WO 2013/106787, WO 2014/198699, WO 2011/060242, WO 2014/011819, WO 2013/083858, WO 2015/185758 or WO 2013/093760, the disclosures of which are incorporated herein by reference.

Half-Life Extending Moiety

In addition to the truncated VWF, the polypeptide of the invention may further comprise a half-life extending moiety. The half-life-extending moiety may be a heterologous amino acid sequence fused to the truncated VWF. Alternatively, the half-life-extending moiety may be chemically conjugated to the polypeptide comprising the truncated VWF by a covalent bond different from a peptide bond.

In certain embodiments of the invention, the half-life of the polypeptide of the invention is extended by chemical modification, e.g. attachment of a half-life extending moiety such as polyethylene glycol (PEGylation), glycosylated PEG, hydroxyl ethyl starch (HESylation), polysialic acids, elastin-like polypeptides, heparosan polymers or hyaluronic acid. In another embodiment, the polypeptide of the invention is conjugated to a HLEP such as albumin via a chemical linker. The principle of this conjugation technology has been described in an exemplary manner by Conjuchem LLC (see, e.g., U.S. Pat. No. 7,256,253).

Half-Life Enhancing Polypeptides (HLEPs)

Preferably, the half-life extending moiety is a half-life extending polypeptide (HLEP), more preferably HLEP is selected from albumin or fragments thereof, immunoglobulin constant region and portions thereof, e.g. the Fc fragment, solvated random chains with large hydrodynamic volume (e.g. XTEN (Schellenberger et al. 2009; Nature Biotechnol. 27:1186-1190), homo-amino acid repeats (HAP) or proline-alanine-serine repeats (PAS), afamin, alpha-fetoprotein, Vitamin D binding protein, transferrin or variants thereof, carboxyl-terminal peptide (CTP) of human chorionic gonadotropin-β subunit, polypeptides or lipids capable of binding under physiological conditions to albumin or immunoglobulin constant region.

A "half-life enhancing polypeptide" as used herein is preferably selected from the group consisting of albumin, a member of the albumin-family, the constant region of immunoglobulin G and fragments thereof, region and polypeptides capable of binding under physiological conditions to albumin, to members of the albumin family as well as to portions of an immunoglobulin constant region. It may be a full-length half-life-enhancing protein described herein (e.g. albumin, a member of the albumin-family or the constant region of immunoglobulin G) or one or more fragments thereof that are capable of stabilizing or prolonging the therapeutic activity or the biological activity of the coagulation factor. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to the respective polypeptide without the HLEP.

The HLEP portion of the polypeptide of the invention may be a variant of a wild type HLEP. The term "variants" includes insertions, deletions and substitutions, either conservative or non-conservative, where such changes do not substantially alter the FVIII-binding activity of the truncated VWF.

In particular, the proposed VWF HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

In one embodiment the polypeptide has the following structure:

tVWF-L1-H, [formula 1]

wherein tVWF is the truncated VWF, L1 is a chemical bond or a linker sequence, and H is a HLEP.

L1 may be a chemical bond or a linker sequence consisting of one or more amino acids, e.g. of 1 to 50, 1 to 30, 1 to 20, 1 to 15, 1 to 10, 1 to 5 or 1 to 3 (e.g. 1, 2 or 3) amino acids and which may be equal or different from each other. Usually, the linker sequences are not present at the corresponding position in the wild-type VWF. Examples of suitable amino acids present in L1 include Gly and Ser. The linker should be non-immunogenic and may be a non-cleavable or cleavable linker. Non-cleavable linkers may be comprised of alternating glycine and serine residues as exemplified in WO2007/090584. In another embodiment of the invention the peptidic linker between the truncated VWF moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584. Cleavable linker sequences are described, e.g., in WO 2013/120939 A1.

Preferred HLEP sequences are described infra. Likewise encompassed by the invention are fusions to the exact "N-terminal amino acid" or to the exact "C-terminal amino acid" of the respective HLEP, or fusions to the "N-terminal part" or "C-terminal part" of the respective HLEP, which includes N-terminal deletions of one or more amino acids of the HLEP. The polypeptide may comprise more than one HLEP sequence, e.g. two or three HLEP sequences. These multiple HLEP sequences may be fused to the C-terminal part of VWF in tandem, e.g. as successive repeats.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:16 herein or albumin from other vertebrates or fragments thereof, or analogs or variants of these molecules or fragments thereof.

In particular, the proposed polypeptides of the invention may include naturally and non-naturally occurring polymorphic variants of human albumin and fragments of human albumin. Generally speaking, an albumin fragment or variant will be at least 10, preferably at least 40, most preferably more than 70 amino acids long.

Preferred embodiments of the invention include albumin variants used as a HLEP of the polypeptide of the invention with enhanced binding to the FcRn receptor. Such albumin variants may lead to a longer plasma half-life of a truncated VWF albumin variant fusion protein as compared to a truncated VWF fusion with a wild-type albumin. Variants include those described in WO 2014072481, WO 2012150319, WO 2013135896, WO 2011124718, WO 2011051489 and WO 2012059486, the disclosures of which are incorporated by cross-reference.

The albumin portion of the polypeptides of the invention may comprise at least one subdomain or domain of HA or conservative modifications thereof.

Immunoglobulins as HLEPs

Immunoglobulin G (IgG) constant regions (Fc) are known in the art to increase the half-life of therapeutic proteins (Dumont J A et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic protein's in vivo half-lives. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life enhancing properties.

Various HLEPs which can be used in accordance with this invention are described in detail in WO 2013/120939 A1, the disclosure of which is included herein by cross-reference.

Linker Sequences

According to this invention, the therapeutic polypeptide moiety may be coupled to the HLEP moiety by a peptide linker. The linker should be non-immunogenic and may be a non-cleavable or cleavable linker.

Non-cleavable linkers may be comprised of alternating glycine and serine residues as exemplified in WO2007/090584.

In another embodiment of the invention the peptidic linker between the VWF moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584.

Cleavable linkers should be flexible enough to allow cleavage by proteases. In a preferred embodiment the cleavage of the linker proceeds comparably fast as the activation of FVIII within the fusion protein, if the fusion protein is a modified FVIII.

The cleavable linker preferably comprises a sequence derived from (a) the therapeutic polypeptide to be administered itself if it contains proteolytic cleavage sites that are proteolytically cleaved during activation of the therapeutic polypeptide, (b) a substrate polypeptide cleaved by a protease which is activated or formed by the involvement of the therapeutic polypeptide, or (c) a polypeptide involved in coagulation or fibrinolysis.

The linker region in a more preferred embodiment comprises a sequence of VWF, which should result in a decreased risk of neoantigenic properties of the expressed fusion protein.

The linker peptides are preferably cleavable by the proteases of the coagulation system, for example FIIa, FIXa, FXa, FXIa, FXIIa and FVIIa.

Exemplary combinations of therapeutic polypeptide, cleavable linker and HLEP include the constructs listed in WO2007/090584 (for example in table 2 and FIG. 4) and WO2007/144173 (for example in table 3a and 3b), but are not limited to these.

In another embodiment, the functional half-life of polypeptide of the invention or of FVIII complexed with the polypeptide of the invention is prolonged compared to that of wild type VWF or to that of FVIII complexed with wild type VWF, or with the reference polypeptide as defined supra. The increase may be more than 15%, for example at least 20% or at least 50%. Again, such functional half-life values can be measured in vitro in blood samples taken at different time intervals from said mammal after the modified VWF or the complex of FVIII with modified VWF has been administered.

In another embodiment of the invention, the polypeptide of the invention or FVIII complexed with the polypeptide of the invention exhibits an improved in vivo recovery compared to wild type VWF or to FVIII complexed with wild type VWF, or with the reference polypeptide defined supra. The in vivo recovery can be determined in vivo for example in normal animals or in animal models of hemophilia A, like FVIII knockout mice in which one would expect an increased percentage of FVIII be found by antigen or activity assays in the circulation shortly (5 to 10 min.) after i.v. administration compared to the corresponding wild-type VWF, or reference polypeptide defined supra.

The in vivo recovery is preferably increased by at least 10%, more preferably by at least 20%, and even more preferably by at least 40% compared to FVIII complexed with wild-type VWF, or with the reference polypeptide defined supra.

Ratios

As described in more detail below, the polypeptide of the invention may be a monomer, a dimer, or a mixture thereof. Any molar ratios according to the invention refer to a ratio of the molar concentration of the monomeric subunit of the polypeptide of the invention, whether actually present as monomer or dimer. Ratios are formed either over the molar concentration of the co-administered FVIII or over the molar concentration of the endogenous VWF subunits. Any ratios of polypeptide of the invention over FVIII in this application refer to the amount of polypeptide of the invention to be administered (in mole) divided by the amount of FVIII to be administered (in mole), unless indicated otherwise. The endogenous VWF is the VWF which is naturally present in the plasma of the animal or human being to be dosed with the polypeptide of the invention and with the co-administered FVIII. It usually consists of a range of different oligomers of approximately 2 to 40 monomeric subunits of VWF. Unless indicated otherwise, any ratios of polypeptide of the invention over endogenous VWF in this application refer to the molar plasma concentration of polypeptide of the invention per kg body weight of the treated subject immediately after administration of the polypeptide of the invention, divided by the molar plasma concentration of endogenous VWF per kg body weight of the treated subject. The molar plasma concentration of the polypeptide of the invention per kg body weight of the subject treated immediately after administration of the polypeptide of the invention is calculated assuming a dilution of the polypeptide of the invention administered directly after administration in a plasma volume of 40 ml/kg. The amount of the polypeptide of the invention immediately after administration when administered intravenously is assumed for the purposes of the invention to be identical to the amount administered.

Whilst the polypeptide of the present invention may be administered at any level an advantage may be achieved by administration at a level where the molar ratio of the polypeptide of the invention to the endogenous VWF is greater than 0.5. The concentration of endogenous VWF in the plasma of the subject to be treated can be determined by an ELISA or and activity assay, e.g. as described in the Examples. Typically, the concentration measured will be given in U/mL. This value can be converted into a molarity as described in the following.

Normal human plasma (NHP) contains VWF in a concentration of 1 U/mL or 100% by definition. This corresponds to a protein concentration of approximately 10 µg/mL (Haberichter S. L. and Montgomery R. R., Structure and function of von Willebrand factor; in: Hemostasis and Thrombosis, eds. Marder, Aird, Bennett, Schulman and White, Lippincott Williams & Wilkins 2013, pp 197-207). Based on this VWF concentration in NHP and a molecular weight of the mature VWF monomer of approximately 267,500 Da including 18-19% of glycosylation a molar plasma concentration of the VWF monomer unit of approximately 37×10-9 Mol/L can be calculated for NHP.

For calculation of the molar concentrations of rat or rabbit VWF subunits in normal rat or rabbit plasma, respectively, a molecular weight of the monomeric subunit comparable to human VWF was used (267,500 Da) together with an assumed comparable specific activity (100 U/mg) and the measured endogenous VWF activities in rat or rabbit plasma (refer also to examples).

The concentration of VWF in the human population varies from about 60% to about 200% of VWF concentration in NHP. In certain embodiments of the invention the concentration of endogenous VWF is defined as the concentration in NHP. In other embodiments the concentration of endogenous VWF is determined in the subject to be treated, and the dose of the polypeptide is based on this individual value.

The molar ratio of the polypeptide of the invention administered to the endogenous VWF is preferably at least 2, or at least 3, or at least 4, or at least 5, or at least 6, or at least 7, or at least 8, or at least 9, or at least 10, more preferably at least 15, or at least 20, or at least 25, or at least 30, most preferably at least 40, or at least 50, or at least 75.

The molar ratio of the polypeptide of the invention to be administered to the endogenous VWF may range from 0.5 to 1,000, or from 1 to 500, or from 2 to 400, or from 3 to 300, or from 4 to 250, or from 5 to 200, or from 6 to 150, or from 7 to 140, or from 8 to 130, or from 9 to 120, or from 10 to 110. Preferably, the molar ratio of the polypeptide of the invention administered to endogenous VWF ranges from 3 to 100, or from 4 to 90, or from 5 to 80, or from 6 to 75, or from 10 to 60.

The molar ratio of the polypeptide of the invention to be administered to FVIII to be administered is preferably at least 2, or at least 5, or at least 10, or at least 20, or at least 30, or at least 40, or at least 50, more preferably the ratio is greater than 50, or at least 75, at least 100, or greater than 100, or at least 200, most preferably at least 300, or at least 400, or at least 500.

The molar ratio of the polypeptide of the invention to be administered to FVIII to be administered may range from 2 to 10,000, or from 5 to 5,000, or from 10 to 4,000, or from 20 to 3,000, or from 30 to 2,000, or from 40 to 1,000. Preferably, the molar ratio of the polypeptide of the invention to be administered to FVIII to be administered ranges from 60 to 2,500, or from 110 to 2,000, or from 150 to 1,500, or from 200 to 1,000.

Table 1 summarizes various embodiments of the treatment in accordance with this invention. In a given embodiment, both requirements of column 2 and 3, respectively, must be fulfilled.

TABLE 1

| Embodiment # | Molar ratio polypeptide of the invention: endogenous VWF | Molar ratio polypeptide of the invention: FVIII administered |
|---|---|---|
| 1 | at least 1 | at least 2 |
| 2 | at least 1 | at least 5 |
| 3 | at least 1 | at least 10 |
| 4 | at least 1 | at least 40 |
| 5 | at least 1 | at least 50 |
| 6 | at least 1 | at least 80 |
| 7 | at least 1 | at least 100 |
| 6 | at least 1 | at least 150 |
| 7 | at least 1 | at least 250 |
| 8 | at least 1 | at least 400 |
| 9 | at least 1 | at least 800 |
| 10 | at least 1 | at least 1,000 |
| 11 | at least 3 | at least 2 |
| 12 | at least 3 | at least 5 |
| 13 | at least 3 | at least 10 |
| 14 | at least 3 | at least 40 |
| 15 | at least 3 | at least 50 |
| 16 | at least 3 | at least 80 |
| 17 | at least 3 | at least 100 |
| 18 | at least 3 | at least 150 |
| 19 | at least 3 | at least 250 |
| 20 | at least 3 | at least 400 |
| 21 | at least 3 | at least 800 |
| 22 | at least 3 | at least 1,000 |
| 23 | at least 5 | at least 2 |
| 24 | at least 5 | at least 5 |
| 25 | at least 5 | at least 10 |
| 26 | at least 5 | at least 40 |
| 27 | at least 5 | at least 50 |
| 28 | at least 5 | at least 80 |
| 29 | at least 5 | at least 100 |
| 30 | at least 5 | at least 150 |
| 31 | at least 5 | at least 250 |
| 32 | at least 5 | at least 400 |
| 33 | at least 5 | at least 800 |
| 34 | at least 5 | at least 1,000 |
| 35 | at least 10 | at least 2 |
| 36 | at least 10 | at least 5 |
| 37 | at least 10 | at least 10 |
| 38 | at least 10 | at least 40 |
| 39 | at least 10 | at least 50 |
| 40 | at least 10 | at least 80 |
| 41 | at least 10 | at least 100 |
| 42 | at least 10 | at least 150 |
| 43 | at least 10 | at least 250 |
| 44 | at least 10 | at least 400 |
| 45 | at least 10 | at least 800 |
| 46 | at least 10 | at least 1,000 |
| 47 | at least 20 | at least 2 |
| 48 | at least 20 | at least 5 |
| 49 | at least 20 | at least 10 |
| 50 | at least 20 | at least 40 |
| 51 | at least 20 | at least 50 |
| 52 | at least 20 | at least 80 |
| 53 | at least 20 | at least 100 |

TABLE 1-continued

| Embodiment # | Molar ratio polypeptide of the invention: endogenous VWF | Molar ratio polypeptide of the invention: FVIII administered |
|---|---|---|
| 54 | at least 20 | at least 150 |
| 55 | at least 20 | at least 250 |
| 56 | at least 20 | at least 400 |
| 57 | at least 20 | at least 800 |
| 58 | at least 20 | at least 1,000 |
| 59 | at least 50 | at least 2 |
| 60 | at least 50 | at least 5 |
| 61 | at least 50 | at least 10 |
| 62 | at least 50 | at least 40 |
| 63 | at least 50 | at least 50 |
| 64 | at least 50 | at least 80 |
| 65 | at least 50 | at least 100 |
| 66 | at least 50 | at least 150 |
| 67 | at least 50 | at least 250 |
| 68 | at least 50 | at least 400 |
| 69 | at least 50 | at least 800 |
| 70 | at least 50 | at least 1,000 |
| 71 | at least 50 | at least 2,000 |
| 72 | at least 50 | at least 4,000 |

Embodiments 1 to 72 shown in Table 1 can be combined with any other embodiment and aspect of the invention described herein. Further details of the treatment in accordance with the invention are described further below.

N-Glycans and Sialylation of the Polypeptide of the Invention

The polypeptide of the invention preferably comprises N-glycans, and at least 75%, preferably at least 85%, more preferably at least 90% of said N-glycans comprise, on average, at least one sialic acid moiety. In preferred embodiments, at least 91%, at least 92%, at least 93%, at least 94%, at least 95%, at least 96%, at least 97%, at least 98%, or at least 99%, of said N-glycans comprise, on average, at least one sialic acid moiety. The inventors found that polypeptides comprising highly sialylated VWF fragments not only have a prolonged half-life themselves, but are also capable to extend the half-life of co-administered FVIII. In other words, administration of the polypeptide of the invention leads to an extended half-life and/or to a reduced clearance of co-administered FVIII.

The polypeptide of the invention preferably comprises N-glycans, and at least 50% of the sialyl groups of the N-glycans of the glycoproteins are α-2,6-linked sialyl groups. In general, terminal sialyl groups can be attached to the galactose groups via a α-2,3- or via a α-2,6-linkage. Typically, N-glycans of the polypeptide of the invention comprise more α-2,6-linked sialyl groups than α-2,3-linked sialyl groups. Preferably, at least 60%, or at least 70%, or at least 80%, or at least 90% of the sialyl groups of the N-glycans are α-2,6-linked sialyl groups. These embodiments can be obtained by, e.g., co-expressing human α-2,6-sialyltransferase in mammalian cells.

In one embodiment, at least 85%, at least 90%, at least 95%, at least 96%, at least 97%, at least 98%, or at least 99%, of the N-glycans of the polypeptide of the invention comprise at least one sialic acid group. In another embodiment, at least 90%, at least 95%, at least 96%, at least 97%, at least 98%, or at least 99%, of the N-glycans of the polypeptide of the invention comprise at least one sialic acid group.

In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they are N-glycans lacking a sialic acid group. In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they do not have a sialic acid group.

The above-described embodiments can be combined with each other. Any percentages of N-glycans mentioned above, or any indications of the degree of sialylation, are to be understood as average percentages or degrees, i.e. they refer to a population of molecules, not to a single molecule. It is clear that the glycosylation or sialylation of the individual glycoprotein molecules within a population of glycoproteins will show some heterogeneity.

Dimers

It has further been found that the polypeptides of this invention may have a high proportion of dimers. The polypeptide of the invention is therefore preferably present as dimer. In one embodiment, at least 50%, or at least 60%, or at least 70% of the polypeptides are present as dimers. In another embodiment, the ratio dimer:monomer of the polypeptide of the invention is at least 1.5, preferably at least 2, more preferably at least 2.5 or at least 3. Most preferably all polypeptides of the invention are present as dimers. The use of dimers is favorable, as the dimer has an improved affinity to Factor VIII as compared to the monomer.

In one embodiment, the affinity of the polypeptide of the invention to Factor VIII is greater than that of human native VWF to the same Factor VIII molecule. The factor VIII affinity may refer to human native Factor VIII, or to the Factor VIII molecule characterized by SEQ ID NO:15.

It has been found that preparations of the polypeptide of this invention with a high proportion of dimers do have an increased affinity to Factor VIII. Such increased affinity to Factor VIII does lead to an enhanced stabilization of Factor VIII by the polypeptides of the present invention. Alternatively to or in combination with an increased dimer proportion also polypeptides in accordance with the invention with mutations within the Factor VIII binding domain which do increase the affinity to Factor VIII are preferred embodiments of the invention. Suitable mutations are disclosed, e.g., in WO 2013/120939 A1.

Preparation of the Polypeptide

The nucleic acid encoding the polypeptide of the invention can be prepared according to methods known in the art. Based on the cDNA sequence of VWF (SEQ ID NO:3), recombinant DNA encoding the above-mentioned truncated VWF constructs or polypeptides of the invention can be designed and generated.

Even if the polypeptide which is secreted by the host cells does not comprise amino acids 1 to 763 of VWF, it is preferred that the nucleic acid (e.g. the DNA) encoding the intracellular precursor of the polypeptide comprises a nucleotide sequence encoding an amino acid sequence having a sequence identity of at least 95%, at least 96%, at least 97%, at least 98%, or at least 99%, to amino acids 23 to 763 or preferably to amino acids 1 to 763 of SEQ ID NO:2. Most preferably, the nucleic acid (e.g. the DNA) encoding the intracellular precursor of the polypeptide comprises a nucleotide sequence encoding amino acids 23 to 763 of SEQ ID NO:2, or amino acids 1 to 763 of SEQ ID NO:2.

Constructs in which the DNA contains the entire open reading frame inserted in the correct orientation into an expression plasmid may be used for protein expression. Typical expression vectors contain promoters that direct the synthesis of large amounts of mRNA corresponding to the inserted nucleic acid in the plasmid-bearing cells. They may also include an origin of replication sequence allowing for their autonomous replication within the host organism, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Typically, the cells to be provided are obtained by introducing the nucleic acid encoding a polypeptide of the invention into mammalian host cells.

Any host cell susceptible to cell culture, and to expression of glycoproteins, may be utilized in accordance with the present invention. In certain embodiments, a host cell is mammalian. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243 251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (HepG2, HB 8065); mouse mammary tumor (MMT 060562, ATCC CCL51); TRI cells (Mather et al., Annals NY. Acad. Sci., 383:44-68, 1982); MRC 5 cells; PS4 cells; human amniocyte cells (CAP); and a human hepatoma line (Hep G2). Preferably, the cell line is a rodent cell line, especially a hamster cell line such as CHO or BHK.

Methods suitable for introducing nucleic acids sufficient to achieve expression of a glycoprotein of interest into mammalian host cells are known in the art. See, for example, Gething et al., Nature, 293:620-625, 1981; Mantei et al., Nature, 281:40-46, 1979; Levinson et al. EP 117,060; and EP 117,058. For mammalian cells, common methods of introducing genetic material into mammalian cells include the calcium phosphate precipitation method of Graham and van der Erb (Virology, 52:456-457, 1978) or the Lipofectamine™ (Gibco BRL) Method of Hawley-Nelson (Focus 15:73, 1993). General aspects of mammalian cell host system transformations have been described by Axel in U.S. Pat. No. 4,399,216. For various techniques for introducing genetic material into mammalian cells, see Keown et al., Methods in Enzymology, 1989, Keown et al., Methods in Enzymology, 185:527-537, 1990, and Mansour et al., Nature, 336:348-352, 1988.

The cells are cultured under conditions that allow expression of the polypeptide. The polypeptide can be recovered and purified using methods that are known to the skilled artisan.

Terminal Half-Life, MRT and Clearance

Another aspect of the invention is the use of a polypeptide as defined hereinabove for increasing the terminal half-life or mean residence time (MRT) or reducing the clearance of Factor VIII. For evaluation of the pharmacokinetic data a linear pharmacokinetics model (compound elimination via the central compartment) was applied. Accordingly, any pharmacokinetic parameters used herein are based on a linear pharmacokinetics model (compound elimination via the central compartment), unless indicated otherwise.

The "half-life" T½(t) at a certain time t is the time it takes to halve the plasma concentration C(t) that is present at time t, i.e. C [t+T½(t)]=C(t)/2. The "terminal half-life" is the limit of T½(t) when t tends to infinity.

The terminal half-life of administered FVIII is increased by at least 25%, preferably by at least 50%, more preferably by at least 75%, more preferably by at least 100%, most preferably by at least 150%, if an effective amount of the polypeptide of the present invention is co-administered, relative to administration of the FVIII alone. Another aspect of the invention is the use of a polypeptide as defined hereinabove for increasing the terminal half-life of Factor VIII.

The term "MRT", as used herein, means the average time a drug molecule (e.g. the polypeptide of the invention or a FVIII) resides in the body. In a linear pharmacokinetic system with constant clearance MRT can be calculated as the area under the first moment curve (AUMC) divided by the area under the plasma concentration-time curve (AUC). The first moment curve is time multiplied by plasma concentration at that time.

The MRT of administered FVIII is increased by at least 25%, preferably by at least 50%, more preferably by at least 75%, more preferably by at least 100%, most preferably by at least 150%, if an effective amount of the polypeptide of the present invention is co-administered, relative to administration of the FVIII alone. Another aspect of the invention is the use of a polypeptide as defined hereinabove for increasing the terminal half-life or mean residence time (MRT) or reducing the clearance of Factor VIII.

The term "clearance", as used herein, refers to the rate at which plasma is cleared of drug. Specifically, it is the current elimination rate of a drug divided by its current plasma concentration. In a linear pharmacokinetic system after a single intravenous administration the clearance can be calculated as the ratio of dose over the area under the plasma concentration-time curve (AUC), provided the clearance is constant. The lower the clearance the longer it takes until the plasma is cleared of the drug.

The clearance of administered FVIII is reduced by at least 10%, preferably by at least 25%, more preferably by at least 50%, more preferably by at least 60%, most preferably by at least 70%, if an effective amount of the polypeptide of the present invention is co-administered, relative to administration of the FVIII alone.

The invention further relates to a method of increasing the MRT or half-life, or to a method of reducing the clearance of Factor VIII in vivo, comprising administering to a subject an effective amount of a polypeptide as defined hereinabove.

A further aspect of this invention is a method of treating a blood coagulation disorder, comprising administering to a patient in need thereof an effective amount of a polypeptide as defined hereinabove.

A further aspect is the use of a polypeptide as defined hereinabove for reducing the frequency of administration of FVIII in a treatment of hemophilia A. The frequency of intravenous or subcutaneous administration of FVIII may be reduced to twice per week. Alternatively, the frequency of intravenous or subcutaneous administration of FVIII may be reduced to once per week, or even lower, e.g. to once per 10 days or once per 14 days. The FVIII may be administered twice weekly, every 5 days, once weekly, every 10 days, every two weeks, every three weeks, every four weeks or once a month, or in any range between any two of the foregoing values, for example from every four days to every month, from every 10 days to every two weeks, or from two to three times a week, etc.

Another aspect is the use of a polypeptide as defined hereinabove for reducing the dose of FVIII to be administered in a treatment of hemophilia A.

Treatment of Coagulation Disorder

The polypeptides of the invention are useful for treating coagulation disorders including hemophilia A. The term "hemophilia A" refers to a deficiency in functional coagulation FVIII, which is usually inherited.

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom a polypeptide of the invention is administered preferably is a human. In certain aspects, the human is a pediatric patient. In other aspects, the human is an adult patient.

Compositions comprising a polypeptide of the invention and, optionally FVIII, are described herein. The compositions typically are supplied as part of a sterile, pharmaceutical composition that includes a pharmaceutically acceptable carrier. This composition can be in any suitable form (depending upon the desired method of administering it to a patient).

The term "Factor VIII" and "FVIII" are used interchangeably herein and encompass both plasma derived FVIII and recombinant FVIII. Recombinant FVIII encompasses without limitation full-length FVIII as well as two-chain B-domain deleted or truncated variants as well as single-chain B-domain deleted or truncated variants for example those described in WO 2004/067566 and other FVIII variants with mutations outside the B-domain but having the biological activity of FVIII.

The polypeptide of the invention can be administered to a patient by a variety of routes such as orally, transdermally, subcutaneously, intranasally, intravenously, intraperitoneally, intramuscularly, topically or locally. The most suitable route for administration in any given case will depend on the particular polypeptide, the subject, and the nature and severity of the disease and the physical condition of the subject. Typically, a polypeptide of the invention will be administered intravenously.

The polypeptide and the FVIII are preferably administered intravenously or subcutaneously.

In a first embodiment, both the polypeptide and the FVIII are administered intravenously. In a second embodiment, both the polypeptide and the FVIII are administered subcutaneously.

In another embodiment, the FVIII is administered intravenously, and the polypeptide is administered via a different route. In further embodiments, the polypeptide is administered subcutaneously, and the FVIII is administered via a different route. For example, the polypeptide may be administered subcutaneously, and the FVIII may be administered intravenously.

In further embodiments, the FVIII is administered subcutaneously, and the polypeptide is administered via a different route. In further embodiments, the polypeptide is administered intravenously, and the FVIII is administered via a different route. For example, the polypeptide may be administered intravenously, and the FVIII may be administered subcutaneously.

Determination of the total number of doses, and length of treatment with a polypeptide of the invention is well within the capabilities of those skilled in the art. The dosage of the polypeptide of the invention to be administered depends on the concentrations of the FVIII to be administered, the concentration of endogenous VWF in the patient to be treated, or both. An effective dosage based on the ratios defined by the inventors of this application can be determined by the skilled person, taking into account the molecular weight of the polypeptide of the invention. Typical dosages for FVIII may range from about 20 U/kg body weight to about 100 U/kg body weight.

In accordance with this invention, the patient being treated with the polypeptide of the invention is also treated with blood coagulation Factor VIII. The polypeptide of the invention and the Factor VIII may be administered simultaneously or in a sequential fashion both modes of administration being encompassed by the term "combination therapy" and "co-administration". The polypeptide of the invention and the Factor VIII may be administered as a mixture, i.e. within the same composition, or separately, i.e. as separate compositions.

The concentration of Factor VIII in the composition used is typically in the range of 10-10,000 IU/mL. In different embodiments, the concentration of FVIII in the compositions of the invention is in the range of 10-8,000 IU/mL, or 10-5,000 IU/mL, or 20-3,000 IU/mL, or 50-1,500 IU/mL, or 3,000 IU/mL, or 2,500 IU/mL, or 2,000 IU/mL, or 1,500 IU/mL, or 1,200 IU/mL, or 1,000 IU/mL, or 800 IU/mL, or 750 IU/mL, or 600 IU/mL, or 500 IU/mL, or 400 IU/mL, or 300 IU/mL, or 250 IU/mL, or 200 IU/mL, or 150 IU/mL, or 125 IU/mL, or 100 IU/mL, or 62.5 IU/mL, or 50 IU/mL, provided the requirements regarding the ratio with respect to the VWF polypeptide of the invention as defined herein are fulfilled.

"International Unit," or "IU," is a unit of measurement of the blood coagulation activity (potency) of FVIII as measured by a FVIII activity assay such as a one stage clotting assay or a chromogenic substrate FVIII activity assay using a standard calibrated against an international standard preparation calibrated in "IU". One stage clotting assays are known to the art, such as that described in N Lee, Martin L, et al., An Effect of Predilution on Potency Assays of FVIII Concentrates, Thrombosis Research (Pergamon Press Ltd.) 30, 511 519 (1983). Principle of the one stage assay: The test is executed as a modified version of the activated Partial Thromboplastin Time (aPTT)-assay: Incubation of plasma with phospholipids and a surface activator leads to the activation of factors of the intrinsic coagulation system. Addition of calcium ions triggers the coagulation cascade. The time to formation of a measurable fibrin clot is determined. The assay is executed in the presence of Factor VIII deficient plasma. The coagulation capability of the deficient plasma is restored by Coagulation Factor VIII included in the sample to be tested. The shortening of coagulation time is proportional to the amount of Factor VIII present in the sample. The activity of Coagulation Factor VIII is quantified by direct comparison to a standard preparation with a known activity of Factor VIII in International Units.

Another standard assay is a chromogenic substrate assay. Chromogenic substrate assays may be purchased commercially, such as the coamatic FVIII test kit (Chromogenix-Instrumentation Laboratory SpA V. le Monza 338-20128 Milano, Italy). Principle of the chromogenic assay: In the presence of calcium and phospholipid, Factor X is activated by Factor IXa to Factor Xa. This reaction is stimulated by Factor VIIIa as cofactor. FVIIIa is formed by low amounts of thrombin in the reaction mixture from FVIII in the sample to be measured. When using the optimum concentrations of $Ca^{2+}$, phospholipid and Factor IXa and an excess quantity of Factor X, activation of Factor X is proportional to the potency of Factor VIII. Activated Factor X releases the chromophore pNA from the chromogenic substrate S-2765. The release of pNA, measured at 405 nm, is therefore proportional to the amount of FXa formed, and, therefore, also to the Factor VIII activity of the sample.

Pharmaceutical Compositions

Therapeutic formulations of the polypeptide of the invention suitable in the methods described herein can be prepared for storage as lyophilized formulations or aqueous solutions by mixing the polypeptide having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethyl-benzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a second therapeutic agent in addition to a polypeptide of the invention. Examples of suitable second therapeutic agents are provided below.

The dosing schedule can vary from once a month to daily depending on a number of clinical factors, including the type of disease, severity of disease, and the patient's sensitivity to the polypeptide of the invention. In specific embodiments, a polypeptide of the invention is administered, twice weekly, every 5 days, once weekly, every 10 days, every two weeks, every three weeks, every four weeks or once a month, or in any range between any two of the foregoing values, for example from every four weeks to every month, from every 10 days to every two weeks, or from two to three times a week, etc.

The dosage of a polypeptide of the invention to be administered will vary according to the particular polypeptide, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of a polypeptide of the invention will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

According to an aspect of this invention the binding affinity of the polypeptide of the present invention to FVIII is higher than that of a reference polypeptide which has the same amino acid sequence except for the modification(s) in SEQ ID NO:3.

The binding affinity of a VWF molecule to a Factor VIII molecule can be determined by a binding assay used in the art. For example, the VWF molecule may be immobilized on a solid support, increasing concentrations of Factor VIII are applied, incubated for a certain period of time, and after washing, bound Factor VIII is determined with a chromogenic assay. The affinity constant or dissociation constant may then be determined by Scatchard analysis or another suitable method. A method of determining the affinity of binding of human Factor VIII to von Willebrand Factor are described in Vlot et al. (1995), Blood, Volume 85, Number 11, 3150-3157.

Any indication herein of affinity, including dissociation constants, preferably refers to the binding of the modified VWF of the invention, or of the polypeptide of the invention to FVIII. The amino acid sequence of single chain of FVIII is shown in SEQ ID NO:15.

As the interaction of VWF with FVIII typically has a high on-rate, changes in the dissociation constant is largely dependent on changes in the off-rate. Accordingly the main focus in increasing the association of VWF with FVIII involves efforts to decrease the off-rate between FVIII and VWF. Preferably the off-rate of the modified VWF and FVIII in comparison to wild type VWF and FVIII is at least two fold lower, more preferably at least 5 fold lower, preferably at least 10 fold lower and more preferably at least 20 fold lower.

The dissociation constant of the complex consisting of VWF and FVIII is preferably 0.2 nmol/L or less, more preferably 0.175 nmol/L or less, more preferably 0.15 nmol/L or less, more preferably 0.125 nmol/L or less, more preferably 0.1 nmol/L or less, more preferably 0.05 nmol/L or less, most preferably 0.01 nmol/L or less.

The dissociation constant KD of a complex of the polypeptide of the invention and the Factor VIII of SEQ ID NO:15 is typically less than 90% of the dissociation constant KD of a complex of the reference polypeptide (e.g. the polypeptide of SEQ ID NO:4) and the Factor VIII of SEQ ID NO:15. The dissociation constant KD of a complex of the polypeptide of the invention and the Factor VIII of SEQ ID NO:14 is preferably less than 75%, more preferably less than 50%, more preferably less than 25%, more preferably less than 10%, more preferably less than 5%, of the dissociation constant KD of a complex of the reference polypeptide (e.g. the polypeptide of SEQ ID NO:3) and the Factor VIII of SEQ ID NO:15.

The reference polypeptide is a polypeptide the amino acid sequence of which is identical to that of the polypeptide of the present invention except for the mutation within the D'-D3 domains of VWF. That is, the reference polypeptide preferably has an amino acid sequence identical to that of the polypeptide of the present invention, with the proviso that the D'-D3 domains in the reference polypeptide consist of the amino acid sequence as shown in SEQ ID NO:3. In other words, the only difference in sequence between the polypeptide of the invention and the reference polypeptide lies in the amino acid sequence of the D'-D3 domains. The reference polypeptide has preferably been prepared under the same conditions as the polypeptide of the invention.

Polynucleotides

The invention further relates to a polynucleotide encoding a modified VWF or a polypeptide comprising said modified VWF, as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

The invention further relates to a group of polynucleotides which together encode the modified VWF of the invention, or the polypeptide of the invention comprising the modified VWF. A first polynucleotide in the group may encode the N-terminal part of the modified VWF, and a second polynucleotide may encode the C-terminal part of the modified VWF.

Yet another aspect of the invention is a plasmid or vector comprising a polynucleotide according to the invention. Preferably, the plasmid or vector is an expression vector. In a particular embodiment, the vector is a transfer vector for use in human gene therapy.

The invention also relates to a group of plasmids or vectors that comprise the above group of polynucleotides. A first plasmid or vector may contain said first polynucleotide, and a second plasmid or vector may contain said second polynucleotide. Alternatively, both coding sequences are cloned into one expression vector either using two separate promoter sequences or one promoter and an internal ribosome entry site (IRES) element which may be used for example to direct the expression of furin to enhance the generation of mature VWF.

Still another aspect of the invention is a host cell comprising a polynucleotide, a plasmid or vector of the invention, or a group of polynucleotides or a group of plasmids or vectors as described herein.

The host cells of the invention may be employed in a method of producing a modified VWF or a polypeptide comprising said modified VWF, which is part of this invention. The method comprises:

(a) culturing host cells of the invention under conditions such that the desired modified protein is expressed; and
(b) optionally recovering the desired modified protein from the host cells or from the culture medium.

It is preferred to purify the modified VWF of the present invention, or the polypeptide comprising the modified VWF to ≥80% purity, more preferably ≥95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified modified VWF of the invention or polypeptide of the invention is substantially free of other, non-related polypeptides.

The various products of the invention are useful as medicaments. Accordingly, the invention relates to a pharmaceutical composition comprising a modified VWF or a polypeptide comprising said modified VWF as described herein, a polynucleotide of the invention, or a plasmid or vector of the invention.

The invention also concerns a method of treating an individual suffering from a blood coagulation disorder such as hemophilia A or B or VWD. The method comprises administering to said individual an efficient amount of (i) FVIII and of the modified VWF or the polypeptide comprising the modified VWF or (ii) of the complex of FVIII with modified VWF or (iii) of the complex of FVIII with the polypeptide comprising modified VWF as described herein. In another embodiment, the method comprises administering to the individual an efficient amount of a polynucleotide of the invention or of a plasmid or vector of the invention. Alternatively, the method may comprise administering to the individual an efficient amount of the host cells of the invention described herein.

Expression of the Modified Polypeptides

The production of recombinant mutant proteins at high levels in suitable host cells requires the assembly of the above-mentioned modified polynucleotides, typically cDNA, into efficient transcriptional units together with suitable regulatory elements in a recombinant expression vector that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the modified FVIII and/or VWF proteins. Preferably this cell line should be an animal cell-line of vertebrate origin in order to ensure correct folding, disulfide bond formation, asparagine-linked glycosylation and other post-translational modifications as well as secretion into the cultivation medium. Examples on other post-translational modifications are tyrosine O-sulfation and proteolytic processing of the nascent polypeptide chain. Examples of cell lines that can be used are monkey COS-cells, mouse L-cells, mouse C127-cells, hamster BHK-21 cells, human embryonic kidney 293 cells, and hamster CHO-cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNA's can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to gentamycin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated to the genome of the host cell, frequently resulting in a tight physical linkage between the different transcription units.

Other types of selectable marker genes which can be used together with the cDNA of the desired protein are based on various transcription units encoding dihydrofolate reductase (dhfr). After introduction of this type of gene into cells lacking endogenous dhfr-activity, preferentially CHO-cells (DUKX-B11, DG-44), it will enable these to grow in media lacking nucleosides. An example of such a medium is Ham's F12 without hypoxanthine, thymidine, and glycine. These dhfr-genes can be introduced together with the FVIII cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant mutant proteins Purification and Formulation The recombinant modified VWF protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant mutant protein to a monoclonal antibody, directed to e.g. a HLEP, preferably human albumin, or directed to the respective coagulation factor, which is immobilised on a solid support. After adsorption of the modified VWF to the support, washing and desorption, the protein can be further purified by a variety of chromatographic techniques based on the above properties.

The order of the purification steps is chosen e.g. according to capacity and selectivity of the steps, stability of the support or other aspects. Preferred purification steps include but are not limited to ion exchange chromatography steps, immune affinity chromatography steps, affinity chromatography steps, hydrophobic interaction chromatography steps, dye chromatography steps, hydroxyapatite chromatography steps, multimodal chromatography steps, and size exclusion chromatography steps.

In order to minimize the theoretical risk of virus contaminations, additional steps may be included in the process that provide effective inactivation or elimination of viruses. Such steps e.g. are heat treatment in the liquid or solid state, treatment with solvents and/or detergents, radiation in the visible or UV spectrum, gamma-radiation or nanofiltration.

The modified polynucleotides (e.g. DNA) of this invention may also be integrated into a transfer vector for use in the human gene therapy.

The various embodiments described herein may be combined with each other. The present invention will be further described in more detail in the following examples thereof. This description of specific embodiments of the invention will be made in conjunction with the appended figures.

The modified VWF as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3rd edition, Kibbe et al., Pharmaceutical Press (2000)). Standard pharmaceutical formulation techniques are well known to persons skilled in the art (see, e.g., 2005 Physicians' Desk Reference®, Thomson Healthcare: Montvale, N.J., 2004; Remington: The Science and Practice of Pharmacy, 20th ed., Gennaro et al., Eds. Lippincott Williams & Wilkins: Philadelphia, Pa., 2000). In particular, the pharmaceutical composition comprising the polypeptide variant of the invention may be formulated in lyophilized or stable liquid form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially, the compositions of the invention are administered systemically. For systemic use, the proteins of the invention are formulated for parenteral (e.g. intravenous, subcutaneous, intramuscular, intraperitoneal, intracerebral, intrapulmonary, intranasal or transdermal) or enteral (e.g., oral, vaginal or rectal) delivery according to conventional methods. The most preferential routes of administration are intravenous and subcutaneous administration. The formulations can be administered continuously by infusion or by bolus injection. Some formulations encompass slow release systems.

The proteins of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, and mode of administration and has to be determined in preclinical and clinical trials for each respective indication.

The pharmaceutical composition of the invention may be administered alone or in conjunction with other therapeutic agents. These agents may be incorporated as part of the same pharmaceutical. One example of such an agent is the combination of modified VWF with FVIII.

"N-linked glycans" are oligosaccharides that are covalently linked to asparagine residues of a polypeptide. Terminal galactoses on such N-linked glycans may be modified by the attachment of an α-2,3- or an α-2,6-linked sialic acid.

The term "sialic acid" refers to the N- or O-substituted derivatives of neuraminic acid usually found as terminal monosaccharides of animal oligosaccharides (for review, see Varkis (1992) Glycobiology vol. 2 no. 1 pp. 25-40). The most common sialic acid is N-acetyl neuraminic acid. An "increased sialylation" means that at least 85% of the N-glycans of the glycoprotein comprise, on average, at least one sialic acid moiety. By way of non-limiting example an "increased sialylation of at least 85%" is determined as in Example 6 of the present invention, i.e. by enzymatically cleaving all N-glycans from a given glycoprotein of interest and then determining the amount of cleaved N-glycans with no sialic acids ("asialo N-glycans") and the total amount of all cleaved N-glycans. A "sialylation of at least 85%" corresponds then to an amount of 15% of asialo N-glycans or less of the total amount of all cleaved N-glycans.

In a first step, the methods of the invention comprise the step of providing cells comprising a nucleic acid encoding a polypeptide comprising a truncated von Willebrand Factor (VWF).

As described in more detail below, the method of the invention comprises providing cells comprising a nucleic acid encoding the polypeptide comprising the truncated VWF. The nucleic acid is introduced into suitable host cells by techniques that are known per se.

Culturing the Cells

In an embodiment the invention comprises culturing the cells at a temperature of less than 36.0° C. This method comprises culturing the cells under conditions that allow expression of the polypeptide.

The basal medium chosen for culturing the host cell line is not critical to the present invention and may be any one of, or combination of, those known to the art which are suitable for culturing mammalian cells. Media such as Dulbecco's Modified Eagle Medium, Ham's F-12 Medium, Eagle's Minimal Essential Medium and RPMI-1640 Medium and the like are commercially available. The addition of growth factors such as recombinant insulin is optional. In one embodiment, the medium is "protein-free" in the sense that it is either completely free of any protein or at least are free of any protein that is not recombinantly produced. Human serum albumin may be used as a serum-free culture supplement for the production of the polypeptide. Preferably, the medium contains a protease inhibitor, such as a serine protease inhibitor, which is suitable for tissue culture and which is of synthetic or vegetable origin.

Generally, the present invention may be used with any cell culture method that is amenable to the expression of polypeptides. For example, cells may be grown in batch or fed-batch cultures, where the culture is terminated after sufficient expression of the polypeptide, after which the expressed polypeptide is harvested. Alternatively, cells may be grown in continuous cultures (e.g. perfusion cultures), where the culture is not terminated and new nutrients and other components are periodically or continuously added to the culture, during which the expressed polypeptide is harvested periodically or continuously. The latter embodiment is preferred if the method comprises a temperature shift as described herein below. The culture can be any conventional type of culture, such as batch, fed-batch or continuous, but is preferably continuous. Suitable continuous cultures include perfusion culture.

Cells may be grown in any convenient volume chosen by the practitioner. For example, cells may be grown in small scale reaction vessels ranging in volume from a few milliliters to several liters. Alternatively, cells may be grown in large scale commercial bioreactors ranging in volume from approximately at least 1 liter to 10, 100, 250, 500, 1000, 2500, 5000, 8000, 10,000, 12,000 liters or more, or any volume in between. The culture is typically carried out in a bioreactor, which is usually a stainless steel, glass or plastic vessel of 1 (one) to 10000 (ten thousand) litres capacity, for example 5, 10, 50, 100, 1000, 2500, 5000 or 8000 litres. The vessel is usually rigid but flexible plastic bags can be used, particularly for smaller volumes. These are generally of the 'single use' type.

Mammalian cells such as CHO and BHK cells are generally cultured as suspension cultures. That is to say, the cells are suspended in the medium, rather than adhering to a solid support. The cells may alternatively be immobilized on a carrier, in particular on a microcarrier. Porous carriers, such as Cytoline®, Cytopore® or Cytodex®, may be particularly suitable.

To obtain a high sialylation, the cells (e.g. CHO cells) are preferably cultured at a decreased temperature, e.g. at less than 36.0° C. "Decreased temperature" refers to a temperature that is lower than the optimum temperature or normal temperature for growth of the respective cell line. For most mammalian cells the normal temperature is 37° C. It is therefore preferred according to the invention that the cells (e.g. CHO cells) are cultured at a decreased temperature of 30.0 to 36.0° C., 30.5 to 35.5° C., 31.0 to 35.0° C., 31.5 to 34.5° C., 32.0 to 34.0° C., or 32.5 to 33.5° C. Preferably, the cells are cultured at a decreased temperature of 30.0° C.±1.0° C., 31.0° C.±1.0° C., 32.0° C.±1.0° C., 33.0° C.±1.0° C., 34.0° C.±1.0° C., or 35.0° C.±1.0° C.

The decreased temperature is maintained for a time period that is sufficient to increase the sialylation of the polypeptide to be expressed. Preferably, the decreased temperature is maintained for at least 1 hour, at least 6 hours, at least 12 hours, at least 18 hours, at least 24 hours, at least 48 hours, at least 72 hours, at least 96 hours, at least 120 hours, or at least 144 hours. In other embodiments, the decreased temperature is maintained for 1 hour to 8 weeks, 6 hours to 6 weeks, 12 hours to 5 weeks, 18 hours to 4 weeks, 24 hours to 3 weeks, 48 hours to 14 days, 72 hours to 10 days, or 3 to 7 days.

To accomplish this, a culture may be subjected to one or more temperature shifts during the course of the culture.

When shifting the temperature of a culture, the temperature shift may be relatively gradual. For example, it may take several hours or days to complete the temperature change. Alternatively, the temperature shift may be relatively abrupt. The temperature may be steadily increased or decreased during the culture process. Alternatively, the temperature may be increased or decreased by discrete amounts at various times during the culture process. The subsequent temperature(s) or temperature range(s) may be lower than or higher than the initial or previous temperature(s) or temperature range(s). One of ordinary skill in the art will understand that multiple discrete temperature shifts are encompassed in this embodiment. For example, the temperature may be shifted once (either to a higher or lower temperature or temperature range), the cells maintained at this temperature or temperature range for a certain period of time, after which the temperature may be shifted again to a new temperature or temperature range, which may be either higher or lower than the temperature or temperature range of the previous temperature or temperature range. The temperature of the culture after each discrete shift may be constant or may be maintained within a certain range of temperatures.

Typically, the cells (e.g. CHO cells) will initially be cultured at a "normal" temperature of 37.0° C.±1.0° C. until the target cell density is achieved. The initial culture period is then followed by a temperature shift to the decreased temperature. After a period of culturing at the decreased temperature, a temperature shift to the normal temperature may or may not follow. Preferably, the cells (e.g. CHO cells) will initially be cultured at 37.0° C.±1.0° C. for several days, followed by manufacturing at a decreased temperature of 31.0-35.0° C.

Based on the present disclosure, those of ordinary skill in the art will be able to select temperatures in which to grow cells, depending on the particular needs of the respective cell line and the particular production requirements of the practitioner.

In certain embodiments, batch and fed-batch bioreactors are terminated once the expressed polypeptide reaches a sufficiently high titer. Additionally or alternatively, batch and fed-batch bioreactors may be terminated once the cells reach a sufficiently high density, as determined by the needs of the practitioner. For example, the culture may be terminated once the cells reach 1, 5, 10, 15, 20, 25, 30, 35, 40, 45, 50, 55, 60, 65, 70, 75, 80, 85, 90, 95 or 99 percent of maximal viable cell density. Additionally or alternatively, batch and fed-batch bioreactors may be terminated prior to excessive accumulation of metabolic waste products such as lactate and ammonium.

In certain cases, it may be beneficial to supplement a cell culture during the subsequent production phase with nutrients or other medium components that have been depleted or metabolized by the cells. As non-limiting examples, it may be beneficial to supplement a cell culture with hormones and/or other growth factors, inorganic ions (such as, for example, sodium, chloride, calcium, magnesium, and phosphate), buffers, vitamins, nucleosides or nucleotides, trace elements (inorganic compounds usually present at very low final concentrations), amino acids, lipids, or glucose or other energy source. Such supplementary components may all be added to the cell culture at one time, or they may be provided to the cell culture in a series of additions or they may be provided together with fresh medium during a perfusion culture.

Alternatively to batch and fed-batch bioreactors the invention can also be practiced when cells expressing a polypeptide of the invention are cultured in continuous perfusion bioreactors.

One of ordinary skill in the art will be able to tailor specific cell culture conditions in order to optimize certain characteristics of the cell culture including but not limited to growth rate, cell viability, final cell density of the cell culture, final concentration of detrimental metabolic byproducts such as lactate and ammonium, titer of the expressed polypeptide, extent and composition of the oligosaccharide side chains or any combination of these or other conditions deemed important by the practitioner.

Isolation of the Expressed Polypeptide

In general, it will typically be desirable to isolate and/or purify polypeptides expressed according to the present invention. In certain embodiments, the expressed polypeptide is secreted into the medium and thus cells and other solids may be removed, as by centrifugation or filtering for example, as a first step in the purification process.

The expressed polypeptide may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol. 182), Academic Press, 1997, each of which is incorporated herein by reference). For immunoaffinity chromatography in particular, the polypeptide may be isolated by binding it to an affinity column comprising antibodies that were raised against that polypeptide and were affixed to a stationary support. Alternatively, affinity tags such as an influenza coat sequence, poly-histidine, or glutathione-S-transferase can be attached to the polypeptide by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide during the purification process. Protease inhibitors are particularly advantageous when cells must be lysed in order to isolate and purify the expressed polypeptide. Additionally or alternatively, glycosidase inhibitors may be added at any or all stages in order to reduce or eliminate enzymatic trimming of the covalently attached oligosaccharide chains.

Polypeptides expressed according to the present invention have more extensive sialylation than they would if grown under traditional cell culture conditions. Thus, one practical benefit of the present invention that may be exploited at the purification step is that the additional and/or altered sialic acid residues on a polypeptide grown in accordance with certain of the present inventive methods may confer on it distinct biochemical properties that may be used by the practitioner to purify that polypeptide more easily, or to a greater purity, than would be possible for a polypeptide grown in accordance with more traditional methods. For example, the polypeptide can be purified or greatly enriched by anion exchange chromatography, making use of the negative charge of the sialic acid residues. Thereby a further enrichment of polypeptide with high sialylation can be achieved.

In a further embodiment, the sialylation of the polypeptide obtained by a method of the invention can be further increased by contacting the polypeptide with a sialyltransferase in vitro. The sialyltransferase typically is a mammalian sialyltransferase, preferably it is a human sialyltransferase. The sialyltransferase may be an α-2,3-sialyltransferase and/or an α-2,6-sialyltransferase. Preferably, the sialyltransferase is a human α-2,3-sialyltransferase (Genbank NP_775479-ST3GAL 1) and/or a human α-2,6-sialyltransferase. Most preferably, the sialyltransferase is human α-2,6-sialyltransferase identified by Genbank NP_003023-ST6GAL 1). Further present in the in vitro reaction is a sialyl group donor, or sialic acid donor. Suitable donors include, e.g., Cytidine-5'-monophospho-N-acetylneuraminic acid (CMP-NANA), Roche Catalog No. 05 974 003 103. A suitable kit for in vitro sialylation is available from Roche (Catalog Number 07 012 250 103).

One of ordinary skill in the art will appreciate that the exact purification technique will vary depending on the character of the polypeptide to be purified, the character of the cells from which the polypeptide is expressed, and/or the composition of the medium in which the cells were grown.

As mentioned above, the invention, in a second aspect, relates to a method of producing a polypeptide comprising N-glycans with increased sialylation, which comprises (i) providing cells comprising a nucleic acid encoding a polypeptide comprising a truncated von Willebrand Factor (VWF) and a recombinant nucleic acid encoding an α-2,3-sialyltransferase and/or an α-2,6-sialyltransferase, preferably an α-2,6-sialyltransferase, and (ii) culturing the cells under conditions that allow expression of the polypeptide.

The α-2,3-sialyltransferase preferably is a human α-2,3-sialyltransferase. The cDNA sequence encoding human α-2, 3-sialyltransferase is shown in SEQ ID NO:12, and based thereon the skilled artisan can design suitable expression vectors containing a coding sequence of α-2,3-sialyltransferase.

The α-2,6-sialyltransferase preferably is a human α-2,6-sialyltransferase. The cDNA sequence encoding human α-2, 6-sialyltransferase is shown in SEQ ID NO:31, and based thereon the skilled artisan can design suitable expression vectors containing a coding sequence of α-2,6-sialyltransferase.

The transfected cells can be cultured under conditions allowing expression of the polypeptide according to known culturing methods.

The polypeptide can be recovered and/or isolated using established purification techniques.

Polypeptide of the Invention

The present invention also relates to a polypeptide obtainable by a method described herein.

In another aspect, the invention relates to a polypeptide comprising a truncated von Willebrand Factor (VWF), wherein said truncated VWF is capable of binding to a Factor VIII (FVIII), and wherein said polypeptide comprises N-glycans, and at least 85%, more preferably at least 90% of said N-glycans comprise, on average, at least one sialic acid moiety. In preferred embodiments, at least 91%, at least 92%, at least 93%, at least 94%, at least 95%, at least 96%, at least 97%, at least 98%, or at least 99%, of said N-glycans comprise, on average, at least one sialic acid moiety. The inventors demonstrated that polypeptides comprising highly sialylated VWF fragments not only have a prolonged half-life themselves, but are also capable to extend the half-life of co-administered FVIII. In other words, administration of the polypeptide of the invention leads to an extended half-life and/or to a reduced clearance of co-administered FVIII.

In a fifth aspect, the invention relates to a polypeptide comprising a truncated von Willebrand Factor (VWF), wherein said truncated VWF is capable of binding to a Factor VIII (FVIII), and wherein said polypeptide comprises N-glycans, wherein at least 50% of the sialyl groups of the N-glycans of the polypeptides are α-2,6-linked sialyl groups. In general, terminal sialyl groups can be attached to the galactose groups via a α-2,3- or via a α-2,6-linkage. Typically, N-glycans of the polypeptide of the invention comprise more α-2,6-linked sialyl groups than α-2,3-linked sialyl groups. Preferably, at least 60%, or at least 70%, or at least 80%, or at least 90% of the sialyl groups of the N-glycans are α-2,6-linked sialyl groups. These embodiments can be obtained by, e.g., co-expressing human α-2, 6-sialyltransferase in mammalian cells.

In one embodiment, at least 85%, at least 90%, or at least 95%, or at least 96%, or at least 97%, or at least 98%, or at least 99% of the N-glycans of the polypeptide of the invention comprise at least one sialic acid group. In another embodiment, at least 90%, or at least 95%, or at least 96%, or at least 97%, or at least 98%, or at least 99% of the N-glycans of the truncated VWF within the polypeptide of the invention comprise at least one sialic acid group.

In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they are N-glycans lacking a sialic acid group. In another embodiment, less than 15%, less than 12%, less than 10%, or less than 8%, or less than 6%, or less than 5%, or less than 4%, or less than 3%, or less than 2% or even less than 1% of the N-glycans of the truncated VWF within the polypeptide of the invention are asialo-N-glycans, i.e. they do not have a sialic acid group.

In another embodiment, less than 25%, less than 20%, less than 15%, or less than 10%, of the N-glycans of the polypeptide of the invention are monosialo-N-glycans, i.e. they are N-glycans with one sialic acid group. In another embodiment, less than 25%, less than 20%, less than 15%, or less than 10%, of the N-glycans of the truncated VWF within the polypeptide of the invention are monosialo-N-glycans, i.e. they are N-glycans with one sialic acid group. By way of non-limiting example the amount of monosialylated N-glycans can be determined as detailed in Example 6.

In yet another embodiment, at least 20%, or at least 25%, of the N-glycans of the polypeptide of the invention are disialo-N-glycans, i.e. they are N-glycans with 2 sialic acid groups. In yet another embodiment, at least 20%, or at least 25%, of the N-glycans of the truncated VWF within the polypeptide of the invention are disialo-N-glycans.

In yet another embodiment, at least 10%, or at least 15%, or at least 20%, or at least 25%, of the N-glycans of the polypeptide of the invention are trisialo-N-glycans, i.e. they are N-glycans with 3 sialic acid groups. In yet another embodiment, at least 10%, or at least 15%, or at least 20%, or at least 25%, of the N-glycans of the truncated VWF within the polypeptide of the invention are trisialo-N-glycans.

In yet another embodiment, at least 5%, or at least 10%, of the N-glycans of the polypeptide of the invention are tetrasialo-N-glycans, i.e. they are N-glycans with 4 sialic acid groups. In yet another embodiment, at least 10%, or at least 15%, of the N-glycans of the truncated VWF within the polypeptide of the invention are tetrasialo-N-glycans.

In another embodiment, at least 50%, or at least 60%, or at least 70%, or at least 80%, of the N-glycans of the polypeptide of the invention comprise two or more sialic acid groups. In another embodiment, at least 50%, or at least 60%, or at least 70%, or at least 80%, of the N-glycans of the truncated VWF within the polypeptide of the invention comprise two or more sialic acid groups.

The above-described embodiments can be combined with each other. Any percentages of N-glycans mentioned above, or any indications of the degree of sialylation, are to be understood as average percentages or degrees, i.e. they refer to a population of molecules, not to a single molecule. It is clear that the glycosylation or sialylation of the individual polypeptide molecules within a population of polypeptides will show some heterogeneity.

Another aspect of the present invention is a pharmaceutical kit comprising (i) a polypeptide as defined hereinabove and (ii) a Factor VIII. Preferably, the polypeptide and the FVIII are contained in separate compositions.

Another aspect of the present invention is a pharmaceutical kit comprising (i) a polypeptide as defined hereinabove and (ii) a Factor VIII, for simultaneous, separate or sequential use in the treatment of a blood coagulation disorder.

A summary of the sequences referred to herein is set out in Table 3.

TABLE 3

| SEQ ID NO: | Description |
|---|---|
| 1 | Nucleotide sequence of DNA encoding SEQ ID NO: 2 |
| 2 | Amino acid sequence of human VWF pre-propolypeptide |
| 3 | Amino acid sequence of D'-D3 domains of human VWF |
| 4 | Amino acid sequence of mature human VWF |
| 5 | Truncated VWF including mutations S764P/S766W/V1083A |
| 6 | Truncated VWF including mutations S764G/S766Y/V1083A |
| 7 | Truncated VWF including mutations S764E/S766Y/V1083A |
| 8 | Truncated VWF including mutations N1011S/V1083A/K1181E |
| 9 | Truncated VWF including mutation V1083A |
| 10 | Truncated VWF including mutation S1042T |
| 11 | Truncated VWF including mutations V805A/Q1158L |
| 12 | Truncated VWF including mutations K912E/T1088S |
| 13 | Truncated VWF including mutation L781P |
| 14 | Amino acid sequence of human Factor VIII |
| 15 | Amino acid sequence of a mature single-chain Factor VIII |
| 16 | Amino acid sequence of human serum albumin |
| 17 | Truncated VWF including mutations S766Y/V1083A |
| 18 | Truncated VWF including mutations S764G/S766Y |
| 19 | Truncated VWF including mutations S764P/S766I |
| 20 | Truncated VWF including mutations S764P/S766M |
| 21 | Truncated VWF including mutations S764V/S766Y |
| 22 | Truncated VWF including mutations S764E/S766Y |
| 23 | Truncated VWF including mutations S764Y/S766Y |
| 24 | Truncated VWF including mutations S764L/S766Y |
| 25 | Truncated VWF including mutations S764P/S766W |
| 26 | Truncated VWF including mutations S766W/S806A |
| 27 | Truncated VWF including mutations S766Y/P769K |
| 28 | Truncated VWF including mutations S766Y/P769N |
| 29 | Truncated VWF including mutations S766Y/P769R |
| 30 | Truncated VWF including mutations S764P/S766L |
| 31 | cDNA encoding human α-2,6-sialyltransferase |

EXAMPLES

Example 1 vWF Mutants with Improved FVIII Binding

Background

As discussed above and in co-pending International Patent Application No. PCT/AU2015/050369 the majority of circulating FVIII is in complex with VWF. In humans, FVIII is cleared from the blood with a $t_{1/2}$ of approximately 2 hr and 16 hr in the absence and presence of VWF, respectively. Although VWF imparts an increase in FVIII half-life, it also places an upper limit on the $t_{1/2}$ that is dictated by its own half-life. U.S. Pat. No. 8,575,104 discloses a VWF-albumin fusion protein. This fusion protein has a five-fold longer half-life than wild type VWF in a rodent model. A stable complex between this fusion protein and FVIII may confer additional half-life benefits for FVIII. Although the equilibrium binding constant for the FVIII/vWF interaction is high, the binding kinetics are rapid and any FVIII in complex with the VWF-albumin fusion protein will quickly exchange with endogenous vWF upon infusion. Accordingly if the off-rate of FVIII with VWF-albumin fusion is substantially equivalent to the off-rate of FVIII with native VWF then the use of the VWF-albumin fusion will not provide any substantial increase in the half life of FVIII.

Accordingly, in order to take advantage of the longer half life of the VWF-albumin fusion to extend the half life of FVIII it is necessary to decrease the off-rate of FVIII with the VWF-albumin fusion. From modeling studies taking advantage of measurement made in patients with Type 2N von Willebrand disease in which the level of VWF is normal but the ability of the VWF to associate with FVIII is severely diminished it has been estimated that at least a five fold decrease in off-rate is required to provide a clinically relevant improvement in FVIII half life. The postulated relationship between decrease in FVIII VWF-albumin fusion off-rate and increase in FVIII half life is set out in Table 4.

TABLE 4

| Decrease in FVIII VWF-albumin fusion off-rate | Postulated increase in FVIII half life (For 50 IU/kg of FVIII and 100 IU/kg of VWF with the VWF 5x half life extended) |
| --- | --- |
| 2 fold | 2.2 |
| 3 fold | 2.6 |
| 5 fold | 3 |
| 10 fold | 3.6 |
| 20 fold | 4.1 |

In an effort to decrease FVIII VWF-albumin fusion off-rate experiments were conducted to assess whether mutant VWF-albumin fusion protein may provide a significantly slower FVIII off-rate thereby providing a viable option to extend the half-life of FVIII through stable association with the VWF-albumin fusion protein.

A series of mutants were constructed around amino acid positions 764, 765, 766, 768, 769, 773, 806 and 809 of vWF with the intention of slowing the rate of dissociation of bound FVIII. In these experiments a recombinant form of FVIII was used. This FVIII is described in Zollner et al 2013, Thrombosis Research, 132:280-287. Initially, FVIII binding was measured for vWF constructs that had one of the above mentioned residues mutated to all genetic encoded amino acids, excluding cysteine. Following identification of improved binders additional sets of variants were produced including combinations of mutations. In addition, as the half life extension provided by the albumin fusion is dependent on FcRn-mediated recycling a number of the mutants were also tested at a pH 5.5. The results for the various mutations are shown in Tables 5 to 20.

Methods

A synthetic, codon-optimised cDNA encoding the D' and D3 domains of human von Willebrand Factor (vWF; amino acids (aa) 764-1270 (SEQ ID NO:2); based on GenBank accession no. NP_000543 was obtained from GeneART AG (Regensberg, Germany). This was modified at the 5' end to encode its own signal peptide (aa1-22) and at the 3' end to encode a C-terminal 8×His-tag. The construct (Hu-vWF [764-1270]-8His) was directionally cloned into the pcDNA3.1 mammalian expression vector (Invitrogen, USA) with a Kozak consensus sequence (GCCACC) upstream of the initiating methionine and a double stop codon (TGA) at the 3' end of the open reading frame, and the plasmid sequence confirmed by automated sequencing. This expression plasmid was then used as a template to make single, double or triple residue changes at Ser764, Leu765, Ser766 or Lys773 using standard PCR techniques and the constructs cloned into pcDNA3.1 and sequenced as described above. A second codon-optimised cDNA encoding the D1 and D2 domains (aa1-762) of Hu-vWF with a C-terminal FLAG tag (DYKDDDDK (SEQ ID NO:32)) was also synthesized and obtained from GeneArt; this was cloned as above into pcDNA3.1 and sequenced.

For transient mammalian expression, Freestyle™ 293 suspension cells (Invitrogen] were grown to $1.1 \times 10^6$ cells/ml in 5 ml Freestyle Expression media (Invitrogen). 7 μL 293Fectin (Invitrogen) transfection reagent was pre-incubated for 5 minutes with 167 μL Opti-MEM I medium (Invitrogen), then added to 2.5 μg plasmid DNA encoding wild-type/mutant Hu-vWF[764-1270]-8His plus 2.5 μg plasmid DNA encoding Hu-vWF[1-762]-FLAG and the mixture incubated for a further 20 minutes. The DNA-293Fectin complex was added to the cells which were cultured for 6 days at 37° C., 8% $CO_2$ in a shaking incubator at 250 rpm. Culture supernatants were harvested by centrifugation at 2000 rpm for 5 minutes and stored at 4° C. for analysis.

Binding kinetics were investigated by surface plasmon resonance using a Biacore 4000 biosensor at 37° C. Each mutant was captured from cell culture medium to a density of 40-150 RU on a CM-5 sensor chip pre-immobilised with anti-His antibody (14,000 RU). In an initial screening study, FVIII was injected over the captured mutants for 5 minutes at 1 nM and dissociation monitored for 5 minutes. Mutants that showed a decrease in kd relative to wild-type were then re-examined with FVIII injected for 5 minutes at 1, 0.5 and 0.25 nM, and dissociation monitored for 30 minutes.

All sensorgrams were double referenced by subtraction of signals from a reference spot (containing only immobilised anti His antibody) and from a blank injection. Binding kinetics were determined by fitting the double referenced sensorgrams to a 1:1 kinetic model.

Results

Mutagenesis of serine 764 to proline generated a vWF variant with an approximately 3.5 fold decrease in off-rate and a 4.4 fold increase in affinity. Mutations at position 765 did not yield any better binders vis-a-vis wild type vWF. Numerous mutations at position 766 generated variant vWF molecules with improved off-rate characteristics and higher affinity than wild-type vWF (His, Arg, Val, Tyr, Trp, Thr, Phe, Ile, Gln, Gly & Asn). Given that proline at position 764 conferred significant enhancement to off-rate while numerous mutations at position 766 positively impacted binding, a series of mutants were generated that consisted of S764P and all other genetic encoded amino acids, excluding cysteine, at position 766. Similar mutations were produced that contained S764P and all other genetic encoded amino acids, excluding cysteine, at position 765. A number of these double mutants have significantly slower off-rates and higher affinity vis-a-vis wild type vWF. In particular S764P in combination with S766I generates a vWF variant with a 22 fold decrease in off-rate and a 30 fold increase in affinity.

Example 2

Human Serum Albumin vWF Fusions with Point Mutants and FVIII Binding

Subsequent experiments were conducted using vWF fused to human serum albumin. A synthetic, codon-optimised cDNA encoding the D' and D3 domains of human von Willebrand Factor (vWF; amino acids (aa) 764-1242; based on GenBank accession no. NP_000543) was obtained from GeneART AG (Regensberg, Germany). This was modified at the 5' end to encode its own signal peptide (aa1-22) and at the 3' end to encode human serum albumin (HSA) via a glycine serine linker and cloned as described in Example 1. The same process as described in Example 1 was used to generate the various VWF mutations and the resulting constructs were transiently transfected into Freestyle™ 293 suspension cells. vWF-HSA proteins were purified from harvests using Capture Select™ Human Albumin affinity resin and the vWF-HSA dimer further purified by preparative Size Exclusion Chromatography. Detailed kinetic analysis at pH7 was set up for the top candidates, including controls.

Mouse anti-HSA antibody was immobilized on a CM5 chip using standard NHS/EDC coupling chemistry. Typically, the immobilization level was between 10,000 and 12,000 RU. Each batch of vWF-HSA (monomers and dimers) was captured on a single spot in each flow cell for 2 minutes at various concentrations ranging from 0.1-1 µg/ml. Capture levels ranged from 40-150 RU. An adjacent spot in which anti-vWF was immobilized, but no vWF-HSA captured was used as a reference. Capture was performed every cycle, before FVIII binding analysis.

FVIII was injected at random and in duplicate over all spots in all flow cells at varying concentrations depending on the affinity of the interaction and the pH of the analysis. The association and dissociation of FVIII was monitored for various time frames that best suited the interaction taking place.

Post the dissociation period the surface was regenerated with a 30 second injection of 25 mM Glycine pH2.6. Running buffer throughout was 10 mM HEPES, 150 mM NaCl, 10 mM Na Citrate, 2.5 mM $CaCl_2$), 0.1% BSA, pH7.3 and pH5, while the flow rate was 30 µl/min. Each interaction was measured 4 times (n=4) at 37° C.

Responses for binding to the reference spot were subtracted from those of the vWF-HSA captured spots. Responses from blank injections were then subtracted from those of all other samples to produce double-referenced sensorgrams. Double referenced sensorgrams were fitted to a 1:1 kinetic model, including a term for mass transport limitation. Association and dissociation rates were fitted globally and Rmax fitted locally. The results obtained are set out in Tables 21 and 22.

TABLE 5

S764X mutants were X is one of the remaining genetic encoded amino acids, excluding cysteine.

| Mutant | ka (1/Ms) | kd (1/s) | KD (M) |
|---|---|---|---|
| S764P | 9.07E+06 | 3.25E−04 | 3.58E−11 |
| S764Y | 8.07E+06 | 8.87E−04 | 1.10E−10 |
| S764E | 6.38E+06 | 7.43E−04 | 1.16E−10 |
| S764L | 8.47E+06 | 9.95E−04 | 1.18E−10 |
| S764A | 6.85E+06 | 8.08E−04 | 1.18E−10 |
| S764G | 6.82E+06 | 8.18E−04 | 1.20E−10 |
| S764I | 9.02E+06 | 1.27E−03 | 1.41E−10 |
| S764W | 9.46E+06 | 1.41E−03 | 1.49E−10 |
| wt | 7.33E+06 | 1.15E−03 | 1.57E−10 |
| wt | 7.43E+06 | 1.18E−03 | 1.59E−10 |
| S76R | 1.06E+07 | 1.77E−03 | 1.67E−10 |
| S764F | 8.14E+06 | 1.40E−03 | 1.72E−10 |
| S764N | 6.21E+06 | 1.26E−03 | 2.03E−10 |
| S764M | 8.94E+06 | 1.90E−03 | 2.12E−10 |
| S764V | 7.30E+06 | 1.69E−03 | 2.32E−10 |
| S764T | 7.17E+06 | 1.89E−03 | 2.64E−10 |
| S764D | 6.27E+06 | 1.68E−03 | 2.68E−10 |
| S76H | 8.96E+06 | 2.78E−03 | 3.10E−10 |
| S76K | 1.59E+07 | 5.09E−03 | 3.19E−10 |
| S764Q | 2.97E+06 | 2.04E−03 | 6.86E−10 |

TABLE 6

L765X mutants were X is one of the remaining genetic encoded amino acids, excluding cysteine.

| Mutant | ka (1/Ms) | kd (1/s) | KD (M) |
|---|---|---|---|
| WT-L765A | 3.40E+07 | 7.88E−03 | 2.32E−10 |
| WT-L765N | N/D | | |
| WT-L765Q | N/D | | |
| WT-L765G | N/D | | |
| WT-L765I | 6.01E+06 | 1.16E−03 | 1.92E−10 |
| WT-L765M | 6.81E+06 | 1.95E−03 | 2.87E−10 |
| WT-L765F | 8.91E+06 | 1.74E−03 | 1.96E−10 |
| WT-L765P | 1.13E+08 | 4.80E−02 | 4.25E−10 |
| WT-L765S | 3.46E+07 | 9.13E−03 | 2.64E−10 |
| WT-L765T | 7.53E+07 | 1.75E−02 | 2.32E−10 |
| WT-L765W | 3.53E+07 | 1.42E−02 | 4.03E−10 |
| WT-L765Y | 8.44E+07 | 4.36E−02 | 5.17E−10 |
| WT-L765V | 6.24E+06 | 4.76E−03 | 7.63E−10 |
| WT-L765D | N/D | | |
| WT-L765E | N/D | | |
| WT-L765R | 1.32E+08 | 1.55E−02 | 1.17E−10 |
| WT-L765H | N/D | | |
| WT-L765K | N/D | | |
| WT | 7.33E+06 | 1.15E−03 | 1.57E−10 |

N/D: weak binding, poor fit, fast off rate

TABLE 7

S766X mutants were X is one of the remaining genetic encoded amino acids, excluding cysteine.

| Mutant | ka (1/Ms) | kd (1/s) | KD (M) |
|---|---|---|---|
| WT-S766A | 7.47E+06 | 1.54E−03 | 2.06E−10 |
| WT-S766N | 8.71E+06 | 8.80E−04 | 1.01E−10 |
| WT-S766Q | 7.42E+06 | 5.16E−04 | 6.94E−11 |
| WT-S766G | 9.34E+06 | 1.88E−03 | 2.01E−10 |
| WT-S766I | 6.17E+06 | 7.93E−04 | 1.29E−10 |
| WT-S766L | 7.31E+06 | 1.21E−03 | 1.65E−10 |
| WT-S766M | N/D | | |
| WT-S766F | 7.46E+06 | 2.74E−04 | 3.67E−11 |
| WT-S766P | 1.16E+07 | 3.45E−03 | 2.98E−10 |
| WT-S766T | 7.12E+06 | 4.98E−04 | 7.00E−11 |
| WT-S766W | 6.62E+06 | 2.03E−04 | 3.07E−11 |
| WT-S766Y | 6.98E+06 | 1.95E−04 | 2.79E−11 |
| WT-S766V | 6.01E+06 | 2.60E−04 | 4.33E−11 |
| WT-S766D | N/D | | |
| WT-S766E | 2.53E+07 | 1.89E−03 | 7.48E−11 |
| WT-S766R | 9.04E+06 | 3.63E−04 | 4.02E−11 |
| WT-S766H | 7.19E+06 | 3.06E−04 | 4.25E−11 |
| WT-S766K | 1.02E+07 | 3.22E−03 | 3.14E−10 |
| WT | 7.33E+06 | 1.15E−03 | 1.57E−10 |

N/D: weak binding, poor fit, fast off-rate

TABLE 8

| Mutant | Ka (1/Ms) | kd (1/s) | KD (M) |
|---|---|---|---|
| WT-K773T | 1.42E+07 | 6.97E−04 | 4.92E−11 |
| WT-K773A | 5.81E+06 | 8.83E−04 | 1.52E−10 |
| WT-K773L | 1.88E+07 | 1.10E−03 | 5.86E−11 |
| WT-K773R | 1.45E+07 | 1.23E−03 | 8.46E−11 |
| WT-K773Q | 8.60E+06 | 1.45E−03 | 1.68E−10 |
| WT-K773M | 1.57E+07 | 2.35E−03 | 1.50E−10 |

TABLE 8-continued

| Mutant | Ka (1/Ms) | kd (1/s) | KD (M) |
|---|---|---|---|
| WT-K773S | 1.35E+07 | 3.23E−03 | 2.40E−10 |
| WT-K773P | 9.58E+06 | 3.33E−03 | 3.48E−10 |
| WT-K773I | 7.66E+07 | 4.09E−03 | 5.35E−11 |
| WT-K773V | 5.39E+07 | 5.23E−03 | 9.70E−11 |
| WT-K773H | 1.19E+09 | 1.57E−01 | 1.32E−10 |
| WT-K773N | 3.61E+09 | 8.36E−01 | 2.32E−10 |
| WT-K773W | N/D | | |
| WT-K773E | N/D | | |
| WT-K773D | N/D | | |
| WT-K773G | N/D | | |
| WT-K773F | N/D | | |
| WT-K773Y | N/D | | |
| WT | 7.33E+06 | 1.15E−03 | 1.57E−10 |

N/D: Binding was present, but accurate kinetic parameters could not be determined

TABLE 9

S764P, L765X mutants were X is one of the remaining genetic encoded amino acids, excluding cysteine.

| Mutant | ka (1/Ms) | kd (1/s) | KD (M) |
|---|---|---|---|
| S764P-L765A | 3.07E+07 | 2.78E−02 | 9.06E−10 |
| S764P-L765N | N/D | | |
| S764P-L765Q | 8.12E+06 | 7.14E−03 | 8.80E−10 |
| S764P-L765G | N/D | | |
| S764P-L765I | 8.08E+06 | 9.52E−05 | 1.18E−11 |
| S764P-L765M | 9.76E+06 | 2.37E−04 | 2.43E−11 |
| S764P-L765F | 1.69E+07 | 6.32E−04 | 3.73E−11 |
| S764P-L765P | 1.02E+07 | 2.42E−04 | 2.38E−11 |
| S764P-L765S | N/D | | |
| S764P-L765T | 1.39E+07 | 8.82E−03 | 6.34E−10 |
| S764P-L765W | 7.97E+06 | 5.14E−03 | 6.45E−10 |
| S764P-L765Y | 6.19E+06 | 2.20E−03 | 3.55E−10 |
| S764P-L765V | 6.19E+06 | 2.20E−03 | 3.55E−10 |
| S764P-L765D | N/D | | |
| S764P-L765E | N/D | | |
| S764P-L765R | N/D | | |
| S764P-L765H | 1.16E+07 | 6.42E−03 | 5.55E−10 |
| S764P-L765K | N/D | | |
| WT | 7.33E+06 | 1.15E−03 | 1.57E−10 |

N/D: weak binding, poor fit, fast off-rate

TABLE 10

S764P, S766X mutants were X is one of the remaining genetic encoded amino acids, excluding cysteine.

| Mutant | ka (1/Ms) | kd (1/s) | KD (M) |
|---|---|---|---|
| S764P-S766A | 1.35E+07 | 1.66E−04 | 1.23E−11 |
| S764P-S766N | 8.82E+06 | 9.14E−05 | 1.04E−11 |
| S764P-S766Q | 1.20E+07 | 1.23E−04 | 1.02E−11 |
| S764P-S766G | 1.79E+07 | 3.88E−04 | 2.17E−11 |
| S764P-S766I | 9.84E+06 | 5.14E−05 | 5.23E−12 |
| S764P-S766L | 1.44E+07 | 8.74E−05 | 6.06E−12 |
| S764P-S766M | 1.18E+07 | 5.76E−05 | 4.88E−12 |
| S764P-S766F | 1.35E+07 | 1.00E−04 | 7.41E−12 |
| S764P-S766P | 2.56E+07 | 2.17E−03 | 8.48E−11 |
| S764P-S766T | 9.01E+06 | 1.05E−04 | 1.16E−11 |
| S764P-S766W | 1.10E+07 | 8.00E−05 | 7.27E−12 |
| S764P-S766Y | 1.08E+07 | 7.71E−05 | 7.16E−12 |
| S764P-S766V | 8.19E+05 | 7.82E−05 | 9.56E−11 |
| S764P-S766D | 9.41E+06 | 1.20E−04 | 1.27E−11 |
| S764P-S766E | 8.04E+06 | 1.28E−04 | 1.60E−11 |
| S764P-S766R | 1.29E+07 | 1.19E−04 | 9.21E−12 |
| S764P-S766H | 1.40E+07 | 9.47E−05 | 6.76E−12 |
| S764P-S766K | 2.15E+07 | 3.01E−04 | 1.40E−11 |
| WT | 7.33E+06 | 1.15E−03 | 1.57E−10 |

N/D: weak binding poor fit, fast off-rate

TABLE 11

| Mutant | ka (1/Ms) | kd (1/s) | KD (M) |
|---|---|---|---|
| S764P-K773R | 6.39E+06 | 7.42E−05 | 1.16E−11 |
| S764P-K773T | 4.68E+06 | 7.50E−05 | 1.60E−11 |
| S764P-K773Q | 4.44E+06 | 1.28E−04 | 2.88E−11 |
| S764P-K773V | 1.55E+07 | 1.57E−04 | 1.01E−11 |
| S764P-K773I | 1.79E+07 | 1.69E−04 | 9.43E−12 |
| S764P-K773M | 1.58E+07 | 1.70E−04 | 1.08E−11 |
| S764P-K773A | 6.37E+06 | 1.89E−04 | 2.97E−11 |
| S764P-K773S | 2.16E+07 | 3.06E−04 | 1.42E−11 |
| S764P-K773N | 5.50E+06 | 3.47E−04 | 6.31E−11 |
| S764P-K773P | 2.26E+07 | 5.01E−04 | 2.22E−11 |
| S764P-K773L | 4.60E+05 | 5.72E−04 | 1.24E−09 |
| S764P-K773H | 1.65E+07 | 6.36E−04 | 3.86E−11 |
| S764P-K773G | 1.75E+07 | 7.62E−04 | 4.36E−11 |
| S764P-K773F | 1.02E+07 | 1.23E−03 | 1.21E−10 |
| S764P-K773Y | 1.63E+07 | 1.36E−03 | 8.35E−11 |
| S764P-K773D | 1.77E+07 | 2.40E−03 | 1.36E−10 |
| S764P-K773W | 1.25E+07 | 3.21E−03 | 2.57E−10 |
| S764P-K773E | 6.73E+07 | 5.15E−03 | 7.65E−11 |
| WT | 7.33E+06 | 1.15E−03 | 1.57E−10 |

TABLE 12

| Mutant | ka (1/Ms) | kd (1/s) | KD (M) |
|---|---|---|---|
| S766Y-K773T | 1.20E+07 | 2.69E−04 | 2.24E−11 |
| S766Y-K773L | 1.79E+07 | 3.45E−04 | 1.92E−11 |
| S766Y-K773R | 1.40E+07 | 4.69E−04 | 3.35E−11 |
| S766Y-K773I | 8.02E+06 | 5.69E−04 | 7.10E−11 |
| S766Y-K773M | 1.97E+07 | 6.59E−04 | 3.35E−11 |
| S766Y-K773V | 1.74E+07 | 8.61E−04 | 4.94E−11 |
| S766Y-K773Q | 2.39E+07 | 9.39E−04 | 3.93E−11 |
| S766Y-K773A | 1.88E+07 | 1.22E−03 | 6.51E−11 |
| S766Y-K773S | 1.75E+07 | 1.38E−03 | 7.85E−11 |
| S766Y-K773G | 6.02E+07 | 1.97E−03 | 3.27E−11 |
| S766Y-K773P | 2.16E+07 | 2.43E−03 | 1.12E−10 |
| S766Y-K773F | 2.05E+07 | 3.24E−03 | 1.58E−10 |
| S766Y-K773W | 2.93E+07 | 3.93E−03 | 1.34E−10 |
| S766Y-K773Y | 2.24E+07 | 4.04E−03 | 1.80E−10 |
| S766Y-K773E | 1.84E+07 | 4.81E−03 | 2.61E−10 |
| S766Y-K773N | 5.15E+07 | 5.07E−03 | 9.84E−11 |
| S766Y-K773H | 5.47E+07 | 6.20E−03 | 1.14E−10 |
| S766Y-K773D | 1.25E+08 | 4.27E−02 | 3.43E−10 |
| WT | 7.33E+06 | 1.15E−03 | 1.57E−10 |

TABLE 13

| Mutant | ka (1/Ms) | kd (1/s) | KD (M) |
|---|---|---|---|
| S764G/S766Y | 1.37E+07 | 2.69E−05 | 1.96E−12 |
| S764V/S766Y | 2.99E+07 | 6.41E−05 | 2.15E−12 |
| S764A/S766Y | 2.98E+07 | 7.21E−05 | 2.42E−12 |
| S764E/S766Y | 1.97E+07 | 7.64E−05 | 3.87E−12 |
| S764P/S766Y | 1.08E+07 | 7.71E−05 | 7.16E−12 |
| S764Y/S766Y | 3.19E+07 | 7.88E−05 | 2.47E−12 |
| S764L/S766Y | 3.52E+07 | 7.99E−05 | 2.27E−12 |
| S764N/S766Y | 1.28E+07 | 8.88E−05 | 6.92E−12 |
| S764R/S766Y | 3.23E+07 | 9.20E−05 | 2.85E−12 |
| S764F/S766Y | 7.68E+06 | 9.36E−05 | 1.22E−11 |
| S764I/S766Y | 1.03E+07 | 9.52E−05 | 9.23E−12 |
| S764W/S766Y | 8.88E+06 | 9.67E−05 | 1.09E−11 |
| S764M/S766Y | 7.15E+06 | 1.03E−04 | 1.44E−11 |
| S764Q/S766Y | 1.19E+07 | 1.09E−04 | 9.18E−12 |
| S764D/S766Y | 3.78E+07 | 1.18E−04 | 3.12E−12 |
| S764T/S766Y | 2.58E+07 | 1.36E−04 | 5.27E−12 |
| S764H/S766Y | 4.56E+07 | 2.92E−04 | 6.39E−12 |
| S764K/S766Y | 1.89E+07 | 8.22E−04 | 4.35E−11 |
| WT | 7.33E+06 | 1.15E−03 | 1.57E−10 |

TABLE 14

| Mutant | ka (1/Ms) | kd (1/s) | KD (M) |
|---|---|---|---|
| S764P-L765H-S766I | 1.56E+06 | 6.60E−05 | 4.24E−11 |
| S764P-L765V-S766I | 5.62E+07 | 1.16E−04 | 2.07E−12 |
| S764P-L765M-S766I | 5.69E+07 | 1.37E−04 | 2.41E−12 |
| S764P-L765W-S766I | 1.11E+06 | 1.46E−04 | 1.32E−10 |
| S764P-L765Q-S766I | 1.15E+06 | 2.86E−04 | 2.48E−10 |
| S764P-L765K-S766I | 6.88E+07 | 1.50E−04 | 2.18E−11 |
| S764P-L765Y-S766I | 5.17E+07 | 1.90E−03 | 3.67E−11 |
| S764P-L765T-S766I | 1.15E+08 | 3.31E−03 | 2.87E−11 |
| S764P-L765I-S766I | 6.34E+06 | 1.03E−02 | 1.62E−09 |
| S764P-L765G-S766I | 5.04E+07 | 1.22E−02 | 2.41E−10 |
| S764P-L765R-S766I | 7.96E+07 | 1.73E−02 | 2.18E−10 |
| S764P-L765E-S766I | 1.03E+06 | 5.50E−02 | 5.36E−08 |
| S764P-L765F-S766I | N/D | | |
| S764P-L765N-S766I | N/D | | |
| S764P-L765D-S766I | N/D | | |
| S764P-L765P-S766I | N/D | | |
| S764P-L765S-S766I | N/D | | |
| S764P-L765A-S766I | N/D | | |

N/D: Binding was present, but accurate kinetic parameters could not be determined

TABLE 15

| Mutant | ka (1/Ms) | kd (1/s) | KD (M) |
|---|---|---|---|
| dupS764/S764P/S766I | 6.23E+06 | 1.59E−03 | 2.55E−10 |
| dupS764/S764P/S766I | 1.25E+07 | 2.50E−03 | 1.99E−10 |
| dS764-dL765-S766I | | | |
| dS764-dL765-S766Y | N/D | | |
| delS764-S766Y | 6.20E+06 | 2.07E−04 | 3.34E−11 |
| delS764-S766W | 6.60E+06 | 3.15E−04 | 4.78E−11 |
| delS764-S766L | 6.21E+06 | 5.85E−04 | 9.42E−11 |
| delS764-S766M | 7.25E+06 | 7.26E−04 | 1.00E−10 |
| delS764-S766I | 7.09E+06 | 8.27E−04 | 1.17E−10 |
| delS764-S766S | 7.30E+06 | 8.46E−04 | 1.16E−10 |

N/D: Binding was present, but accurate kinetic parameters could not be determined

TABLE 16

PH 5.5

| Mutant | ka (1/Ms) | kd (1/s) | KD (M) |
|---|---|---|---|
| S764P-S766W | 2.77E+05 | 4.75E−05 | 1.72E−10 |
| S764P-S766M | 3.14E+05 | 9.16E−05 | 2.92E−10 |
| S764P-S766L | 4.45E+05 | 1.04E−04 | 2.34E−10 |
| WT | 2.03E+06 | 3.88E−02 | 1.91E−08 |
| S764P-S766I | N/D | | |
| S764P-S766Y | N/D | | |
| S764P-S766H | N/D | | |

N/D: Binding was present, but accurate kinetic parameters could not be determined

TABLE 17

S766W, L809X mutants were X is one of the remaining genetic encoded amino acids, excluding cysteine

| Mutant | ka (1/Ms) | kd (1/s) | KD (M) |
|---|---|---|---|
| S766W-L809A | 4.45E+06 | 1.15E−03 | 2.58E−10 |
| S766W-L809D | 4.46E+06 | 1.90E−03 | 4.25E−10 |
| S766W-L809E | 5.84E+06 | 1.55E−03 | 2.65E−10 |
| S766W-L809F | 3.26E+06 | 7.44E−04 | 2.28E−10 |
| S766W-L809G | 6.21E+06 | 2.26E−03 | 3.63E−10 |
| S766W-L809H | 2.87E+06 | 1.14E−03 | 3.97E−10 |
| S766W-L809I | 5.23E+06 | 5.41E−04 | 1.03E−10 |
| S766W-L809K | 7.00E+06 | 1.53E−03 | 2.19E−10 |
| S766W-L809M | 4.99E+06 | 5.81E−04 | 1.17E−10 |
| S766W-L809N | 6.15E+06 | 2.27E−03 | 3.69E−10 |
| S766W-L809P | NB | NB | NB |
| S766W-L809Q | 5.33E+06 | 1.13E−03 | 2.12E−10 |
| S766W-L809R | 6.07E+06 | 2.13E−03 | 3.52E−10 |

TABLE 17-continued

S766W, L809X mutants were X is one of the remaining genetic encoded amino acids, excluding cysteine

| Mutant | ka (1/Ms) | kd (1/s) | KD (M) |
|---|---|---|---|
| S766W-L809S | 6.54E+06 | 1.44E−03 | 2.20E−10 |
| S766W-L809T | 8.72E+06 | 1.41E−03 | 1.61E−10 |
| S766W-L809V | 7.70E+06 | 9.40E−04 | 1.22E−10 |
| S766W-L809W | 4.81E+06 | 3.12E−03 | 6.48E−10 |
| S766W-L809Y | 6.77E+06 | 3.39E−03 | 5.00E−10 |
| vWF WT | 4.98E+06 | 8.86E−04 | 1.78E−10 |

TABLE 18

S766W, S806X mutants were X is one of the remaining genetic encoded amino acids, excluding cysteine

| Mutant | ka (1/Ms) | kd (1/s) | KD (M) |
|---|---|---|---|
| S766W-S806A | 4.84E+06 | 3.76E−04 | 7.78E−11 |
| S766W-S806D | 4.20E+06 | 6.88E−04 | 1.64E−10 |
| S766W-S806E | 5.93E+06 | 1.29E−03 | 2.17E−10 |
| S766W-S806F | NB | NB | NB |
| S766W-S806G | 5.46E+06 | 1.34E−03 | 2.45E−10 |
| S766W-S806H | 8.90E+06 | 8.28E−04 | 9.30E−11 |
| S766W-S806I | 1.58E+06 | 4.47E−04 | 2.83E−10 |
| S766W-S806K | N/D | | |
| S766W-S806L | NB | NB | NB |
| S766W-S806M | 2.05E+06 | 8.72E−04 | 4.25E−10 |
| S766W-S806N | 3.84E+06 | 5.85E−04 | 1.52E−10 |
| S766W-S806P | 4.26E+06 | 5.66E−04 | 1.33E−10 |
| S766W-S806Q | 4.33E+06 | 1.76E−03 | 4.07E−10 |
| S766W-S806R | 8.28E+06 | 1.07E−02 | 1.29E−09 |
| S766W-S806T | 5.25E+06 | 6.54E−04 | 1.25E−10 |
| S766W-S806V | 4.17E+06 | 6.19E−04 | 1.49E−10 |
| S766W-S806W | NB | NB | NB |
| S766W-S806Y | NB | NB | NB |
| vWF WT | 4.98E+06 | 8.86E−04 | 1.78E−10 |

N/D: Binding was present, but accurate kinetic parameters could not be determined

TABLE 19

S766Y, P769X mutants were X is one of the remaining genetic encoded amino acids, excluding cysteine

| Mutant | ka (1/Ms) | kd (1/s) | KD (M) |
|---|---|---|---|
| S766Y-P769A | 4.90E+06 | 5.19E−04 | 1.06E−10 |
| S766Y-P769D | 4.63E+06 | 7.63E−04 | 1.65E−10 |
| S766Y-P769E | 4.42E+06 | 4.14E−04 | 9.36E−11 |
| S766Y-P769F | 5.54E+06 | 4.27E−04 | 7.72E−11 |
| S766Y-P769G | 3.70E+06 | 7.83E−04 | 2.12E−10 |
| S766Y-P769H | 5.16E+06 | 4.17E−04 | 8.09E−11 |
| S766Y-P769I | NB | NB | NB |
| S766Y-P769K | 6.31E+06 | 3.83E−04 | 6.07E−11 |
| S766Y-P769L | 6.44E+06 | 5.90E−04 | 9.17E−11 |
| S766Y-P769M | 4.75E+06 | 5.11E−04 | 1.08E−10 |
| S766Y-P769N | 1.60E+07 | 5.20E−04 | 3.25E−11 |
| S766Y-P769Q | NB | NB | NB |
| S766Y-P769R | 6.55E+06 | 2.95E−04 | 4.50E−11 |
| S766Y-P769S | 4.51E+06 | 5.11E−04 | 1.13E−10 |
| S766Y-P769T | 5.11E+06 | 5.00E−04 | 9.79E−11 |
| S766Y-P769V | 6.65E+06 | 5.65E−04 | 8.49E−11 |
| S766Y-P769W | 4.77E+06 | 4.21E−04 | 8.82E−11 |
| S766Y-P769Y | 4.68E+06 | 3.96E−04 | 8.47E−11 |
| vWF WT | 4.98E+06 | 8.86E−04 | 1.78E−10 |

TABLE 20

S766Y, R768X mutants were X is one of the remaining genetic encoded amino acids, excluding cysteine

| Mutant | ka (1/Ms) | kd (1/s) | KD (M) |
|---|---|---|---|
| S766Y-R768A | 6.99E+06 | 1.48E−03 | 2.12E−10 |
| S766Y-R768D | 4.94E+06 | 4.48E−03 | 9.08E−10 |
| S766Y-R768E | 5.65E+06 | 3.22E−03 | 5.69E−10 |
| S766Y-R768F | 6.51E+06 | 1.82E−03 | 2.79E−10 |
| S766Y-R768G | 3.20E+06 | 1.02E−03 | 3.20E−10 |
| S766Y-R768H | 4.02E+06 | 6.90E−04 | 1.72E−10 |
| S766Y-R768I | 5.03E+06 | 8.99E−04 | 1.79E−10 |
| S766Y-R768K | 3.83E+06 | 4.17E−04 | 1.09E−10 |
| S766Y-R768L | 4.24E+06 | 5.48E−04 | 1.29E−10 |
| S766Y-R768M | 4.08E+06 | 8.01E−04 | 1.96E−10 |
| S766Y-R768N | 4.18E+06 | 7.98E−04 | 1.91E−10 |
| S766Y-R768P | 6.71E+06 | 1.43E−03 | 2.13E−10 |
| S766Y-R768Q | 3.48E+06 | 6.06E−04 | 1.74E−10 |
| S766Y-R768S | 5.33E+06 | 1.29E−03 | 2.43E−10 |
| S766Y-R768T | 5.59E+06 | 1.43E−03 | 2.56E−10 |
| S766Y-R768V | 4.51E+06 | 9.18E−04 | 2.03E−10 |
| S766Y-R768W | 4.42E+06 | 9.40E−04 | 2.13E−10 |
| S766Y-R768Y | 6.74E+06 | 1.87E−03 | 2.77E−10 |
| vWF WT | 4.98E+06 | 8.86E−04 | 1.78E−10 |

TABLE 21

Dimers Binding to FVIII (pH 7.3)

| Mutant | ka (1/Ms) | kd (1/s) | KD (M) |
|---|---|---|---|
| S764P-S766I | 1.01E+07 (±3.41E6) | 5.00E−05 (±3.37E−6) | 3.96E−12 (±2.6E−13) |
| S764P-S766W | 1.24E+07 (±7.28E5) | 6.21E−05 (±2.52E−6) | 4.96E−12 (±1.9E−13) |
| S766Y | 1.03E+07 (±3.01E6) | 2.36E−04 (±4.27E−5) | 2.51E−11 (±3.83E−12) |
| S764E-S766Y | 7.75E+06 (±1.71E6) | 2.36E−04 (±2.90E−5) | 3.25E−11 (±4.57E−12) |
| S764I-S766W | 7.54E+06 (±5.15E5) | 2.41E−04 (±5.05E−6) | 3.25E−11 (±2.25E−12) |
| S764G-S766Y | 1.19E+07 (±9.1E5) | 2.63E−04 (±1.41E−5) | 2.29E−11 (±3.42E−12) |
| S766Y-P769R | 1.18E+07 (±4.1E5) | 2.75E−04 (±1.71E−5) | 2.32E−11 (±9.54E−13) |
| S766Y-P769K | 1.09E+07 (±1.37E6) | 2.85E−04 (±2.08E−5) | 2.68E−11 (±1.55E−12) |
| S766W-S806A | 8.88E+06 (±1.11E6) | 3.00E−04 (±1.9E−5) | 3.54E−11 (±4.37E−12) |
| S764Y-S766Y | 1.14E+07 (±1.71E6) | 3.34E−04 (±2.7E−5) | 3.07E−11 (±3.53E−12) |
| S766Y-S769N | 1.21E+07 (±1.11E6) | 3.48E−04 (±3.21E−5) | 2.89E−11 (±1.75E−12) |
| S764A | 1.26E+07 (±1.38E6) | 6.38E−04 (±3.24E−5) | 5.14E−11 (±2.81E−12) |
| WT | 1.89E+07 (±2.68E6) | 1.47E−03 (±8.92E−5) | 8.25E−11 (±7.94E−12) |

TABLE 22

Dimers Binding to FVIII (pH 5.5)

| Mutant | ka (1/Ms) | kd (1/s) | KD (M) |
|---|---|---|---|
| S764P-S766I | 3.10E+06 (±3.05E5) | 1.81E−03 (±6.34E−5) | 5.98E−10 (±4.93E−11) |
| S764P-S766W | 3.02E+06 (±2.39E5) | 1.88E−03 (±1.78E−5) | 6.37E−10 (±5.75E−11) |
| S764E-S766Y | 2.43E+06 (±1.6E5) | 2.71E−03 (±9.8E−5) | 1.12E−09 (±5.29E−11) |
| S764Y-S766Y | 3.22E+06 (±1.24E5) | 3.45E−03 (±9.01E−5) | 1.07E−09 (±4.67E−11) |
| S766Y-P769R | 4.66E+06 (±1.47E5) | 6.54E−03 (±2.02E−4) | 1.40E−09 (±2.29E−11) |
| S764I-S766W | 3.28E+06 (±1.22E5) | 7.24E−03 (±2.89E−4) | 2.21E−09 (±5.78E−11) |
| S766Y-P769K | 4.14E+06 (±2.95E5) | 7.40E−03 (±3.9E−4) | 1.79E−09 (±1.27E−10) |
| S766Y | 3.50E+06 (±2.5E5) | 7.40E−03 (±2.12E−3) | 2.92E−09 (±1.38E−10) |
| S766Y-S769N | 2.05E+06 (±2.02E5) | 1.02E−02 (±7.84E−4) | 5.01E−09 (±2.67E−10) |
| S766W-S806A | 8.13E+05 (±2.83E5) | 1.40E−02 (±6.74E−4) | 1.43E−08 (±2.38E−9) |
| S764G-S766Y | 2.66E+06 (±4.55E5) | 1.85E−02 (±1.12E−3) | 7.53E−09 (±1.15E−9) |
| S764A | 2.25E+06 (±1.42E6) | 4.01E−02 (±2.54E−3) | 5.26E−08 (±3.33E−9) |
| WT | 1.37E+06 (±2.44E5) | 4.26E−02 (±3.9E−3) | 3.54E−08 (±2.89E−9) |

Example 3

In an extension of the work described in PCT/AU2015/050369 further mutations and combinations of mutations were investigated with an emphasis on modifications in the D3 domain. In these experiments a recombinant form of FVIII was used. This FVIII is described in Zollner et al 2013, Thrombosis Research, 132:280-287.

Methods

Plasmid constructs encoding vWF(763-1242)-HSA and containing the single, double or triple mutations listed in Table 23 were used to generate purified vWF-HSA dimer proteins using the methods described in Example 2. Detailed kinetic analysis at pH7 was set up for the top candidates, including controls.

Mouse anti-HSA antibody was immobilized on a CM5 chip using standard NHS/EDC coupling chemistry. Typically, the immobilization level was about 14,000 RU. Each Dimer mutant of vWF-HSA was captured on a single spot in each flow cell for 2 minutes at various concentrations ranging from 0.1-1 μg/ml. Capture levels ranged from 100-200 RU. An adjacent spot in which anti-HSA was immobilized, but no vWF-HSA captured was used as a reference. Capture was performed every cycle, before FVIII binding analysis. In initial experiments, Factor VIII was injected at random and in duplicate over all spots and all flow cells in use at 5, 1 and 1.25 nM. The results of this analysis are set out in Table 23.

TABLE 23

Screen at pH 7: affinities and kinetic rates of Factor VIII for various mutant D'D3-HSA dimer proteins ranked from strongest to weakest affinities.

| Protein | ka (1/Ms) | kd (1/s) | KD (M) | Sample size |
|---|---|---|---|---|
| V1083A, S764P, S766W | 6.15E+06 | 1.17E−04 | 1.90E−11 | n = 1 |
| V1083A, S764G, S766Y | 6.19E+06 | 1.86E−04 | 3.01E−11 | n = 2 |
| N1011S, V1083A, K1181E | 5.31E+06 | 4.30E−04 | 8.10E−11 | n = 1 |
| V1083A | 5.51E+06 | 5.39E−04 | 9.78E−11 | n = 1 |
| S1042T | 4.39E+06 | 4.69E−04 | 1.07E−10 | n = 2 |
| V805A, Q1158L | 4.26E+06 | 6.32E−04 | 1.49E−10 | n = 2 |
| K912E, T1088S | 5.17E+06 | 8.00E−04 | 1.55E−10 | n = 2 |
| L781P | 4.27E+06 | 6.99E−04 | 1.64E−10 | n = 2 |
| WT | 4.83E+06 | 1.08E−03 | 2.23E−10 | n = 1 |
| R960G | 4.09E+06 | 1.11E−03 | 2.72E−10 | n = 2 |

WT = wildtype

Example 4

Detailed Kinetic Analysis

Subsequent experiments were conducted where detailed kinetic analysis at pH7 was set up for the top two candidates, including controls. Factor VIII was injected at 1, 0.5, 0.25, 0.125 and 0.06 nM. In a similar manner detailed kinetic analysis on the top two candidates, including controls was set up at pH5.5 where Factor VIII was injected at various concentrations that best suited the interaction.

Throughout all experiments buffer blanks were also injected over all captured proteins. The association and dissociation of Factor VIII was monitored for 3 minutes respectively during the "screening" experiment. The association of CSL627 was monitored for 5 minutes and dissociation was monitored for 20 and 60 minutes during the "detailed kinetic analysis" experiments at neutral pH. At pH 5.5 the association and dissociation of Factor VIII was monitored for various time frames that best suited the interaction.

Post the dissociation period the surface was regenerated with a 45 second injection of 25 mM Glycine pH2.6. Running buffer throughout was 10 mM HEPES, 150 mM NaCl, 10 mM Na Citrate, 2.5 mM $CaCl_2$), 0.1% BSA, pH7.3 and pH5.5, while the flow rate was 30 µl/min. Each interaction was measured at least 2 times (n=2) at 37° C.

Figure 2:
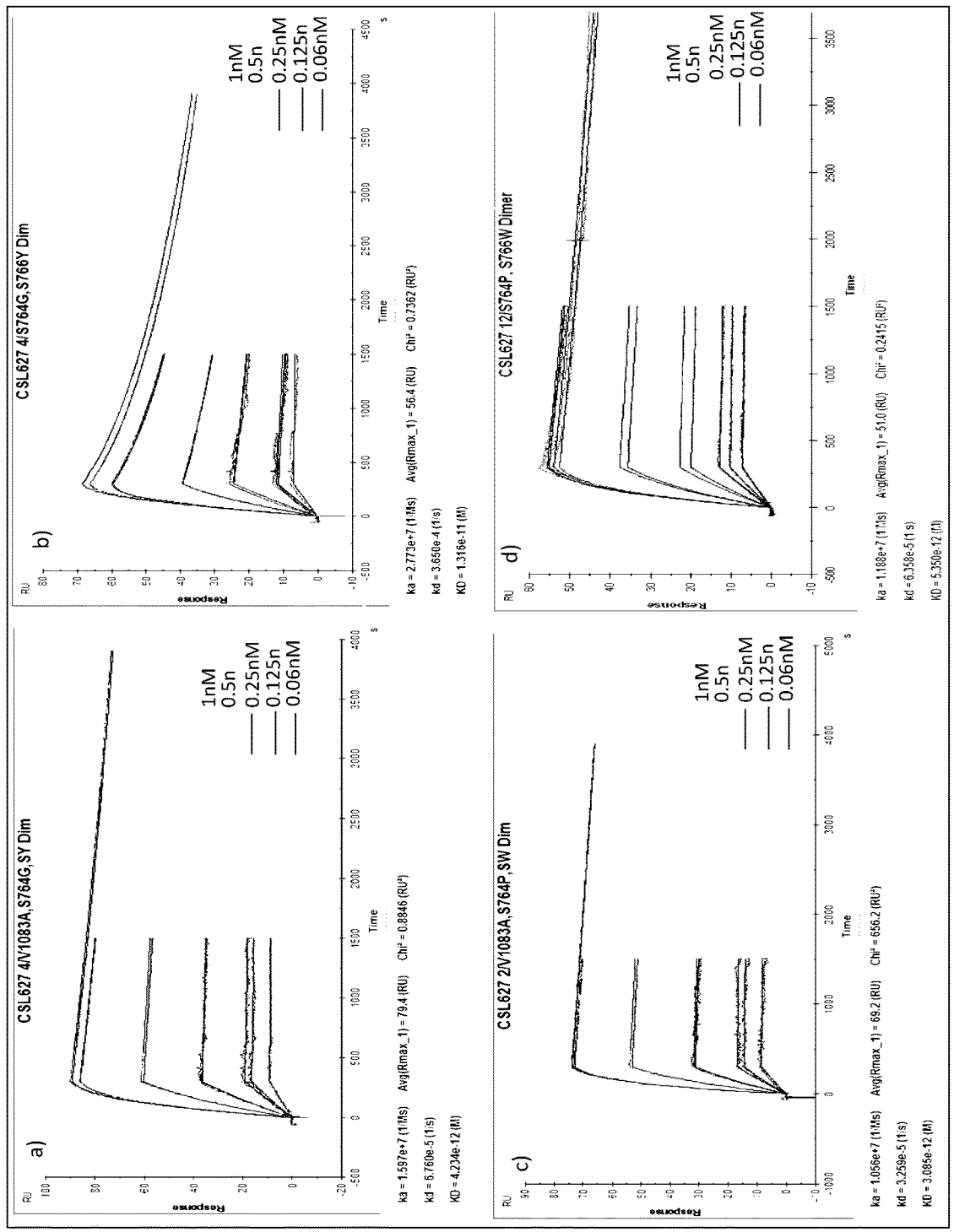
FIG. 2: Sample sensorgrams showing detailed kinetics of CSL627 for two mutant D'D3-HSA candidates at pH7. a) Factor VIII binding D'D3-HSA with mutations: V1083A, S764G, S766Y; b) Factor VIII binding D'D3-HSA with mutations: S764G, S766Y; c) Factor VIII binding D'D3-HSA with mutations: V1083A, S764P, S766W; d) Factor VIII binding D'D3-HSA S764P, S766W.
Figure 3:
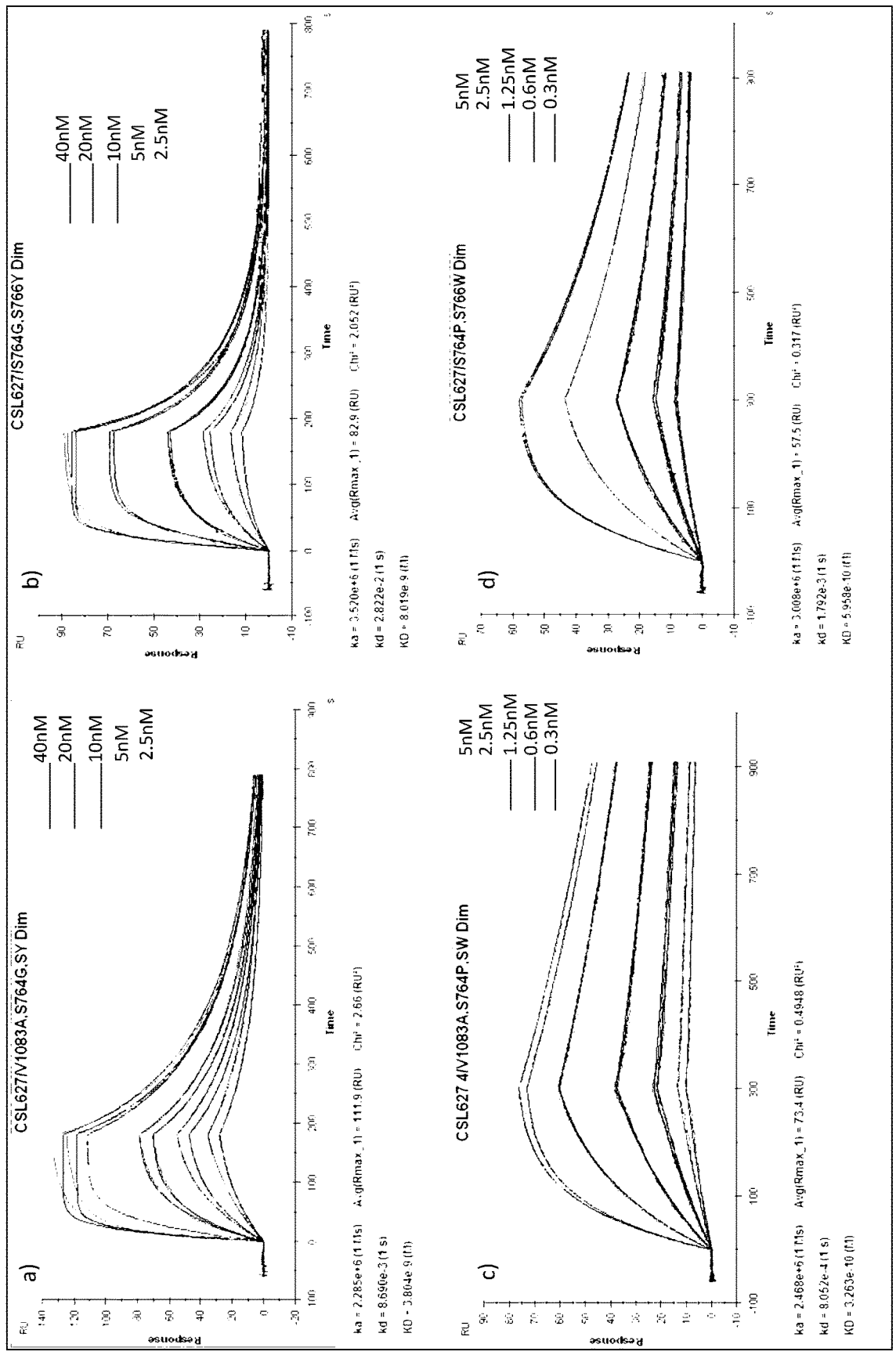
FIG. 3: Sample sensorgrams showing detailed kinetics of Factor VIII for two mutant D'D3-HSA candidates at pH5.5 a) Factor VIII binding D'D3-HSA with mutations: V1083A, S764G, S766Y; b) Factor VIII binding D'D3-HSA with mutations: S764G, S766Y. c) Factor VIII binding D'D3-HSA with mutations: V1083A, S764P, S766W d) Factor VIII binding D'D3-HSA S764P, S766W.

Responses for binding to the reference spot were subtracted from those of the vWF-HSA captured spots. Responses from blank injections were then subtracted from those of all other samples to produce double-referenced sensorgrams. Double referenced sensorgrams were fitted to a 1:1 kinetic model, including a term for mass transport limitation. Association and dissociation rates were fitted globally and Rmax fitted locally. The results are set out in Tables 24 and 25 and shown in FIGS. 1-3.

TABLE 24

Detailed Kinetics at pH 7: affinities and kinetic rates of Factor VIII for mutant D'D3-HSA dimers.

| Protein | ka (1/Ms) | kd (1/s) | KD (M) | Sample Size |
|---|---|---|---|---|
| V1083A, S764P, S766W (PWA) | 1.15E+07 | 3.84E−05 | 3.36E−12 | n = 4 |
| V1083A, S764G, S766Y (GYA) | 1.63E+07 | 7.30E−05 | 4.50E−12 | n = 2 |
| S764G, S766Y (GY) | 2.95E+07 | 3.65E−04 | 1.25E−11 | n = 3 |
| WT* | 1.06E+07 | 8.46E−04 | 8.03E−11 | n = 2 |

WT = wildtype

TABLE 25

Detailed Kinetics at pH 5.5: affinities and kinetic rates of Factor VIII for mutant D'D3-HSA dimers

| Protein | ka (1/Ms) | kd (1/s) | KD (M) | Sample Size |
|---|---|---|---|---|
| V1083A, S764P, S766W | 2.51E+06 | 8.44E−04 | 3.42E−10 | n = 4 |
| S764P, S766W | 2.94E+06 | 1.80E−03 | 6.14E−10 | n = 2 |
| V1083A, S764G, S766Y | 2.05E+06 | 8.12E−03 | 4.05E−09 | n = 4 |
| S764G, S766Y | 2.57E+06 | 2.50E−02 | 1.13E−08 | n = 3 |

Example 5

Further Kinetic Analysis

Method in Brief:

Additional mutation combinations were then generated using the same experimental approaches and a detailed kinetic analysis performed.

Mouse anti-HSA antibody was immobilized on a CM5 chip using standard NHS/EDC coupling chemistry. Typically, the immobilization level was about 14,000 RU. Each Dimer mutant of D'D3-HSA was captured on a single spot in each flow cell for 2 minutes at various concentrations ranging from 0.2-0.7 µg/ml. Capture levels ranged from 50-250 RU. An adjacent spot in which anti-HSA was immobilized, but no D'D3-HSA captured was used as a reference. Capture was performed every cycle, before FVIII (CSL627) binding analysis.

CSL627 was injected at random and in duplicate over all spots in all flow cells. At neutral pH CSL627 was injected at 1, 0.5, 0.25, 0.125 and 0.06 nM. The association was monitored for 5 minutes, while the dissociation was monitored for 20 minutes as well as for 1 hour at the 1 nM concentration. Buffer blanks were also injected. At pH5.5 CSL627 was injected at various concentrations and time frames that best suited the interaction taking place.

After the dissociation period the surface was regenerated with a 45 second injection of 25 mM Glycine pH2.6. Running buffer throughout was 10 mM HEPES, 150 mM NaCl, 10 mM Na Citrate, 2.5 mM CaCl2, 0.1% BSA, pH7.3 and pH5.5, while the flow rate was 30 µl/min. Each interaction was measured 4 times (n=4) at 37° C.

Responses for binding to the reference spot were subtracted from those of the vWF-HSA captured spots. Responses from blank injections were then subtracted from those of all other samples to produce double-referenced sensorgrams. Double referenced sensorgrams were fitted to a 1:1 kinetic model, including a term for mass transport limitation. Association and dissociation rates were fitted globally and Rmax fitted locally.

Figure 4:
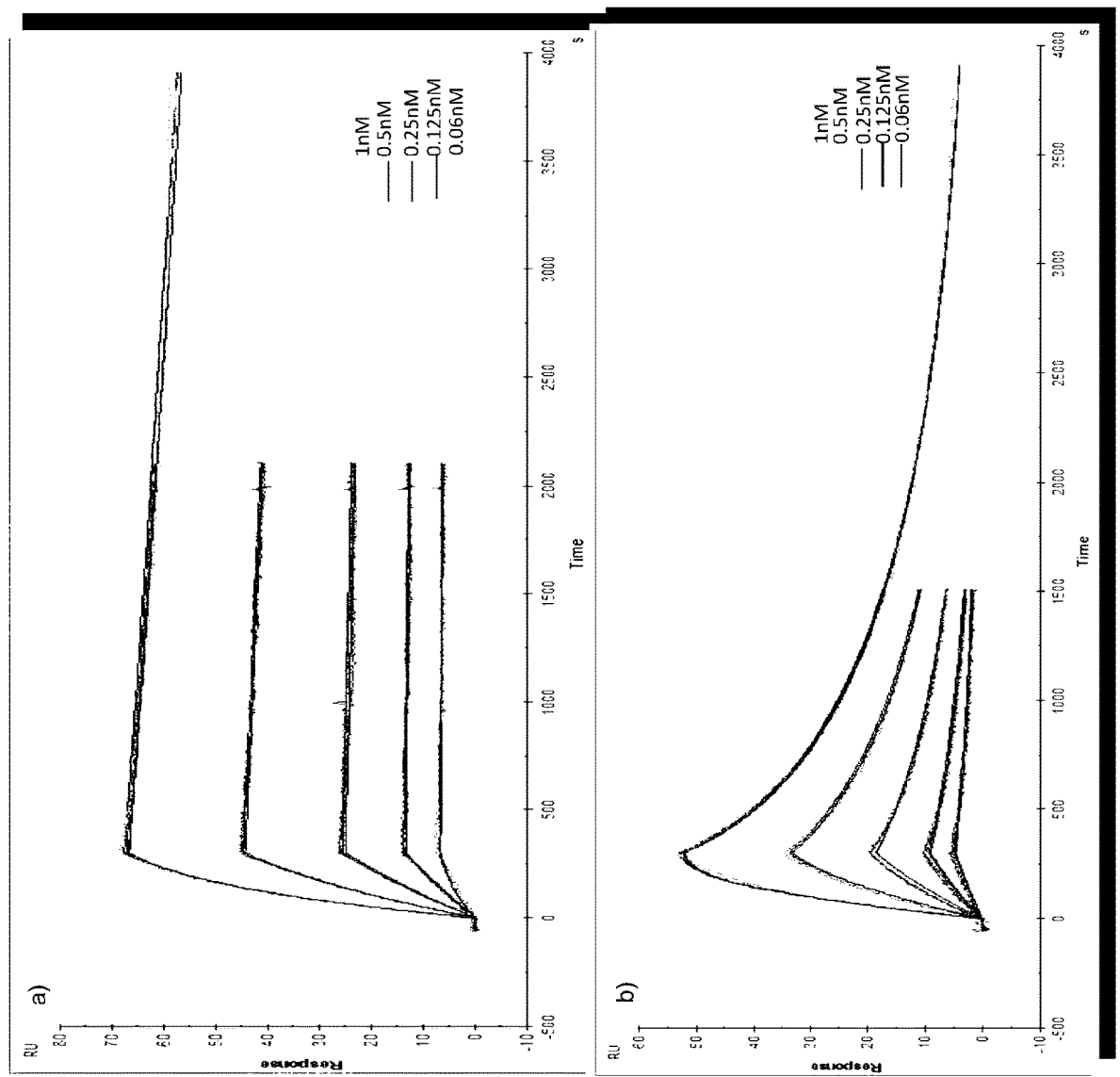
FIG. 4: a) CSL627 binding D'D3-HSA Dimer with mutations: V1083A, S764E, S766Y at neutral pH; b) CSL627 binding wildtype D'D3-HSA Dimer at neutral pH.
Figure 5:
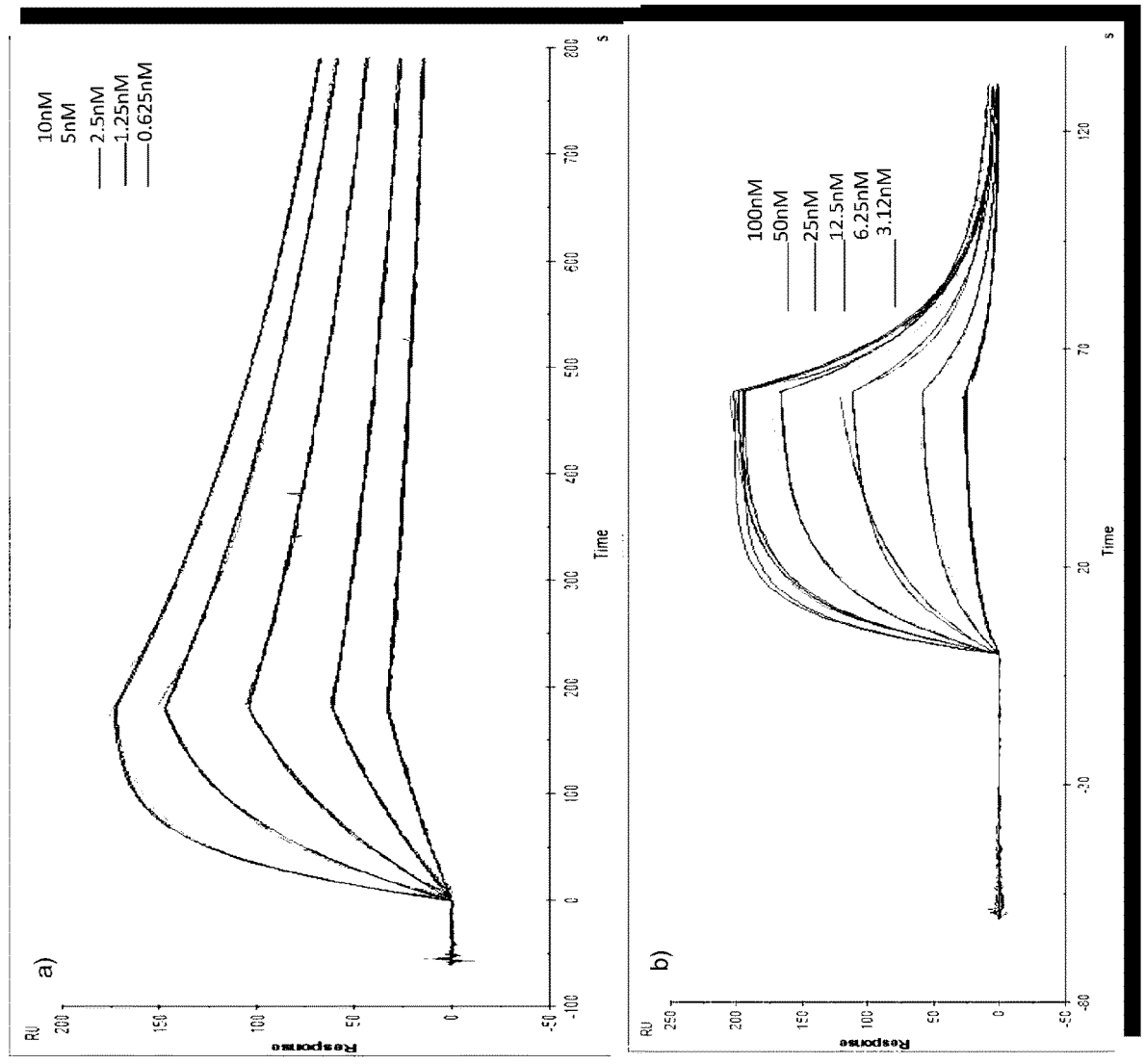
FIG. 5: a) CSL627 binding D'D3-HSA Dimer with mutations: V1083A, S764E, S766Y b) CSL627 binding wildtype D'D3-HSA Dimer at pH5.5.

The results are set out in Tables 26 and 27 and FIGS. 4 and 5.

TABLE 26

Detailed Kinetics at pH 7: affinities and kinetic rates of CSL627 (Factor VIII) binding to mutant D'D3-HSA dimers.

| vWF D'D3-HSA Dimer | ka (1/Ms) | kd (1/s) | KD (M) | Sample Size (n) |
|---|---|---|---|---|
| S764G, S766Y, V1083A | 1.33E+07 ± 1.58E+06 | 6.44E−05 ± 3.39E−06 | 4.96E−12 ± 3.31E−13 | n = 4 |
| S764E, S766Y, V1083A | 8.59E+06 ± 4.21E+05 | 4.77E−05 ± 3.59E−06 | 5.65E−12 ± 5.82E−13 | n = 5 |
| S766Y, V1083A | 1.47E+07 ± 1.2E+06 | 8.88E−05 ± 7.15E−06 | 6.05E−12 ± 2.53E−13 | n = 4 |
| S764E, V1083A | 1.77E+07 ± 1.74E+06 | 2.07E−04 ± 3.04E−05 | 1.16E−11 ± 1.03E−12 | n = 4 |
| S764G, V1083A | 1.89E+07 ± 7.01E+05 | 3.59E−04 ± 8.59E−06 | 1.90E−11 ± 3.74E−13 | n = 4 |
| Wildtype | 2.31E+07 ± 3.03E−06 | 2.22E−03 ± 1.02E−04 | 9.88E−11 ± 9.8E−12 | n = 4 |

TABLE 28

Detailed Kinetics at pH 5.5: affinities and kinetic rates of CSL627 binding to mutant D'D3-HSA dimers.

| vWF D'D3-HSA Dimer | ka (1/Ms) | kd (1/s) | KD (M) | Sample Size (n) |
|---|---|---|---|---|
| S764E, S766Y, V1083A | 3.61E+06 ± 2.12E+05 | 1.89E−03 ± 6.42E−05 | 5.35E−10 ± 2.64E−11 | n = 4 |
| S766Y, V1083A | 4.04E+06 ± 4.64E+05 | 9.55E−03 ± 7.47E−04 | 2.38E−09 ± 8.42E−11 | n = 3 |
| S764G, S766Y, V1083A | 6.81E+06 ± 3.77E+06 | 1.56E−02 ± 6.27E−03 | 2.93E−09 ± 4.70E−10 | n = 4 |
| S764E, V1083A | 2.50E+06 ± 1.67E+05 | 2.07E−02 ± 7.8E−04 | 8.32E−09 ± 3.12E−10 | n = 4 |
| S764G, V1083A | 9.08E+05 ± 3.54E+04 | 7.44E−02 ± 1.37E−03 | 8.24E−08 ± 4.18E−09 | n = 4 |
| Wildtype | 6.48E+05 ± 2.32E+04 | 7.91E−02 ± 9.81E−03 | 1.22E−07 ± 1.36E−08 | n = 3 |

Example 6

PK Analysis and Impact on FVIII Half-Life

Methods

A stable CHO derived cell line expressing the Hu vWF D'D3-FP S764E; S766Y variant was generated using standard experimental methods. Material was produced from the stable cell line in a 10 L bioreactor and vWF D'D3-FP S764E; S766Y dimer purified as previously described.

To assess the relative impact of wild-type and the vWF D'D3-FP S764E; S766Y variant on FVIII levels, CD Rats (3 animals/group) were given a combination of recombinant FVIII (CSL627 at 200 IU/kg) and vWF-FP proteins at the doses shown in Table 9. Plasma samples were taken at 0, 3, 8, 24, 48, 56 and 72 hours following iv administration and FVIII levels determined using an Asserachrom FVIII:Ag ELISA. This data was then used to determine the FVIII Half-life and Mean Residence Times given in Table 29.

TABLE 29

PK Analysis: FVIII Half-life and Mean Residence time following co administration of recombinant FVIII and D'D3-HSA dimers

| Treatment group (readout based on Asserachrom FVIII: Ag ELISA) | Mean Residence Time (hrs) | T ½ (hrs) |
|---|---|---|
| CSL627-rVIII-SingleChain, 200 IU/kg | 10.3 | 7.1 |
| rD'D3-FP S764E; S766Y 0.09 mg/kg + CSL627 200 IU/kg | 13.1 | 9.1 |
| rD'D3-FP S764E; S766Y 0.3 mg/kg + CSL627 200 IU/kg | 17.8 | 12.3 |
| rD'D3-FP S764E; S766Y 0.9 mg/kg + CSL627 200 IU/kg | 22.6 | 15.6 |
| rD'D3-FP wild type 1.0 mg/kg + CSL627 200 IU/kg | 14.1 | 10.1 |
| rD'D3-FP wild type 3.0 mg/kg + CSL627 200 IU/kg | 18.4 | 12.7 |
| rD'D3-FP wild type 10.0 mg/kg + CSL627 200 IU/kg | 26.2 | 18.1 |

CONCLUSION

From the initial screen D'D3-HSA with mutations: S764P, S766W, V1083A (referred as PWA mutant) and S764G, S766Y, V1083A (referred to as GYA mutant) appeared to have the strongest affinity and slowest off rate for Factor VIII.

At neutral pH, vWF D'D3-HSA mutant dimers with the most improved affinity and off rate for CSL627 (Factor VIII) are S764G/S766Y/V1083A (GYA), S764E/S766Y/V1083A (EYA) and S766Y/V1083A (YA) with a 5 pM KD and a $10^{-5}$ l/s off rate. This is about a 20 fold improvement in affinity and 40 fold improvement in off rate compared to the wildtype dimer.

At acidic pH, the vWF D'D3-HSA mutant dimer with the most improved affinity and off rate for CSL627 was EYA with a 500 pM KD and a $10^{-3}$ l/s off rate. Based on this, the improvement in affinity and off rate for EYA is about 100 fold and at least 10 fold respectively compared to the wildtype dimer.

EYA Dimer appeared to have similar kinetic rates and affinity for CSL627 as 5764P/57661 at both neutral and acidic pH.

The invention claimed is:

1. A polypeptide comprising a truncated von Willebrand Factor (VWF), wherein the truncated VWF comprises an amino acid sequence selected from the group consisting of SEQ ID NOs:5-12 and 17, and wherein the truncated VWF binds Factor VIII (FVIII).

2. The polypeptide of claim 1, wherein the truncated VWF binds to FVIII with an off rate lower than a reference polypeptide comprising SEQ ID NO:3.

3. The polypeptide of claim 2, wherein the truncated VWF binds to FVIII with an off rate at least 5 fold lower than the reference polypeptide.

4. The polypeptide of claim 3, wherein the truncated VWF binds to FVIII with an off rate at least 10 fold lower than the reference polypeptide.

5. The polypeptide of claim 2, wherein the truncated VWF binds to FVIII with a dissociation constant (KD) at least 5 fold lower than the reference polypeptide.

6. The polypeptide of claim 5, wherein the truncated VWF binds to FVIII with an off rate at least 10 fold lower than the reference polypeptide.

7. The polypeptide of claim 1, wherein the truncated VWF comprises amino acids 1243 to 1247 of SEQ ID NO:2 or amino acids 1243 to 1270 of SEQ ID NO:2.

8. The polypeptide of claim 1, wherein the truncated VWF lacks amino acids 1243 to 1247 of SEQ ID NO:2 or amino acids 1243 to 2813 of SEQ ID NO:2.

9. The polypeptide of claim 1, further comprising a half-life extending moiety.

10. The polypeptide of claim 9, wherein the half-life extending moiety is a heterologous amino acid sequence fused to the truncated VWF.

11. The polypeptide of claim 10, wherein the heterologous amino acid sequence comprises a polypeptide selected from the group consisting of immunoglobulin constant regions and portions thereof, transferrin and fragments thereof, the C-terminal peptide of human chorionic gonadotropin, solvated random chains with large hydrodynamic volume known as XTEN, homo-amino acid repeats (HAP), proline-alanine-serine repeats (PAS), albumin, afamin, alpha-fetoprotein, Vitamin D binding protein, polypeptides capable of binding under physiological conditions to albumin or immunoglobulin constant regions, and combinations thereof.

12. The polypeptide of claim 10, wherein the heterologous amino acid sequence comprises an Fc fragment.

13. The polypeptide of claim 10, wherein the heterologous amino acid sequence comprises albumin.

14. The polypeptide of claim 13, wherein the N-terminus of the albumin is fused to the C-terminus of the truncated VWF, either directly or via a spacer.

15. The polypeptide of claim 14, wherein 1 to 5 amino acids at the natural C-terminus of the truncated VWF have been deleted.

16. The polypeptide of claim 9, wherein the half-life extending moiety is conjugated to the polypeptide.

17. The polypeptide of claim 16, wherein the half-life extending moiety is selected from the group consisting of hydroxyethyl starch (HES), polyethylene glycol (PEG), polysialic acids (PSAs), elastin-like polypeptides, heparosan polymers, hyaluronic acid, albumin binding ligands, and combinations thereof.

18. The polypeptide of claim 16, wherein the half-life extending moiety is a fatty acid chain.

19. The polypeptide of claim 1, wherein the polypeptide is a glycoprotein comprising N-glycans, and wherein at least 75% of the N-glycans comprise, on average, at least one sialic acid moiety.

20. The polypeptide of claim 19, wherein at least 60% of the N-glycans comprise, on average, at least one α-2,6-sialic acid moiety.

21. The polypeptide of claim 1, wherein the polypeptide is a glycoprotein comprising N-glycans, and wherein at least 85% of the N-glycans comprise, on average, at least one sialic acid moiety.

22. The polypeptide of claim 1, wherein the polypeptide is a glycoprotein comprising N-glycans, and wherein at least 90% of the N-glycans comprise, on average, at least one sialic acid moiety.

23. The polypeptide of claim 1, wherein the polypeptide is a glycoprotein comprising N-glycans, and wherein at least 95% of the N-glycans comprise, on average, at least one sialic acid moiety.

24. The polypeptide of claim 1, wherein the polypeptide is a dimer.

25. A complex comprising a FVIII molecule and the polypeptide of claim 1.

26. A pharmaceutical composition comprising the polypeptide of claim 1.

27. A method of treating a blood coagulation disorder, comprising administering to a patient in need thereof a pharmaceutically effective amount of the polypeptide of claim 1.

28. The method of claim 27, wherein the blood coagulation disorder is von Willebrand's disease (VWD) or hemophilia A.

29. A method of treating a blood coagulation disorder, comprising administering to a subject in need thereof a pharmaceutically effective amount of the polypeptide of claim 1 and a FVIII,
wherein the subject has endogenous VWF, and
wherein the molar ratio of the polypeptide to the FVIII is greater than 50, and/or the molar ratio of the polypeptide to the endogenous VWF is greater than 0.5.

30. The method of claim 29, wherein the subject is a human.

31. The method of claim 29, wherein the polypeptide is administered intravenously.

32. The method of claim 29, wherein the FVIII and the polypeptide are administered separately.

33. The method of claim 29, wherein the FVIII and the polypeptide are administered simultaneously or sequentially.

34. The method of claim 29, wherein the mean residence time (MRT) of the FVIII is increased by the co-administration of the polypeptide, as compared to a reference treatment in which the polypeptide and the FVIII are administered in equimolar amounts.

35. The method of claim 29, wherein the frequency of administration of the FVIII is reduced as compared to a treatment with the FVIII alone.

36. The method of claim 29, wherein the plasma half-life of the polypeptide is greater than that of the endogenous VWF.

37. The method of claim 36, wherein the plasma half-life of the polypeptide is at least 25% greater than that of the endogenous VWF.

38. A pharmaceutical composition comprising (i) a FVIII and (ii) the polypeptide of claim 1, wherein the molar ratio of the polypeptide to the FVIII is greater than 50.

39. A method for improving the plasma half-life of FVIII, and/or for reducing the frequency of administration of FVIII, comprising administering to a subject in need thereof an effective amount of the polypeptide of claim 1.

40. A method for increasing the half-life of FVIII, comprising mixing the FVIII with the polypeptide of claim 1.

41. A method of treating a blood coagulation disorder, comprising administering to a subject in need thereof an effective amount of the polypeptide of claim 1 and an effective amount of a FVIII, wherein the polypeptide is administered intravenously or subcutaneously, and wherein the FVIII is administered intravenously.

42. The method of claim 41, wherein the MRT of the FVIII is increased by the co-administration of the polypeptide, as compared to a treatment with the FVIII alone; and/or wherein the frequency of administration of the FVIII is reduced, as compared to a treatment with the FVIII alone.

* * * * *

UNITED STATES PATENT AND TRADEMARK OFFICE
CERTIFICATE OF CORRECTION

PATENT NO. : 10,806,774 B2  
APPLICATION NO. : 16/068181  
DATED : October 20, 2020  
INVENTOR(S) : Arna Andrews et al.

Page 1 of 1

It is certified that error appears in the above-identified patent and that said Letters Patent is hereby corrected as shown below:

On the Title Page

Item (57), Line 8 of ABSTRACT, "the group consisting of SI, S3, LI 8," should read --the group consisting of S1, S3, L18,--.

Signed and Sealed this  
Ninth Day of March, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 32

<210> SEQ ID NO 1
<211> LENGTH: 8442
<212> TYPE: DNA
<213> ORGANISM: Homo sapiens

<400> SEQUENCE: 1

```
atgattcctg ccagatttgc cggggtgctg cttgctctgg ccctcatttt gccagggacc      60
ctttgtgcag aaggaactcg cggcaggtca tccacggccc gatgcagcct tttcggaagt     120
gacttcgtca acacctttga tgggagcatg tacagctttg cgggatactg cagttacctc     180
ctggcagggg gctgccagaa acgctccttc tcgattattg gggacttcca gaatggcaag     240
agagtgagcc tctccgtgta tcttgggaa ttttttgaca tccatttgtt tgtcaatggt     300
```

```
accgtgacac agggggacca aagagtctcc atgccctatg cctccaaagg gctgtatcta    360
gaaactgagg ctgggtacta caagctgtcc ggtgaggcct atggctttgt ggccaggatc    420
gatggcagcg gcaactttca agtcctgctg tcagacagat acttcaacaa gacctgcggg    480
ctgtgtggca actttaacat ctttgctgaa gatgacttta tgacccaaga agggaccttg    540
acctcggacc cttatgactt tgccaactca tgggctctga gcagtggaga acagtggtgt    600
gaacgggcat ctcctcccag cagctcatgc aacatctcct ctggggaaat gcagaagggc    660
ctgtgggagc agtgccagct tctgaagagc acctcggtgt tgcccgctg ccaccctctg    720
gtggaccccg agccttttgt ggccctgtgt gagaagactt tgtgtgagtg tgctgggggg    780
ctggagtgcg cctgccctgc cctcctggag tacgcccgga cctgtgccca ggagggaatg    840
gtgctgtacg gctggaccga ccacagcgcg tgcagcccag tgtgccctgc tggtatggag    900
tataggcagt gtgtgtcccc ttgcgccagg acctgccaga gcctgcacat caatgaaatg    960
tgtcaggagc gatgcgtgga tggctgcagc tgccctgagg acagctcct ggatgaaggc    1020
ctctgcgtgg agagcaccga gtgtcctgc gtgcattccg aaagcgcta ccctcccggc    1080
acctccctct ctcgagactg caacacctgc atttgccgaa acagccagtg gatctgcagc    1140
aatgaagaat gtccagggga gtgccttgtc acaggtcaat cacacttcaa gagctttgac    1200
aacagatact tcaccttcag tgggatctgc agtacctgc tggcccggga ttgccaggac    1260
cactccttct ccattgtcat tgagactgtc cagtgtgctg atgaccgcga cgctgtgtgc    1320
acccgctccg tcaccgtccg gctgcctggc ctgcacaaca gccttgtgaa actgaagcat    1380
ggggcaggag ttgccatgga tggccaggac gtccagctcc cctcctgaa aggtgaccc    1440
cgcatccagc atacagtgac ggcctccgtg cgcctcagct acggggagga cctgcagatg    1500
gactgggatg gccgcggag gctgctgtg aagctgtccc ccgtctatgc cgggaagacc    1560
tgcggcctgt gtgggaatta caatggcaac cagggcgacg acttccttac ccctctgggg    1620
ctggcggagc cccgggtgga ggacttcggg aacgcctgga gctgcacgg ggactgccag    1680
gacctgcaga gcagcacag cgatccctgc gccctcaacc cgcgcatgac caggttctcc    1740
gaggaggcgt gcgcggtcct gacgtccccc acattcgagg cctgccatcg tgccgtcagc    1800
ccgctgccct acctgcggaa ctgccgctac gacgtgtgct cctgctcgga cggccgcgag    1860
tgcctgtgcg gcgccctggc cagctatgcc gcggcctgcg cggggagagg cgtgcgcgtc    1920
gcgtggcgcg agccaggccg ctgtgagctg aactgcccga aggccaggt gtacctgcag    1980
tgcgggaccc cctgcaacct gacctgccgc tctctctctt acccggatga ggaatgcaat    2040
gaggcctgcc tggagggctg cttctgcccc ccagggctct acatggatga ggggggggac    2100
tgcgtgccca aggccagtg cccctgttac tatgacggtg agatcttcca gccagaagac    2160
atcttctcag accatcacac catgtgctac tgtgaggatg gcttcatgca ctgtaccatg    2220
agtggagtcc ccgaagctt gctgcctgac gctgtcctca gcagtcccct gtctcatcgc    2280
agcaaaagga gcctatcctg tcggccccc atggtcaagc tggtgtgtcc cgctgacaac    2340
ctgcggctg aagggctcga gtgtaccaaa acgtgccaga actatgacct ggagtgcatg    2400
agcatgggct gtgtctctgg ctgcctctgc ccccgggca tggtccggca tgagaacaga    2460
tgtgtggccc tggaaaggt tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
```

```
ctcaaatacc tgttccccgg ggagtgccag tacgttctgg tgcaggatta ctgcggcagt      2700
aaccctggga cctttcggat cctagtgggg aataagggat gcagccaccc ctcagtgaaa      2760
tgcaagaaac gggtcaccat cctggtggag ggaggagaga ttgagctgtt tgacggggag      2820
gtgaatgtga agaggcccat gaaggatgag actcactttg aggtggtgga gtctggccgg      2880
tacatcattc tgctgctggg caaagccctc tccgtggtct gggaccgcca cctgagcatc      2940
tccgtggtcc tgaagcagac ataccaggag aaagtgtgtg gcctgtgtgg gaattttgat      3000
ggcatccaga acaatgacct caccagcagc aacctccaag tggaggaaga ccctgtggac      3060
tttgggaact cctggaaagt gagctcgcag tgtgctgaca ccagaaaagt gcctctggac      3120
tcatcccctg ccacctgcca taacaacatc atgaagcaga cgatggtgga ttcctcctgt      3180
agaatcctta ccagtgacgt cttccaggac tgcaacaagc tggtggaccc cgagccatat      3240
ctggatgtct gcatttacga cacctgctcc tgtgagtcca ttggggactg cgcctgcttc      3300
tgcgacacca ttgctgccta tgcccacgtg tgtgccagc atggcaaggt ggtgacctgg      3360
aggacggcca cattgtgccc ccagagctgc gaggagagga tctccgggga gaacgggtat      3420
gagtgtgagt ggcgctataa cagctgtgca cctgcctgtc aagtcacgtg tcagcaccct      3480
gagccactgg cctgccctgt gcagtgtgtg gagggctgcc atgcccactg ccctccaggg      3540
aaaatcctgg atgagctttt gcagacctgc gttgaccctg aagactgtcc agtgtgtgag      3600
gtggctggcc ggcgttttgc ctcaggaaag aaagtcacct gaatcccag tgaccctgag      3660 cactgccaga tttgccactg tgatgttgtc aacctcacct gtgaagcctg ccaggagccg      3720
ggaggcctgg tggtgcctcc cacagatgcc ccggtgagcc ccaccactct gtatgtggag      3780
gacatctcgg aaccgccgtt gcacgatttc tactgcagca ggctactgga cctggtcttc      3840
ctgctggatg ctcctccag gctgtccgag gctgagtttg aagtgctgaa ggcctttgtg      3900
gtggacatga tggagcggct gcgcatctcc cagaagtggg tccgcgtggc cgtggtggag      3960
taccacgacg gctcccacgc ctacatcggg ctcaaggacc ggaagcgacc gtcagagctg      4020
cggcgcattg ccagccaggt gaagtatgcg ggcagccagg tggcctccac cagcgaggtc      4080
ttgaaataca cactgttcca aatcttcagc aagatcgacc gccctgaagc ctcccgcatc      4140
gccctgctcc tgatggccag ccaggagccc caacggatgt cccggaactt tgtccgctac      4200
gtccagggcc tgaagaagaa gaaggtcatt gtgatcccgg tgggcattgg gccccatgcc      4260
aacctcaagc agatccgcct catcgagaag caggcccctg agaacaaggc cttcgtgctg      4320
agcagtgtgg atgagctgga gcagcaaagg gacgagatcg ttagctacct ctgtgacctt      4380
gcccctgaag cccctcctcc tactctgccc ccccacatgg cacaagtcac tgtgggcccg      4440
gggctcttgg gggtttcgac cctggggccc aagaggaact ccatggttct ggatgtggcg      4500
ttcgtcctgg aaggatcgga caaaattggt gaagccgact tcaacaggag caaggagttc      4560
atggaggagg tgattcagcg gatgatgtg ggccaggaca gcatccacgt cacggtgctg      4620
cagtactcct acatggtgac cgtggagtac cccttcagcg aggcacagtc caaagggac      4680 atcctgcagc gggtgcgaga gatccgctac cagggcggca acaggaccaa cactgggctg      4740
gccctgcgcg acctctctga ccacagcttc ttggtcagcc agggtgaccg ggagcaggcg      4800
cccaacctgg tctacatggt caccggaaat cctgcctctg atgagatcaa gaggctgcct      4860
ggagacatcc aggtggtgcc cattggagtg ggccctaatg ccaacgtgca ggagctggag      4920
aggattggct ggcccaatgc ccctatcctc atccaggact ttgagacgct ccccgagag      4980 gctcctgacc tggtgctgca gaggtgctgc tccggagagg ggctgcagat ccccacccctc    5040
```

-continued

```
tcccctgcac ctgactgcag ccagcccctg gacgtgatcc ttctcctgga tggctcctcc   5100
agtttcccag cttcttattt tgatgaaatg aagagtttcg ccaaggcttt catttcaaaa   5160
gccaatatag ggcctcgtct cactcaggtg tcagtgctgc agtatggaag catcaccacc   5220
attgacgtgc catggaacgt ggtcccggag aaagcccatt tgctgagcct tgtggacgtc   5280
atgcagcggg agggaggccc cagccaaatc ggggatgcct gggctttgc tgtgcgatac    5340 ttgacttcag aaatgcatgg ggcgcgcccg ggagcctcaa aggcggtggt catcctggtc   5400
acggacgtct ctgtggattc agtggatgca gcagctgatg ccgccaggtc aacagagtg    5460 acagtgttcc ctattggaat tggagatcgc tacgatgcag cccagctacg atcttggca    5520 ggcccagcag gcgactccaa cgtggtgaag ctccagcgaa tcgaagacct ccctaccatg   5580
gtcaccttgg gcaattcctt cctccacaaa ctgtgctctg gatttgttag gatttgcatg   5640
gatgaggatg ggaatgagaa gaggcccggg gacgtctgga ccttgccaga ccagtgccac   5700
accgtgactt gccagccaga tggccagacc ttgctgaaga gtcatcgggt caactgtgac   5760
cgggggctga ggccttcgtg ccctaacagc cagtcccctg ttaaagtgga agagacctgt   5820
ggctgccgct ggacctgccc ctgcgtgtgc acaggcagct ccactcggca catcgtgacc   5880
tttgatgggc agaatttcaa gctgactggc agctgttctt atgtcctatt tcaaaacaag   5940
gagcaggacc tggaggtgat tctccataat ggtgcctgca gccctggagc aaggcagggc   6000
tgcatgaaat ccatcgaggt gaagcacagt gccctctccg tcgagctgca cagtgacatg   6060
gaggtgacgg tgaatgggag actggtctct gttccttacg tgggtgggaa catggaagtc   6120
aacgtttatg gtgccatcat gcatgaggtc agattcaatc accttggtca catcttcaca   6180
ttcactccac aaaacaatga gttccaactg cagctcagcc caagacttt tgcttcaaag    6240 acgtatggtc tgtgtgggat ctgtgatgag aacggagcca atgacttcat gctgagggat   6300
ggcacagtca ccacagactg gaaaacactt gttcaggaat ggactgtgca gcggccaggg   6360
cagacgtgcc agcccatcct ggaggagcag tgtcttgtcc ccgacagctc ccactgccag   6420
gtcctcctct taccactgtt tgctgaatgc acaaggtcc tggctccagc acattctat    6480 gccatctgcc agcaggacag ttgccaccag gagcaagtgt gtgaggtgat cgcctcttat   6540
gcccacctct gtcggaccaa cggggtctgc gttgactgga ggacacctga tttctgtgct   6600
atgtcatgcc caccatctct ggtttataac cactgtgagc atggctgtcc ccggcactgt   6660
gatggcaacg tgagctcctg tgggaccat ccctccgaag gctgtttctg ccctccagat    6720
aaagtcatgt tggaaggcag ctgtgtccct gaagaggcct gcactcagtg cattggtgag   6780
gatggagtcc agcaccagtt cctggaagcc tgggtcccgg accaccagcc ctgtcagatc   6840
tgcacatgcc tcagcgggcg gaaggtcaac tgcacaacgc agccctgccc cacggccaaa   6900
gctcccacgt gtggcctgtg tgaagtagcc cgcctccgcc agaatgcaga ccagtgctgc   6960
cccgagtatg agtgtgtgtg tgacccagtg agctgtgacc tgccccagt gcctcactgt    7020 gaacgtggcc tccagcccac actgaccaac cctggcgagt gcagacccaa cttcacctgc   7080
gcctgcagga aggaggagtg caaaagagtg tccccaccct cctgccccc gcaccgtttg    7140 cccaccctc ggaagaccca gtgctgtgat gagtatgagt gtgcctgcaa ctgtgtcaac    7200
tccacagtga gctgtccct tgggtacttg gcctcaaccg ccaccaatga ctgtggctgt   7260
accacaacca cctgccttcc cgacaaggtg tgtgtccacc gaagcaccat ctaccctgtg   7320
ggccagttct gggaggaggg ctgcgatgtg tgcacctgca ccgacatgga ggatgccgtg   7380
```

-continued

```
atgggcctcc gcgtggccca gtgctcccag aagccctgtg aggacagctg tcggtcgggc      7440
ttcacttacg ttctgcatga aggcgagtgc tgtggaaggt gcctgccatc tgcctgtgag      7500
gtggtgactg gctcaccgcg gggggactcc cagtcttcct ggaagagtgt cggctcccag      7560
tgggcctccc cggagaaccc ctgcctcatc aatgagtgtg tccgagtgaa ggaggaggtc      7620
tttatacaac aaaggaacgt ctcctgcccc cagctggagg tccctgtctg cccctcgggc      7680
tttcagctga gctgtaagac ctcagcgtgc tgcccaagct gtcgctgtga gcgcatggag      7740
gcctgcatgc tcaatggcac tgtcattggg cccgggaaga ctgtgatgat cgatgtgtgc      7800
acgacctgcc gctgcatggt gcaggtgggg gtcatctctg gattcaagct ggagtgcagg      7860
aagaccacct gcaaccccty ccccctgggt tacaaggaag aaaataacac aggtgaatgt      7920
tgtgggagat gtttgcctac ggcttgcacc attcagctaa gaggaggaca gatcatgaca      7980
ctgaagcgtg atgagacgct ccaggatggc tgtgatactc acttctgcaa ggtcaatgag      8040
agaggagagt acttctggga gaagagggtc acaggctgcc cacccttga tgaacacaag      8100
tgtctggctg agggaggtaa aattatgaaa attccaggca cctgctgtga cacatgtgag      8160
gagcctgagt gcaacgacat cactgccagg ctgcagtatg tcaaggtggg aagctgtaag      8220
tctgaagtag aggtggatat ccactactgc cagggcaaat gtgccagcaa agccatgtac      8280
tccattgaca tcaacgatgt gcaggaccag tgctcctgct gctctccgac acggacggag      8340
cccatgcagg tggccctgca ctgcaccaat ggctctgttg tgtaccatga ggttctcaat      8400
gccatggagt gcaaatgctc ccccaggaag tgcagcaagt ga                         8442
```

<210> SEQ ID NO 2
<211> LENGTH: 2813
<212> TYPE: PRT
<213> ORGANISM: Homo sapiens

<400> SEQUENCE: 2

```
Met Ile Pro Ala Arg Phe Ala Gly Val Leu Leu Ala Leu Ala Leu Ile
  1               5                  10                  15

Leu Pro Gly Thr Leu Cys Ala Glu Gly Thr Arg Gly Arg Ser Ser Thr
             20                  25                  30

Ala Arg Cys Ser Leu Phe Gly Ser Asp Phe Val Asn Thr Phe Asp Gly
         35                  40                  45

Ser Met Tyr Ser Phe Ala Gly Tyr Cys Ser Tyr Leu Leu Ala Gly Gly
     50                  55                  60

Cys Gln Lys Arg Ser Phe Ser Ile Ile Gly Asp Phe Gln Asn Gly Lys
 65                  70                  75                  80

Arg Val Ser Leu Ser Val Tyr Leu Gly Glu Phe Phe Asp Ile His Leu
                 85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190
```

-continued

Leu Ser Ser Gly Glu Gln Trp Cys Glu Arg Ala Ser Pro Ser Ser
    195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
            245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
        290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

```
Arg Tyr Asp Val Cys Ser Cys Ser Asp Gly Arg Glu Cys Leu Cys Gly
    610             615             620

Ala Leu Ala Ser Tyr Ala Ala Cys Ala Gly Arg Gly Val Arg Val
625             630             635             640

Ala Trp Arg Glu Pro Gly Arg Cys Glu Leu Asn Cys Pro Lys Gly Gln
            645             650             655

Val Tyr Leu Gln Cys Gly Thr Pro Cys Asn Leu Thr Cys Arg Ser Leu
        660             665             670

Ser Tyr Pro Asp Glu Glu Cys Asn Glu Ala Cys Leu Glu Gly Cys Phe
        675             680             685

Cys Pro Pro Gly Leu Tyr Met Asp Glu Arg Gly Asp Cys Val Pro Lys
    690             695             700

Ala Gln Cys Pro Cys Tyr Tyr Asp Gly Glu Ile Phe Gln Pro Glu Asp
705             710             715             720

Ile Phe Ser Asp His His Thr Met Cys Tyr Cys Glu Asp Gly Phe Met
                725             730             735

His Cys Thr Met Ser Gly Val Pro Gly Ser Leu Leu Pro Asp Ala Val
            740             745             750

Leu Ser Ser Pro Leu Ser His Arg Ser Lys Arg Ser Leu Ser Cys Arg
        755             760             765

Pro Pro Met Val Lys Leu Val Cys Pro Ala Asp Asn Leu Arg Ala Glu
    770             775             780

Gly Leu Glu Cys Thr Lys Thr Cys Gln Asn Tyr Asp Leu Glu Cys Met
785             790             795             800

Ser Met Gly Cys Val Ser Gly Cys Leu Cys Pro Pro Gly Met Val Arg
            805             810             815

His Glu Asn Arg Cys Val Ala Leu Glu Arg Cys Pro Cys Phe His Gln
        820             825             830

Gly Lys Glu Tyr Ala Pro Gly Glu Thr Val Lys Ile Gly Cys Asn Thr
        835             840             845

Cys Val Cys Arg Asp Arg Lys Trp Asn Cys Thr Asp His Val Cys Asp
    850             855             860

Ala Thr Cys Ser Thr Ile Gly Met Ala His Tyr Leu Thr Phe Asp Gly
865             870             875             880

Leu Lys Tyr Leu Phe Pro Gly Glu Cys Gln Tyr Val Leu Val Gln Asp
            885             890             895

Tyr Cys Gly Ser Asn Pro Gly Thr Phe Arg Ile Leu Val Gly Asn Lys
        900             905             910

Gly Cys Ser His Pro Ser Val Lys Cys Lys Arg Val Thr Ile Leu
        915             920             925

Val Glu Gly Gly Glu Ile Glu Leu Phe Asp Gly Glu Val Asn Val Lys
    930             935             940

Arg Pro Met Lys Asp Glu Thr His Phe Glu Val Val Glu Ser Gly Arg
945             950             955             960

Tyr Ile Ile Leu Leu Leu Gly Lys Ala Leu Ser Val Val Trp Asp Arg
            965             970             975

His Leu Ser Ile Ser Val Val Leu Lys Gln Thr Tyr Gln Glu Lys Val
        980             985             990

Cys Gly Leu Cys Gly Asn Phe Asp  Gly Ile Gln Asn Asn  Asp Leu Thr
        995             1000             1005

Ser Ser  Asn Leu Gln Val Glu  Glu Asp Pro Val Asp  Phe Gly Asn
    1010             1015             1020

Ser Trp  Lys Val Ser Ser Gln  Cys Ala Asp Thr Arg  Lys Val Pro
```

```
            1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335

Glu Leu Arg Arg Ile Ala Ser Gln Val Lys Tyr Ala Gly Ser Gln
    1340                1345                1350

Val Ala Ser Thr Ser Glu Val Leu Lys Tyr Thr Leu Phe Gln Ile
    1355                1360                1365

Phe Ser Lys Ile Asp Arg Pro Glu Ala Ser Arg Ile Thr Leu Leu
    1370                1375                1380

Leu Met Ala Ser Gln Glu Pro Gln Arg Met Ser Arg Asn Phe Val
    1385                1390                1395

Arg Tyr Val Gln Gly Leu Lys Lys Lys Lys Val Ile Val Ile Pro
    1400                1405                1410

Val Gly Ile Gly Pro His Ala Asn Leu Lys Gln Ile Arg Leu Ile
    1415                1420                1425
```

-continued

Glu Lys Gln Ala Pro Glu Asn Lys Ala Phe Val Leu Ser Ser Val
1430            1435            1440

Asp Glu Leu Glu Gln Gln Arg Asp Glu Ile Val Ser Tyr Leu Cys
1445            1450            1455

Asp Leu Ala Pro Glu Ala Pro Pro Thr Leu Pro Pro Asp Met
1460            1465            1470

Ala Gln Val Thr Val Gly Pro Gly Leu Leu Gly Val Ser Thr Leu
1475            1480            1485

Gly Pro Lys Arg Asn Ser Met Val Leu Asp Val Ala Phe Val Leu
1490            1495            1500

Glu Gly Ser Asp Lys Ile Gly Glu Ala Asp Phe Asn Arg Ser Lys
1505            1510            1515

Glu Phe Met Glu Glu Val Ile Gln Arg Met Asp Val Gly Gln Asp
1520            1525            1530

Ser Ile His Val Thr Val Leu Gln Tyr Ser Tyr Met Val Thr Val
1535            1540            1545

Glu Tyr Pro Phe Ser Glu Ala Gln Ser Lys Gly Asp Ile Leu Gln
1550            1555            1560

Arg Val Arg Glu Ile Arg Tyr Gln Gly Gly Asn Arg Thr Asn Thr
1565            1570            1575

Gly Leu Ala Leu Arg Tyr Leu Ser Asp His Ser Phe Leu Val Ser
1580            1585            1590

Gln Gly Asp Arg Glu Gln Ala Pro Asn Leu Val Tyr Met Val Thr
1595            1600            1605

Gly Asn Pro Ala Ser Asp Glu Ile Lys Arg Leu Pro Gly Asp Ile
1610            1615            1620

Gln Val Val Pro Ile Gly Val Gly Pro Asn Ala Asn Val Gln Glu
1625            1630            1635

Leu Glu Arg Ile Gly Trp Pro Asn Ala Pro Ile Leu Ile Gln Asp
1640            1645            1650

Phe Glu Thr Leu Pro Arg Glu Ala Pro Asp Leu Val Leu Gln Arg
1655            1660            1665

Cys Cys Ser Gly Glu Gly Leu Gln Ile Pro Thr Leu Ser Pro Ala
1670            1675            1680

Pro Asp Cys Ser Gln Pro Leu Asp Val Ile Leu Leu Leu Asp Gly
1685            1690            1695

Ser Ser Ser Phe Pro Ala Ser Tyr Phe Asp Glu Met Lys Ser Phe
1700            1705            1710

Ala Lys Ala Phe Ile Ser Lys Ala Asn Ile Gly Pro Arg Leu Thr
1715            1720            1725

Gln Val Ser Val Leu Gln Tyr Gly Ser Ile Thr Thr Ile Asp Val
1730            1735            1740

Pro Trp Asn Val Val Pro Glu Lys Ala His Leu Leu Ser Leu Val
1745            1750            1755

Asp Val Met Gln Arg Glu Gly Gly Pro Ser Gln Ile Gly Asp Ala
1760            1765            1770

Leu Gly Phe Ala Val Arg Tyr Leu Thr Ser Glu Met His Gly Ala
1775            1780            1785

Arg Pro Gly Ala Ser Lys Ala Val Val Ile Leu Val Thr Asp Val
1790            1795            1800

Ser Val Asp Ser Val Asp Ala Ala Asp Ala Ala Arg Ser Asn
1805            1810            1815

```
Arg Val Thr Val Phe Pro Ile Gly Ile Gly Asp Arg Tyr Asp Ala
    1820                1825                1830
Ala Gln Leu Arg Ile Leu Ala Gly Pro Ala Gly Asp Ser Asn Val
    1835                1840                1845
Val Lys Leu Gln Arg Ile Glu Asp Leu Pro Thr Met Val Thr Leu
    1850                1855                1860
Gly Asn Ser Phe Leu His Lys Leu Cys Ser Gly Phe Val Arg Ile
    1865                1870                1875
Cys Met Asp Glu Asp Gly Asn Glu Lys Arg Pro Gly Asp Val Trp
    1880                1885                1890
Thr Leu Pro Asp Gln Cys His Thr Val Thr Cys Gln Pro Asp Gly
    1895                1900                1905
Gln Thr Leu Leu Lys Ser His Arg Val Asn Cys Asp Arg Gly Leu
    1910                1915                1920
Arg Pro Ser Cys Pro Asn Ser Gln Ser Pro Val Lys Val Glu Glu
    1925                1930                1935
Thr Cys Gly Cys Arg Trp Thr Cys Pro Cys Val Cys Thr Gly Ser
    1940                1945                1950
Ser Thr Arg His Ile Val Thr Phe Asp Gly Gln Asn Phe Lys Leu
    1955                1960                1965
Thr Gly Ser Cys Ser Tyr Val Leu Phe Gln Asn Lys Glu Gln Asp
    1970                1975                1980
Leu Glu Val Ile Leu His Asn Gly Ala Cys Ser Pro Gly Ala Arg
    1985                1990                1995
Gln Gly Cys Met Lys Ser Ile Glu Val Lys His Ser Ala Leu Ser
    2000                2005                2010
Val Glu Leu His Ser Asp Met Glu Val Thr Val Asn Gly Arg Leu
    2015                2020                2025
Val Ser Val Pro Tyr Val Gly Gly Asn Met Glu Val Asn Val Tyr
    2030                2035                2040
Gly Ala Ile Met His Glu Val Arg Phe Asn His Leu Gly His Ile
    2045                2050                2055
Phe Thr Phe Thr Pro Gln Asn Asn Glu Phe Gln Leu Gln Leu Ser
    2060                2065                2070
Pro Lys Thr Phe Ala Ser Lys Thr Tyr Gly Leu Cys Gly Ile Cys
    2075                2080                2085
Asp Glu Asn Gly Ala Asn Asp Phe Met Leu Arg Asp Gly Thr Val
    2090                2095                2100
Thr Thr Asp Trp Lys Thr Leu Val Gln Glu Trp Thr Val Gln Arg
    2105                2110                2115
Pro Gly Gln Thr Cys Gln Pro Ile Leu Glu Glu Gln Cys Leu Val
    2120                2125                2130
Pro Asp Ser Ser His Cys Gln Val Leu Leu Leu Pro Leu Phe Ala
    2135                2140                2145
Glu Cys His Lys Val Leu Ala Pro Ala Thr Phe Tyr Ala Ile Cys
    2150                2155                2160
Gln Gln Asp Ser Cys His Gln Glu Gln Val Cys Glu Val Ile Ala
    2165                2170                2175
Ser Tyr Ala His Leu Cys Arg Thr Asn Gly Val Cys Val Asp Trp
    2180                2185                2190
Arg Thr Pro Asp Phe Cys Ala Met Ser Cys Pro Pro Ser Leu Val
    2195                2200                2205
Tyr Asn His Cys Glu His Gly Cys Pro Arg His Cys Asp Gly Asn
```

-continued

```
             2210                2215                2220
Val  Ser  Ser  Cys  Gly  Asp  His  Pro  Ser  Glu  Gly  Cys  Phe  Cys  Pro
     2225                2230                2235

Pro  Asp  Lys  Val  Met  Leu  Glu  Gly  Ser  Cys  Val  Pro  Glu  Glu  Ala
     2240                2245                2250

Cys  Thr  Gln  Cys  Ile  Gly  Glu  Asp  Gly  Val  Gln  His  Gln  Phe  Leu
     2255                2260                2265

Glu  Ala  Trp  Val  Pro  Asp  His  Gln  Pro  Cys  Gln  Ile  Cys  Thr  Cys
     2270                2275                2280

Leu  Ser  Gly  Arg  Lys  Val  Asn  Cys  Thr  Thr  Gln  Pro  Cys  Pro  Thr
     2285                2290                2295

Ala  Lys  Ala  Pro  Thr  Cys  Gly  Leu  Cys  Glu  Val  Ala  Arg  Leu  Arg
     2300                2305                2310

Gln  Asn  Ala  Asp  Gln  Cys  Cys  Pro  Glu  Tyr  Glu  Cys  Val  Cys  Asp
     2315                2320                2325

Pro  Val  Ser  Cys  Asp  Leu  Pro  Pro  Val  Pro  His  Cys  Glu  Arg  Gly
     2330                2335                2340

Leu  Gln  Pro  Thr  Leu  Thr  Asn  Pro  Gly  Glu  Cys  Arg  Pro  Asn  Phe
     2345                2350                2355

Thr  Cys  Ala  Cys  Arg  Lys  Glu  Glu  Cys  Lys  Arg  Val  Ser  Pro  Pro
     2360                2365                2370

Ser  Cys  Pro  Pro  His  Arg  Leu  Pro  Thr  Leu  Arg  Lys  Thr  Gln  Cys
     2375                2380                2385

Cys  Asp  Glu  Tyr  Glu  Cys  Ala  Cys  Asn  Cys  Val  Asn  Ser  Thr  Val
     2390                2395                2400

Ser  Cys  Pro  Leu  Gly  Tyr  Leu  Ala  Ser  Thr  Ala  Thr  Asn  Asp  Cys
     2405                2410                2415

Gly  Cys  Thr  Thr  Thr  Thr  Cys  Leu  Pro  Asp  Lys  Val  Cys  Val  His
     2420                2425                2430

Arg  Ser  Thr  Ile  Tyr  Pro  Val  Gly  Gln  Phe  Trp  Glu  Glu  Gly  Cys
     2435                2440                2445

Asp  Val  Cys  Thr  Cys  Thr  Asp  Met  Glu  Asp  Ala  Val  Met  Gly  Leu
     2450                2455                2460

Arg  Val  Ala  Gln  Cys  Ser  Gln  Lys  Pro  Cys  Glu  Asp  Ser  Cys  Arg
     2465                2470                2475

Ser  Gly  Phe  Thr  Tyr  Val  Leu  His  Glu  Gly  Glu  Cys  Cys  Gly  Arg
     2480                2485                2490

Cys  Leu  Pro  Ser  Ala  Cys  Glu  Val  Val  Thr  Gly  Ser  Pro  Arg  Gly
     2495                2500                2505

Asp  Ser  Gln  Ser  Ser  Trp  Lys  Ser  Val  Gly  Ser  Gln  Trp  Ala  Ser
     2510                2515                2520

Pro  Glu  Asn  Pro  Cys  Leu  Ile  Asn  Glu  Cys  Val  Arg  Val  Lys  Glu
     2525                2530                2535

Glu  Val  Phe  Ile  Gln  Gln  Arg  Asn  Val  Ser  Cys  Pro  Gln  Leu  Glu
     2540                2545                2550

Val  Pro  Val  Cys  Pro  Ser  Gly  Phe  Gln  Leu  Ser  Cys  Lys  Thr  Ser
     2555                2560                2565

Ala  Cys  Cys  Pro  Ser  Cys  Arg  Cys  Glu  Arg  Met  Glu  Ala  Cys  Met
     2570                2575                2580

Leu  Asn  Gly  Thr  Val  Ile  Gly  Pro  Gly  Lys  Thr  Val  Met  Ile  Asp
     2585                2590                2595

Val  Cys  Thr  Thr  Cys  Arg  Cys  Met  Val  Gln  Val  Gly  Val  Ile  Ser
     2600                2605                2610
```

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 3
<211> LENGTH: 479
<212> TYPE: PRT
<213> ORGANISM: Homo sapiens

<400> SEQUENCE: 3

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
        130                 135                 140

Leu Val Gly Asn Lys Gly Cys Ser His Pro Ser Val Lys Cys Lys Lys

```
            145                 150                 155                 160
    Arg Val Thr Ile Leu Val Glu Gly Gly Glu Ile Glu Leu Phe Asp Gly
                    165                 170                 175

Glu Val Asn Val Lys Arg Pro Met Lys Asp Glu Thr His Phe Glu Val
                    180                 185                 190

Val Glu Ser Gly Arg Tyr Ile Leu Leu Gly Lys Ala Leu Ser
                    195                 200                 205

Val Val Trp Asp Arg His Leu Ser Ile Ser Val Leu Lys Gln Thr
                    210                 215                 220

Tyr Gln Glu Lys Val Cys Gly Leu Cys Gly Asn Phe Asp Gly Ile Gln
    225                 230                 235                 240

Asn Asn Asp Leu Thr Ser Ser Asn Leu Gln Val Glu Glu Asp Pro Val
                    245                 250                 255

Asp Phe Gly Asn Ser Trp Lys Val Ser Ser Gln Cys Ala Asp Thr Arg
                    260                 265                 270

Lys Val Pro Leu Asp Ser Ser Pro Ala Thr Cys His Asn Asn Ile Met
                    275                 280                 285

Lys Gln Thr Met Val Asp Ser Ser Cys Arg Ile Leu Thr Ser Asp Val
                    290                 295                 300

Phe Gln Asp Cys Asn Lys Leu Val Asp Pro Glu Pro Tyr Leu Asp Val
    305                 310                 315                 320

Cys Ile Tyr Asp Thr Cys Ser Cys Glu Ser Ile Gly Asp Cys Ala Cys
                    325                 330                 335

Phe Cys Asp Thr Ile Ala Ala Tyr Ala His Val Cys Ala Gln His Gly
                    340                 345                 350

Lys Val Val Thr Trp Arg Thr Ala Thr Leu Cys Pro Gln Ser Cys Glu
                    355                 360                 365

Glu Arg Asn Leu Arg Glu Asn Gly Tyr Glu Cys Glu Trp Arg Tyr Asn
                    370                 375                 380

Ser Cys Ala Pro Ala Cys Gln Val Thr Cys Gln His Pro Glu Pro Leu
    385                 390                 395                 400

Ala Cys Pro Val Gln Cys Val Glu Gly Cys His Ala His Cys Pro Pro
                    405                 410                 415

Gly Lys Ile Leu Asp Glu Leu Leu Gln Thr Cys Val Asp Pro Glu Asp
                    420                 425                 430

Cys Pro Val Cys Glu Val Ala Gly Arg Arg Phe Ala Ser Gly Lys Lys
                    435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly
    465                 470                 475

<210> SEQ ID NO 4
<211> LENGTH: 2050
<212> TYPE: PRT
<213> ORGANISM: Homo sapiens

<400> SEQUENCE: 4

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45
```

```
Pro Gly Met Val Arg His Glu Asn Arg Cys Val Ala Leu Glu Arg Cys
    50                  55                  60
Pro Cys Phe His Gln Gly Lys Glu Tyr Ala Pro Gly Glu Thr Val Lys
 65                  70                  75                  80
Ile Gly Cys Asn Thr Cys Val Cys Arg Asp Arg Lys Trp Asn Cys Thr
                85                  90                  95
Asp His Val Cys Asp Ala Thr Cys Ser Thr Ile Gly Met Ala His Tyr
            100                 105                 110
Leu Thr Phe Asp Gly Leu Lys Tyr Leu Phe Pro Gly Glu Cys Gln Tyr
        115                 120                 125
Val Leu Val Gln Asp Tyr Cys Gly Ser Asn Pro Gly Thr Phe Arg Ile
    130                 135                 140
Leu Val Gly Asn Lys Gly Cys Ser His Pro Ser Val Lys Cys Lys Lys
145                 150                 155                 160
Arg Val Thr Ile Leu Val Glu Gly Gly Glu Ile Glu Leu Phe Asp Gly
                165                 170                 175
Glu Val Asn Val Lys Arg Pro Met Lys Asp Glu Thr His Phe Glu Val
            180                 185                 190
Val Glu Ser Gly Arg Tyr Ile Ile Leu Leu Leu Gly Lys Ala Leu Ser
        195                 200                 205
Val Val Trp Asp Arg His Leu Ser Ile Ser Val Val Leu Lys Gln Thr
    210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                245                 250                 255
Asp Phe Gly Asn Ser Trp Lys Val Ser Ser Gln Cys Ala Asp Thr Arg
            260                 265                 270
Lys Val Pro Leu Asp Ser Ser Pro Ala Thr Cys His Asn Asn Ile Met
        275                 280                 285
Lys Gln Thr Met Val Asp Ser Ser Cys Arg Ile Leu Thr Ser Asp Val
    290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                325                 330                 335
Phe Cys Asp Thr Ile Ala Ala Tyr Ala His Val Cys Ala Gln His Gly
            340                 345                 350
Lys Val Val Thr Trp Arg Thr Ala Thr Leu Cys Pro Gln Ser Cys Glu
        355                 360                 365
Glu Arg Asn Leu Arg Glu Asn Gly Tyr Glu Cys Glu Trp Arg Tyr Asn
    370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                405                 410                 415
Gly Lys Ile Leu Asp Glu Leu Leu Gln Thr Cys Val Asp Pro Glu Asp
            420                 425                 430
Cys Pro Val Cys Glu Val Ala Gly Arg Arg Phe Ala Ser Gly Lys Lys
        435                 440                 445
Val Thr Leu Asn Pro Ser Asp Pro Glu His Cys Gln Ile Cys His Cys
    450                 455                 460
Asp Val Val Asn Leu Thr Cys Glu Ala Cys Gln Glu Pro Gly Gly Leu
```

-continued

```
            465                 470                 475                 480
        Val Val Pro Pro Thr Asp Ala Pro Val Ser Pro Thr Thr Leu Tyr Val
                        485                 490                 495

Glu Asp Ile Ser Glu Pro Pro Leu His Asp Phe Tyr Cys Ser Arg Leu
                        500                 505                 510

Leu Asp Leu Val Phe Leu Leu Asp Gly Ser Ser Arg Leu Ser Glu Ala
                        515                 520                 525

Glu Phe Glu Val Leu Lys Ala Phe Val Val Asp Met Met Glu Arg Leu
                530                 535                 540

Arg Ile Ser Gln Lys Trp Val Arg Val Ala Val Val Glu Tyr His Asp
        545                 550                 555                 560

Gly Ser His Ala Tyr Ile Gly Leu Lys Asp Arg Lys Arg Pro Ser Glu
                        565                 570                 575

Leu Arg Arg Ile Ala Ser Gln Val Lys Tyr Ala Gly Ser Gln Val Ala
                        580                 585                 590

Ser Thr Ser Glu Val Leu Lys Tyr Thr Leu Phe Gln Ile Phe Ser Lys
                595                 600                 605

Ile Asp Arg Pro Glu Ala Ser Arg Ile Thr Leu Leu Leu Met Ala Ser
                610                 615                 620

Gln Glu Pro Gln Arg Met Ser Arg Asn Phe Val Arg Tyr Val Gln Gly
        625                 630                 635                 640

Leu Lys Lys Lys Val Ile Val Ile Pro Val Gly Ile Gly Pro His
                        645                 650                 655

Ala Asn Leu Lys Gln Ile Arg Leu Ile Glu Lys Gln Ala Pro Glu Asn
                        660                 665                 670

Lys Ala Phe Val Leu Ser Ser Val Asp Glu Leu Glu Gln Gln Arg Asp
                        675                 680                 685

Glu Ile Val Ser Tyr Leu Cys Asp Leu Ala Pro Glu Ala Pro Pro Pro
                690                 695                 700

Thr Leu Pro Pro Asp Met Ala Gln Val Thr Val Gly Pro Gly Leu Leu
        705                 710                 715                 720

Gly Val Ser Thr Leu Gly Pro Lys Arg Asn Ser Met Val Leu Asp Val
                        725                 730                 735

Ala Phe Val Leu Glu Gly Ser Asp Lys Ile Gly Glu Ala Asp Phe Asn
                        740                 745                 750

Arg Ser Lys Glu Phe Met Glu Glu Val Ile Gln Arg Met Asp Val Gly
                        755                 760                 765

Gln Asp Ser Ile His Val Thr Val Leu Gln Tyr Ser Tyr Met Val Thr
        770                 775                 780

Val Glu Tyr Pro Phe Ser Glu Ala Gln Ser Lys Gly Asp Ile Leu Gln
        785                 790                 795                 800

Arg Val Arg Glu Ile Arg Tyr Gln Gly Gly Asn Arg Thr Asn Thr Gly
                        805                 810                 815

Leu Ala Leu Arg Tyr Leu Ser Asp His Ser Phe Leu Val Ser Gln Gly
                        820                 825                 830

Asp Arg Glu Gln Ala Pro Asn Leu Val Tyr Met Val Thr Gly Asn Pro
                        835                 840                 845

Ala Ser Asp Glu Ile Lys Arg Leu Pro Gly Asp Ile Gln Val Val Pro
                850                 855                 860

Ile Gly Val Gly Pro Asn Ala Asn Val Gln Glu Leu Glu Arg Ile Gly
        865                 870                 875                 880

Trp Pro Asn Ala Pro Ile Leu Ile Gln Asp Phe Glu Thr Leu Pro Arg
                        885                 890                 895
```

```
Glu Ala Pro Asp Leu Val Leu Gln Arg Cys Cys Ser Gly Glu Gly Leu
            900                 905                 910

Gln Ile Pro Thr Leu Ser Pro Ala Pro Asp Cys Ser Gln Pro Leu Asp
            915                 920                 925

Val Ile Leu Leu Leu Asp Gly Ser Ser Ser Phe Pro Ala Ser Tyr Phe
930                 935                 940

Asp Glu Met Lys Ser Phe Ala Lys Ala Phe Ile Ser Lys Ala Asn Ile
945                 950                 955                 960

Gly Pro Arg Leu Thr Gln Val Ser Val Leu Gln Tyr Gly Ser Ile Thr
            965                 970                 975

Thr Ile Asp Val Pro Trp Asn Val Pro Glu Lys Ala His Leu Leu
            980                 985                 990

Ser Leu Val Asp Val Met Gln Arg Glu Gly Gly Pro Ser Gln Ile Gly
            995                 1000                1005

Asp Ala Leu Gly Phe Ala Val Arg Tyr Leu Thr Ser Glu Met His
    1010                1015                1020

Gly Ala Arg Pro Gly Ala Ser Lys Ala Val Val Ile Leu Val Thr
    1025                1030                1035

Asp Val Ser Val Asp Ser Val Asp Ala Ala Ala Asp Ala Ala Arg
    1040                1045                1050

Ser Asn Arg Val Thr Val Phe Pro Ile Gly Ile Gly Asp Arg Tyr
    1055                1060                1065

Asp Ala Ala Gln Leu Arg Ile Leu Ala Gly Pro Ala Gly Asp Ser
    1070                1075                1080

Asn Val Val Lys Leu Gln Arg Ile Glu Asp Leu Pro Thr Met Val
    1085                1090                1095

Thr Leu Gly Asn Ser Phe Leu His Lys Leu Cys Ser Gly Phe Val
    1100                1105                1110

Arg Ile Cys Met Asp Glu Asp Gly Asn Glu Lys Arg Pro Gly Asp
    1115                1120                1125

Val Trp Thr Leu Pro Asp Gln Cys His Thr Val Thr Cys Gln Pro
    1130                1135                1140

Asp Gly Gln Thr Leu Leu Lys Ser His Arg Val Asn Cys Asp Arg
    1145                1150                1155

Gly Leu Arg Pro Ser Cys Pro Asn Ser Gln Ser Pro Val Lys Val
    1160                1165                1170

Glu Glu Thr Cys Gly Cys Arg Trp Thr Cys Pro Cys Val Cys Thr
    1175                1180                1185

Gly Ser Ser Thr Arg His Ile Val Thr Phe Asp Gly Gln Asn Phe
    1190                1195                1200

Lys Leu Thr Gly Ser Cys Ser Tyr Val Leu Phe Gln Asn Lys Glu
    1205                1210                1215

Gln Asp Leu Glu Val Ile Leu His Asn Gly Ala Cys Ser Pro Gly
    1220                1225                1230

Ala Arg Gln Gly Cys Met Lys Ser Ile Glu Val Lys His Ser Ala
    1235                1240                1245

Leu Ser Val Glu Leu His Ser Asp Met Glu Val Thr Val Asn Gly
    1250                1255                1260

Arg Leu Val Ser Val Pro Tyr Val Gly Gly Asn Met Glu Val Asn
    1265                1270                1275

Val Tyr Gly Ala Ile Met His Glu Val Arg Phe Asn His Leu Gly
    1280                1285                1290
```

```
His Ile Phe Thr Phe Thr Pro Gln Asn Asn Glu Phe Gln Leu Gln
1295                1300                1305

Leu Ser Pro Lys Thr Phe Ala Ser Lys Thr Tyr Gly Leu Cys Gly
1310                1315                1320

Ile Cys Asp Glu Asn Gly Ala Asn Asp Phe Met Leu Arg Asp Gly
1325                1330                1335

Thr Val Thr Thr Asp Trp Lys Thr Leu Val Gln Glu Trp Thr Val
1340                1345                1350

Gln Arg Pro Gly Gln Thr Cys Gln Pro Ile Leu Glu Glu Gln Cys
1355                1360                1365

Leu Val Pro Asp Ser Ser His Cys Gln Val Leu Leu Pro Leu
1370                1375                1380

Phe Ala Glu Cys His Lys Val Leu Ala Pro Ala Thr Phe Tyr Ala
1385                1390                1395

Ile Cys Gln Gln Asp Ser Cys His Gln Glu Gln Val Cys Glu Val
1400                1405                1410

Ile Ala Ser Tyr Ala His Leu Cys Arg Thr Asn Gly Val Cys Val
1415                1420                1425

Asp Trp Arg Thr Pro Asp Phe Cys Ala Met Ser Cys Pro Pro Ser
1430                1435                1440

Leu Val Tyr Asn His Cys Glu His Gly Cys Pro Arg His Cys Asp
1445                1450                1455

Gly Asn Val Ser Ser Cys Gly Asp His Pro Ser Glu Gly Cys Phe
1460                1465                1470

Cys Pro Pro Asp Lys Val Met Leu Glu Gly Ser Cys Val Pro Glu
1475                1480                1485

Glu Ala Cys Thr Gln Cys Ile Gly Glu Asp Gly Val Gln His Gln
1490                1495                1500

Phe Leu Glu Ala Trp Val Pro Asp His Gln Pro Cys Gln Ile Cys
1505                1510                1515

Thr Cys Leu Ser Gly Arg Lys Val Asn Cys Thr Thr Gln Pro Cys
1520                1525                1530

Pro Thr Ala Lys Ala Pro Thr Cys Gly Leu Cys Glu Val Ala Arg
1535                1540                1545

Leu Arg Gln Asn Ala Asp Gln Cys Cys Pro Glu Tyr Glu Cys Val
1550                1555                1560

Cys Asp Pro Val Ser Cys Asp Leu Pro Pro Val Pro His Cys Glu
1565                1570                1575

Arg Gly Leu Gln Pro Thr Leu Thr Asn Pro Gly Glu Cys Arg Pro
1580                1585                1590

Asn Phe Thr Cys Ala Cys Arg Lys Glu Glu Cys Lys Arg Val Ser
1595                1600                1605

Pro Pro Ser Cys Pro Pro His Arg Leu Pro Thr Leu Arg Lys Thr
1610                1615                1620

Gln Cys Cys Asp Glu Tyr Glu Cys Ala Cys Asn Cys Val Asn Ser
1625                1630                1635

Thr Val Ser Cys Pro Leu Gly Tyr Leu Ala Ser Thr Ala Thr Asn
1640                1645                1650

Asp Cys Gly Cys Thr Thr Thr Cys Leu Pro Asp Lys Val Cys
1655                1660                1665

Val His Arg Ser Thr Ile Tyr Pro Val Gly Gln Phe Trp Glu Glu
1670                1675                1680

Gly Cys Asp Val Cys Thr Cys Thr Asp Met Glu Asp Ala Val Met
```

```
                    1685                1690                1695

Gly Leu Arg Val Ala Gln Cys Ser Gln Lys Pro Cys Glu Asp Ser
    1700                1705                1710

Cys Arg Ser Gly Phe Thr Tyr Val Leu His Glu Gly Glu Cys Cys
    1715                1720                1725

Gly Arg Cys Leu Pro Ser Ala Cys Glu Val Val Thr Gly Ser Pro
    1730                1735                1740

Arg Gly Asp Ser Gln Ser Ser Trp Lys Ser Val Gly Ser Gln Trp
    1745                1750                1755

Ala Ser Pro Glu Asn Pro Cys Leu Ile Asn Glu Cys Val Arg Val
    1760                1765                1770

Lys Glu Glu Val Phe Ile Gln Gln Arg Asn Val Ser Cys Pro Gln
    1775                1780                1785

Leu Glu Val Pro Val Cys Pro Ser Gly Phe Gln Leu Ser Cys Lys
    1790                1795                1800

Thr Ser Ala Cys Cys Pro Ser Cys Arg Cys Glu Arg Met Glu Ala
    1805                1810                1815

Cys Met Leu Asn Gly Thr Val Ile Gly Pro Gly Lys Thr Val Met
    1820                1825                1830

Ile Asp Val Cys Thr Thr Cys Arg Cys Met Val Gln Val Gly Val
    1835                1840                1845

Ile Ser Gly Phe Lys Leu Glu Cys Arg Lys Thr Thr Cys Asn Pro
    1850                1855                1860

Cys Pro Leu Gly Tyr Lys Glu Glu Asn Asn Thr Gly Glu Cys Cys
    1865                1870                1875

Gly Arg Cys Leu Pro Thr Ala Cys Thr Ile Gln Leu Arg Gly Gly
    1880                1885                1890

Gln Ile Met Thr Leu Lys Arg Asp Glu Thr Leu Gln Asp Gly Cys
    1895                1900                1905

Asp Thr His Phe Cys Lys Val Asn Glu Arg Gly Glu Tyr Phe Trp
    1910                1915                1920

Glu Lys Arg Val Thr Gly Cys Pro Pro Phe Asp Glu His Lys Cys
    1925                1930                1935

Leu Ala Glu Gly Gly Lys Ile Met Lys Ile Pro Gly Thr Cys Cys
    1940                1945                1950

Asp Thr Cys Glu Glu Pro Glu Cys Asn Asp Ile Thr Ala Arg Leu
    1955                1960                1965

Gln Tyr Val Lys Val Gly Ser Cys Lys Ser Glu Val Glu Val Asp
    1970                1975                1980

Ile His Tyr Cys Gln Gly Lys Cys Ala Ser Lys Ala Met Tyr Ser
    1985                1990                1995

Ile Asp Ile Asn Asp Val Gln Asp Gln Cys Ser Cys Cys Ser Pro
    2000                2005                2010

Thr Arg Thr Glu Pro Met Gln Val Ala Leu His Cys Thr Asn Gly
    2015                2020                2025

Ser Val Val Tyr His Glu Val Leu Asn Ala Met Glu Cys Lys Cys
    2030                2035                2040

Ser Pro Arg Lys Cys Ser Lys
    2045                2050

<210> SEQ ID NO 5
<211> LENGTH: 479
<212> TYPE: PRT
<213> ORGANISM: Artificial sequence
```

<220> FEATURE:
<223> OTHER INFORMATION: Modified D'-D3 domain of VWFPRT

<400> SEQUENCE: 5

|

```
Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly
465                 470                 475

<210> SEQ ID NO 6
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 6

Gly Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
            85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
            165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
    195                 200                 205

Val Val Trp Asp Arg His Leu Ser Ile Ser Val Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
    275                 280                 285
```

```
Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Ala
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
            370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly
465                 470                 475

<210> SEQ ID NO 7
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 7

Glu Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
            130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175
```

Glu Val Asn Val Lys Arg Pro Met Lys Asp Glu Thr His Phe Glu Val
                180                 185                 190

Val Glu Ser Gly Arg Tyr Ile Ile Leu Leu Gly Lys Ala Leu Ser
            195                 200                 205

Val Val Trp Asp Arg His Leu Ser Ile Ser Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
                275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Ala
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
                370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
                450                 455                 460

Asp Val Val Asn Leu Thr Cys Glu Ala Cys Gln Glu Pro Gly Gly
465                 470                 475

<210> SEQ ID NO 8
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 8

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
50                  55                  60

```
Pro Cys Phe His Gln Gly Lys Glu Tyr Ala Pro Glu Thr Val Lys
 65                  70                  75                  80

Ile Gly Cys Asn Thr Cys Val Cys Arg Asp Arg Lys Trp Asn Cys Thr
                 85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
            195                 200                 205

Val Val Trp Asp Arg His Leu Ser Ile Ser Val Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Ser Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
            290                 295                 300

Phe Gln Asp Cys Asn Lys Leu Val Asp Pro Glu Pro Tyr Leu Asp Ala
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
            370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Glu Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly
465                 470                 475
```

<210> SEQ ID NO 9
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 9

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Gl

```
Glu Arg Asn Leu Arg Glu Asn Gly Tyr Glu Cys Glu Trp Arg Tyr Asn
370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
            405                 410                 415
Gly Lys Ile Leu Asp Glu Leu Leu Gln Thr Cys Val Asp Pro Glu Asp
            420                 425                 430
Cys Pro Val Cys Glu Val Ala Gly Arg Arg Phe Ala Ser Gly Lys Lys
            435                 440                 445
Val Thr Leu Asn Pro Ser Asp Pro Glu His Cys Gln Ile Cys His Cys
450                 455                 460
Asp Val Val Asn Leu Thr Cys Glu Ala Cys Gln Glu Pro Gly Gly
465                 470                 475

<210> SEQ ID NO 10
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 10

Ser Leu Ser Cys Arg Pro Pro Met Val Lys Leu Val Cys Pro Ala Asp
1               5                   10                  15
Asn Leu Arg Ala Glu Gly Leu Glu Cys Thr Lys Thr Cys Gln Asn Tyr
            20                  25                  30
Asp Leu Glu Cys Met Ser Met Gly Cys Val Ser Gly Cys Leu Cys Pro
            35                  40                  45
Pro Gly Met Val Arg His Glu Asn Arg Cys Val Ala Leu Glu Arg Cys
50                  55                  60
Pro Cys Phe His Gln Gly Lys Glu Tyr Ala Pro Gly Glu Thr Val Lys
65                  70                  75                  80
Ile Gly Cys Asn Thr Cys Val Cys Arg Asp Arg Lys Trp Asn Cys Thr
                85                  90                  95
Asp His Val Cys Asp Ala Thr Cys Ser Thr Ile Gly Met Ala His Tyr
            100                 105                 110
Leu Thr Phe Asp Gly Leu Lys Tyr Leu Phe Pro Gly Glu Cys Gln Tyr
            115                 120                 125
Val Leu Val Gln Asp Tyr Cys Gly Ser Asn Pro Gly Thr Phe Arg Ile
130                 135                 140
Leu Val Gly Asn Lys Gly Cys Ser His Pro Ser Val Lys Cys Lys Lys
145                 150                 155                 160
Arg Val Thr Ile Leu Val Glu Gly Gly Glu Ile Glu Leu Phe Asp Gly
                165                 170                 175
Glu Val Asn Val Lys Arg Pro Met Lys Asp Glu Thr His Phe Glu Val
            180                 185                 190
Val Glu Ser Gly Arg Tyr Ile Ile Leu Leu Leu Gly Lys Ala Leu Ser
            195                 200                 205
Val Val Trp Asp Arg His Leu Ser Ile Ser Val Val Leu Lys Gln Thr
210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                245                 250                 255
```

```
Asp Phe Gly Asn Ser Trp Lys Val Ser Ser Gln Cys Ala Asp Thr Arg
                260                 265                 270

Lys Val Pro Leu Asp Ser Thr Pro Ala Thr Cys His Asn Asn Ile Met
            275                 280                 285

Lys Gln Thr Met Val Asp Ser Ser Cys Arg Ile Leu Thr Ser Asp Val
        290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
        450                 455                 460

Asp Val Val Asn Leu Thr Cys Glu Ala Cys Gln Glu Pro Gly Gly
465                 470                 475

<210> SEQ ID NO 11
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 11

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Ala Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140
```

-continued

```
Leu Val Gly Asn Lys Gly Cys Ser His Pro Ser Val Lys Cys Lys Lys
145                 150                 155                 160

Arg Val Thr Ile Leu Val Glu Gly Glu Ile Glu Leu Phe Asp Gly
            165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Gly Lys Ala Leu Ser
            195                 200                 205

Val Val Trp Asp Arg His Leu Ser Ile Ser Val Val Leu Lys Gln Thr
            210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
            370                 375                 380

Ser Cys Ala Pro Ala Cys Gln Val Thr Cys Leu His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
            450                 455                 460

Asp Val Val Asn Leu Thr Cys Glu Ala Cys Gln Glu Pro Gly Gly
465                 470                 475
```

<210> SEQ ID NO 12
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE

-continued

```
Asp Leu Glu Cys Met Ser Met Gly Cys Val Ser Gly Cys Leu Cys Pro
             35                  40                  45

Pro Gly Met Val Arg His Glu Asn Arg Cys Val Ala Leu Glu Arg Cys
 50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Arg Asp Arg Lys Trp Asn Cys Thr
                 85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
130                 135                 140

Leu Val Gly Asn Glu Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
            195                 200                 205

Val Val Trp Asp Arg His Leu Ser Ile Ser Val Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Ser Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
```

```
            450                 455                 460
Asp Val Val Asn Leu Thr Cys Glu Ala Cys Gln Glu Pro Gly Gly
465                 470                 475

<210> SEQ ID NO 13
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 13

Ser Leu Ser Cys Arg Pro Pro Met Val Lys Leu Val Cys Pro Ala Asp
1               5                   10                  15

Asn Pro Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
```

```
            340                 345                 350
Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
        370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
        405                 410                 415

Gly Lys Ile Leu Asp Glu Leu Leu Gln Thr Cys Val Asp Pro Glu Asp
        420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
        450                 455                 460

Asp Val Val Asn Leu Thr Cys Glu Ala Cys Gln Glu Pro Gly Gly
465                 470                 475

<210> SEQ ID NO 14
<211> LENGTH: 2332
<212> TYPE: PRT
<213> ORGANISM: Homo sapiens

<400> SEQUENCE: 14

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240
```

-continued

```
Ser Leu Pro Gly Leu Ile Gly Cys His Arg Lys Ser Val Tyr Trp His
            245                 250                 255
Val Ile Gly Met Gly Thr Thr Pro Glu Val His Ser Ile Phe Leu Glu
        260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
Ile Gln Ile Arg Ser Val Ala Lys Lys His Pro Lys Thr Trp Val His
    370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
```

-continued

```
              660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
            690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Arg Ser Thr Arg
                740                 745                 750
Gln Lys Gln Phe Asn Ala Thr Thr Ile Pro Glu Asn Asp Ile Glu Lys
            755                 760                 765
Thr Asp Pro Trp Phe Ala His Arg Thr Pro Met Pro Lys Ile Gln Asn
            770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
                820                 825                 830
Glu Met Thr His Phe Arg Pro Gln Leu His His Ser Gly Asp Met Val
            835                 840                 845
Phe Thr Pro Glu Ser Gly Leu Gln Leu Arg Leu Asn Glu Lys Leu Gly
            850                 855                 860
Thr Thr Ala Ala Thr Glu Leu Lys Lys Leu Asp Phe Lys Val Ser Ser
865                 870                 875                 880
Thr Ser Asn Asn Leu Ile Ser Thr Ile Pro Ser Asp Asn Leu Ala Ala
                885                 890                 895
Gly Thr Asp Asn Thr Ser Ser Leu Gly Pro Pro Ser Met Pro Val His
                900                 905                 910
Tyr Asp Ser Gln Leu Asp Thr Thr Leu Phe Gly Lys Lys Ser Ser Pro
            915                 920                 925
Leu Thr Glu Ser Gly Gly Pro Leu Ser Leu Ser Glu Glu Asn Asn Asp
            930                 935                 940
Ser Lys Leu Leu Glu Ser Gly Leu Met Asn Ser Gln Glu Ser Ser Trp
945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
                980                 985                 990
Val Ser Ile Ser Leu Leu Lys Thr Asn Lys Thr Ser Asn  Asn Ser Ala
            995                1000                1005
Thr Asn Arg Lys Thr His Ile Asp Gly Pro Ser Leu Leu Ile Glu
            1010                1015                1020
Asn Ser Pro Ser Val Trp Gln Asn Ile Leu Glu Ser Asp Thr Glu
            1025                1030                1035
Phe Lys Lys Val Thr Pro Leu Ile His Asp Arg Met Leu Met Asp
            1040                1045                1050
Lys Asn Ala Thr Ala Leu Arg Leu Asn His Met Ser Asn Lys Thr
            1055                1060                1065
Thr Ser Ser Lys Asn Met Glu Met Val Gln Gln Lys Lys Glu Gly
            1070                1075                1080
```

```
Pro Ile Pro Pro Asp Ala Gln Asn Pro Asp Met Ser Phe Phe Lys
    1085            1090                1095

Met Leu Phe Leu Pro Glu Ser Ala Arg Trp Ile Gln Arg Thr His
    1100            1105                1110

Gly Lys Asn Ser Leu Asn Ser Gly Gln Gly Pro Ser Pro Lys Gln
    1115            1120                1125

Leu Val Ser Leu Gly Pro Glu Lys Ser Val Glu Gly Gln Asn Phe
    1130            1135                1140

Leu Ser Glu Lys Asn Lys Val Val Val Gly Lys Gly Glu Phe Thr
    1145            1150                1155

Lys Asp Val Gly Leu Lys Glu Met Val Phe Pro Ser Ser Arg Asn
    1160            1165                1170

Leu Phe Leu Thr Asn Leu Asp Asn Leu His Glu Asn Asn Thr His
    1175            1180                1185

Asn Gln Glu Lys Lys Ile Gln Glu Glu Ile Glu Lys Lys Glu Thr
    1190            1195                1200

Leu Ile Gln Glu Asn Val Val Leu Pro Gln Ile His Thr Val Thr
    1205            1210                1215

Gly Thr Lys Asn Phe Met Lys Asn Leu Phe Leu Leu Ser Thr Arg
    1220            1225                1230

Gln Asn Val Glu Gly Ser Tyr Asp Gly Ala Tyr Ala Pro Val Leu
    1235            1240                1245

Gln Asp Phe Arg Ser Leu Asn Asp Ser Thr Asn Arg Thr Lys Lys
    1250            1255                1260

His Thr Ala His Phe Ser Lys Lys Gly Glu Glu Glu Asn Leu Glu
    1265            1270                1275

Gly Leu Gly Asn Gln Thr Lys Gln Ile Val Glu Lys Tyr Ala Cys
    1280            1285                1290

Thr Thr Arg Ile Ser Pro Asn Thr Ser Gln Gln Asn Phe Val Thr
    1295            1300                1305

Gln Arg Ser Lys Arg Ala Leu Lys Gln Phe Arg Leu Pro Leu Glu
    1310            1315                1320

Glu Thr Glu Leu Glu Lys Arg Ile Ile Val Asp Asp Thr Ser Thr
    1325            1330                1335

Gln Trp Ser Lys Asn Met Lys His Leu Thr Pro Ser Thr Leu Thr
    1340            1345                1350

Gln Ile Asp Tyr Asn Glu Lys Glu Lys Gly Ala Ile Thr Gln Ser
    1355            1360                1365

Pro Leu Ser Asp Cys Leu Thr Arg Ser His Ser Ile Pro Gln Ala
    1370            1375                1380

Asn Arg Ser Pro Leu Pro Ile Ala Lys Val Ser Ser Phe Pro Ser
    1385            1390                1395

Ile Arg Pro Ile Tyr Leu Thr Arg Val Leu Phe Gln Asp Asn Ser
    1400            1405                1410

Ser His Leu Pro Ala Ala Ser Tyr Arg Lys Lys Asp Ser Gly Val
    1415            1420                1425

Gln Glu Ser Ser His Phe Leu Gln Gly Ala Lys Lys Asn Asn Leu
    1430            1435                1440

Ser Leu Ala Ile Leu Thr Leu Glu Met Thr Gly Asp Gln Arg Glu
    1445            1450                1455

Val Gly Ser Leu Gly Thr Ser Ala Thr Asn Ser Val Thr Tyr Lys
    1460            1465                1470
```

```
Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
```

-continued

```
               1865                1870                1875
Phe  Phe  Thr  Ile  Phe  Asp  Glu  Thr  Lys  Ser  Trp  Tyr  Phe  Thr  Glu
     1880                1885                1890

Asn  Met  Glu  Arg  Asn  Cys  Arg  Ala  Pro  Cys  Asn  Ile  Gln  Met  Glu
     1895                1900                1905

Asp  Pro  Thr  Phe  Lys  Glu  Asn  Tyr  Arg  Phe  His  Ala  Ile  Asn  Gly
     1910                1915                1920

Tyr  Ile  Met  Asp  Thr  Leu  Pro  Gly  Leu  Val  Met  Ala  Gln  Asp  Gln
     1925                1930                1935

Arg  Ile  Arg  Trp  Tyr  Leu  Leu  Ser  Met  Gly  Ser  Asn  Glu  Asn  Ile
     1940                1945                1950

His  Ser  Ile  His  Phe  Ser  Gly  His  Val  Phe  Thr  Val  Arg  Lys  Lys
     1955                1960                1965

Glu  Glu  Tyr  Lys  Met  Ala  Leu  Tyr  Asn  Leu  Tyr  Pro  Gly  Val  Phe
     1970                1975                1980

Glu  Thr  Val  Glu  Met  Leu  Pro  Ser  Lys  Ala  Gly  Ile  Trp  Arg  Val
     1985                1990                1995

Glu  Cys  Leu  Ile  Gly  Glu  His  Leu  His  Ala  Gly  Met  Ser  Thr  Leu
     2000                2005                2010

Phe  Leu  Val  Tyr  Ser  Asn  Lys  Cys  Gln  Thr  Pro  Leu  Gly  Met  Ala
     2015                2020                2025

Ser  Gly  His  Ile  Arg  Asp  Phe  Gln  Ile  Thr  Ala  Ser  Gly  Gln  Tyr
     2030                2035                2040

Gly  Gln  Trp  Ala  Pro  Lys  Leu  Ala  Arg  Leu  His  Tyr  Ser  Gly  Ser
     2045                2050                2055

Ile  Asn  Ala  Trp  Ser  Thr  Lys  Glu  Pro  Phe  Ser  Trp  Ile  Lys  Val
     2060                2065                2070

Asp  Leu  Leu  Ala  Pro  Met  Ile  Ile  His  Gly  Ile  Lys  Thr  Gln  Gly
     2075                2080                2085

Ala  Arg  Gln  Lys  Phe  Ser  Ser  Leu  Tyr  Ile  Ser  Gln  Phe  Ile  Ile
     2090                2095                2100

Met  Tyr  Ser  Leu  Asp  Gly  Lys  Lys  Trp  Gln  Thr  Tyr  Arg  Gly  Asn
     2105                2110                2115

Ser  Thr  Gly  Thr  Leu  Met  Val  Phe  Phe  Gly  Asn  Val  Asp  Ser  Ser
     2120                2125                2130

Gly  Ile  Lys  His  Asn  Ile  Phe  Asn  Pro  Pro  Ile  Ile  Ala  Arg  Tyr
     2135                2140                2145

Ile  Arg  Leu  His  Pro  Thr  His  Tyr  Ser  Ile  Arg  Ser  Thr  Leu  Arg
     2150                2155                2160

Met  Glu  Leu  Met  Gly  Cys  Asp  Leu  Asn  Ser  Cys  Ser  Met  Pro  Leu
     2165                2170                2175

Gly  Met  Glu  Ser  Lys  Ala  Ile  Ser  Asp  Ala  Gln  Ile  Thr  Ala  Ser
     2180                2185                2190

Ser  Tyr  Phe  Thr  Asn  Met  Phe  Ala  Thr  Trp  Ser  Pro  Ser  Lys  Ala
     2195                2200                2205

Arg  Leu  His  Leu  Gln  Gly  Arg  Ser  Asn  Ala  Trp  Arg  Pro  Gln  Val
     2210                2215                2220

Asn  Asn  Pro  Lys  Glu  Trp  Leu  Gln  Val  Asp  Phe  Gln  Lys  Thr  Met
     2225                2230                2235

Lys  Val  Thr  Gly  Val  Thr  Thr  Gln  Gly  Val  Lys  Ser  Leu  Leu  Thr
     2240                2245                2250

Ser  Met  Tyr  Val  Lys  Glu  Phe  Leu  Ile  Ser  Ser  Ser  Gln  Asp  Gly
     2255                2260                2265
```

```
His Gln Trp Thr Leu Phe Phe Gln Asn Gly Lys Val Lys Val Phe
    2270            2275                2280

Gln Gly Asn Gln Asp Ser Phe Thr Pro Val Val Asn Ser Leu Asp
    2285            2290                2295

Pro Pro Leu Leu Thr Arg Tyr Leu Arg Ile His Pro Gln Ser Trp
    2300            2305                2310

Val His Gln Ile Ala Leu Arg Met Glu Val Leu Gly Cys Glu Ala
    2315            2320                2325

Gln Asp Leu Tyr
    2330

<210> SEQ ID NO 15
<211> LENGTH: 1444
<212> TYPE: PRT
<213> ORGANISM: Artificial sequence
<220> FEATURE:
<223> OTHER INFORMATION: mature single chain Factor VIII

<400> SEQUENCE: 15

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285
```

```
Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
    515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
    595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
    675                 680                 685

Ile Leu Gly Cys His Asn Ser Asp Phe Arg Asn Arg Gly Met Thr Ala
    690                 695                 700
```

```
Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Ser Arg His Arg Ser Thr Arg
            740                 745                 750

Gln Lys Gln Phe Asn Ala Thr Thr Ile Pro Glu Asn Thr Thr Leu Gln
        755                 760                 765

Ser Asp Gln Glu Glu Ile Asp Tyr Asp Asp Thr Ile Ser Val Glu Met
770                 775                 780

Lys Lys Glu Asp Phe Asp Ile Tyr Asp Glu Asp Glu Asn Gln Ser Pro
785                 790                 795                 800

Arg Ser Phe Gln Lys Lys Thr Arg His Tyr Phe Ile Ala Ala Val Glu
            805                 810                 815

Arg Leu Trp Asp Tyr Gly Met Ser Ser Ser Pro His Val Leu Arg Asn
            820                 825                 830

Arg Ala Gln Ser Gly Ser Val Pro Gln Phe Lys Lys Val Val Phe Gln
            835                 840                 845

Glu Phe Thr Asp Gly Ser Phe Thr Gln Pro Leu Tyr Arg Gly Glu Leu
        850                 855                 860

Asn Glu His Leu Gly Leu Leu Gly Pro Tyr Ile Arg Ala Glu Val Glu
865                 870                 875                 880

Asp Asn Ile Met Val Thr Phe Arg Asn Gln Ala Ser Arg Pro Tyr Ser
                885                 890                 895

Phe Tyr Ser Ser Leu Ile Ser Tyr Glu Glu Asp Gln Arg Gln Gly Ala
            900                 905                 910

Glu Pro Arg Lys Asn Phe Val Lys Pro Asn Glu Thr Lys Thr Tyr Phe
            915                 920                 925

Trp Lys Val Gln His His Met Ala Pro Thr Lys Asp Glu Phe Asp Cys
        930                 935                 940

Lys Ala Trp Ala Tyr Phe Ser Asp Val Asp Leu Glu Lys Asp Val His
945                 950                 955                 960

Ser Gly Leu Ile Gly Pro Leu Leu Val Cys His Thr Asn Thr Leu Asn
                965                 970                 975

Pro Ala His Gly Arg Gln Val Thr Val Gln Glu Phe Ala Leu Phe Phe
            980                 985                 990

Thr Ile Phe Asp Glu Thr Lys Ser Trp Tyr Phe Thr Glu Asn Met Glu
        995                 1000                1005

Arg Asn Cys Arg Ala Pro Cys Asn Ile Gln Met Glu Asp Pro Thr
    1010                1015                1020

Phe Lys Glu Asn Tyr Arg Phe His Ala Ile Asn Gly Tyr Ile Met
    1025                1030                1035

Asp Thr Leu Pro Gly Leu Val Met Ala Gln Asp Gln Arg Ile Arg
    1040                1045                1050

Trp Tyr Leu Leu Ser Met Gly Ser Asn Glu Asn Ile His Ser Ile
    1055                1060                1065

His Phe Ser Gly His Val Phe Thr Val Arg Lys Lys Glu Glu Tyr
    1070                1075                1080

Lys Met Ala Leu Tyr Asn Leu Tyr Pro Gly Val Phe Glu Thr Val
    1085                1090                1095

Glu Met Leu Pro Ser Lys Ala Gly Ile Trp Arg Val Glu Cys Leu
    1100                1105                1110

Ile Gly Glu His Leu His Ala Gly Met Ser Thr Leu Phe Leu Val
```

```
                    1115                1120                1125

Tyr Ser Asn Lys Cys Gln Thr Pro Leu Gly Met Ala Ser Gly His
            1130                1135                1140

Ile Arg Asp Phe Gln Ile Thr Ala Ser Gly Tyr Gly Gln Trp
            1145                1150                1155

Ala Pro Lys Leu Ala Arg Leu His Tyr Ser Gly Ser Ile Asn Ala
            1160                1165                1170

Trp Ser Thr Lys Glu Pro Phe Ser Trp Ile Lys Val Asp Leu Leu
            1175                1180                1185

Ala Pro Met Ile Ile His Gly Ile Lys Thr Gln Gly Ala Arg Gln
            1190                1195                1200

Lys Phe Ser Ser Leu Tyr Ile Ser Gln Phe Ile Ile Met Tyr Ser
            1205                1210                1215

Leu Asp Gly Lys Lys Trp Gln Thr Tyr Arg Gly Asn Ser Thr Gly
            1220                1225                1230

Thr Leu Met Val Phe Phe Gly Asn Val Asp Ser Ser Gly Ile Lys
            1235                1240                1245

His Asn Ile Phe Asn Pro Pro Ile Ile Ala Arg Tyr Ile Arg Leu
            1250                1255                1260

His Pro Thr His Tyr Ser Ile Arg Ser Thr Leu Arg Met Glu Leu
            1265                1270                1275

Met Gly Cys Asp Leu Asn Ser Cys Ser Met Pro Leu Gly Met Glu
            1280                1285                1290

Ser Lys Ala Ile Ser Asp Ala Gln Ile Thr Ala Ser Ser Tyr Phe
            1295                1300                1305

Thr Asn Met Phe Ala Thr Trp Ser Pro Ser Lys Ala Arg Leu His
            1310                1315                1320

Leu Gln Gly Arg Ser Asn Ala Trp Arg Pro Gln Val Asn Asn Pro
            1325                1330                1335

Lys Glu Trp Leu Gln Val Asp Phe Gln Lys Thr Met Lys Val Thr
            1340                1345                1350

Gly Val Thr Thr Gln Gly Val Lys Ser Leu Leu Thr Ser Met Tyr
            1355                1360                1365

Val Lys Glu Phe Leu Ile Ser Ser Ser Gln Asp Gly His Gln Trp
            1370                1375                1380

Thr Leu Phe Phe Gln Asn Gly Lys Val Lys Val Phe Gln Gly Asn
            1385                1390                1395

Gln Asp Ser Phe Thr Pro Val Val Asn Ser Leu Asp Pro Pro Leu
            1400                1405                1410

Leu Thr Arg Tyr Leu Arg Ile His Pro Gln Ser Trp Val His Gln
            1415                1420                1425

Ile Ala Leu Arg Met Glu Val Leu Gly Cys Glu Ala Gln Asp Leu
            1430                1435                1440

Tyr

<210> SEQ ID NO 16
<211> LENGTH: 585
<212> TYPE: PRT
<213> ORGANISM: Homo sapiens

<400> SEQUENCE: 16

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
```

-continued

```
                20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
        50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
```

```
Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 17
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 17

Ser Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220
```

```
Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Ala
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly
465                 470                 475

<210> SEQ ID NO 18
<211> LENGTH: 479
<212> TYPE: PRT
<213> ORGANISM: Artificial sequence
<220> FEATURE:
<223> OTHER INFORMATION: Modified D'-D3 domain of VWFPRT

<400>

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
        130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Gly Lys Ala Leu Ser
        195                 200                 205

Val Val Trp Asp Arg His Leu Ser Ile Ser Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
        260                 265                 270

Lys Val Pro Leu Asp Ser Ser Pro Ala Thr Cys His Asn Asn Ile Met
    275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
        420                 425                 430

Cys Pro Val Cys Glu Val Ala Gly Arg Arg Phe Ala Ser Gly Lys Lys
    435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly
465                 470                 475

<210> SEQ ID NO 19
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 19

-continued

```
Pro Leu Ile Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
            130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
                180                 185                 190

Val Glu Ser Gly Arg Tyr Ile Ile Leu Leu Gly Lys Ala Leu Ser
            195                 200                 205

Val Val Trp Asp Arg His Leu Ser Ile Ser Val Leu Lys Gln Thr
            210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Asp Pro Val
            245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
            290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415
```

```
Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly
465                 470                 475

<210> SEQ ID NO 20
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 20

Pro Leu Met Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300
```

```
Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly
465                 470                 475

<210> SEQ ID NO 21
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 21

Val Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
    115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190
```

```
Val Glu Ser Gly Arg Tyr Ile Ile Leu Leu Gly Lys Ala Leu Ser
            195                 200                 205

Val Val Trp Asp Arg His Leu Ser Ile Ser Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly
465                 470                 475

<210> SEQ ID NO 22
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 22

Glu Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80
```

Ile Gly Cys Asn Thr Cys Val Cys Arg Asp Arg Lys Trp Asn Cys Thr
            85                  90                  95

Asp His Val Cys Asp Ala Thr Cys Ser Thr Ile Gly Met Ala His Tyr
        100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
        130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
            165                 170                 175

Glu Val Asn Val Lys Arg Pro Met Lys Asp Glu Thr His Phe Glu Val
        180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
        210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
            325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
            370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
        450                 455                 460

Asp Val Val Asn Leu Thr Cys Glu Ala Cys Gln Glu Pro Gly Gly
465                 470                 475

<210> SEQ ID NO 23
<211> LENGTH: 479
<212> TYPE: PRT

<210> ORGANISM: Artificial sequence
<220> FEATURE:
<223> OTHER INFORMATION: Modified D'-D3 domain of VWFPRT

<400> SEQUENCE: 23

```
Tyr Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
```

```
                385                 390                 395                 400
Ala Cys Pro Val Gln Cys Val Glu Gly Cys His Ala His Cys Pro Pro
                    405                 410                 415
Gly Lys Ile Leu Asp Glu Leu Leu Gln Thr Cys Val Asp Pro Glu Asp
                420                 425                 430
Cys Pro Val Cys Glu Val Ala Gly Arg Arg Phe Ala Ser Gly Lys Lys
                435                 440                 445
Val Thr Leu Asn Pro Ser Asp Pro Glu His Cys Gln Ile Cys His Cys
    450                 455                 460
Asp Val Val Asn Leu Thr Cys Glu Ala Cys Gln Glu Pro Gly Gly
465                 470                 475

<210> SEQ ID NO 24
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 24

Leu Leu Tyr Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
```

```
            275                 280                 285
Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly
465                 470                 475

<210> SEQ ID NO 25
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 25

Pro Leu Trp Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
```

```
            165                 170                 175
Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
            195                 200                 205

Val Val Trp Asp Arg His Leu Ser Ile Ser Val Val Leu Lys Gln Thr
            210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
                275                 280                 285

Lys Gln Thr Met Val Asp Ser Ser Cys Arg Ile Leu Thr Ser Asp Val
                290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
                370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
                450                 455                 460

Asp Val Val Asn Leu Thr Cys Glu Ala Cys Gln Glu Pro Gly Gly
465                 470                 475

<210> SEQ ID NO 26
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 26

Ser Leu Trp Cys Arg Pro Pro Met Val Lys Leu Val Cys Pro Ala Asp
1               5                   10                  15

Asn Leu Arg Ala Glu Gly Leu Glu Cys Thr Lys Thr Cys G

```
            50                  55                  60
Pro Cys Phe His Gln Gly Lys Glu Tyr Ala Pro Gly Glu Thr Val Lys
 65                  70                  75                  80

Ile Gly Cys Asn Thr Cys Val Cys Arg Asp Arg Lys Trp Asn Cys Thr
                 85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
                115                 120                 125

Val Leu Val Gln Asp Tyr Cys Gly Ser Asn Pro Gly Thr Phe Arg Ile
130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
                180                 185                 190

Val Glu Ser Gly Arg Tyr Ile Ile Leu Leu Leu Gly Lys Ala Leu Ser
                195                 200                 205

Val Val Trp Asp Arg His Leu Ser Ile Ser Val Val Leu Lys Gln Thr
                210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
                275                 280                 285

Lys Gln Thr Met Val Asp Ser Ser Cys Arg Ile Leu Thr Ser Asp Val
                290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
                370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
                450                 455                 460

Asp Val Val Asn Leu Thr Cys Glu Ala Cys Gln Glu Pro Gly Gly
465                 470                 475
```

<210> SEQ ID NO 27
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 27

```
Ser Leu Tyr Cys Arg Lys Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365
```

```
Glu Arg Asn Leu Arg Glu Asn Gly Tyr Glu Cys Glu Trp Arg Tyr Asn
            370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
            450                 455                 460

Asp Val Val Asn Leu Thr Cys Glu Ala Cys Gln Glu Pro Gly Gly
465                 470                 475

<210> SEQ ID NO 28
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 28

Ser Leu Tyr Cys Arg Asn Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255
```

-continued

```
Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly
465                 470                 475

<210> SEQ ID NO 29
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 29

Ser Leu Tyr Cys Arg Arg Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140
```

```
Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly
465                 470                 475

<210> SEQ ID NO 30
<211> LENGTH: 479
<212> TYPE: PRT
<213> ORGANISM: Artificial sequence
<220> FEATURE:
<223> OTHER INFORMATION: Modified D'-D3 domain of VWFPRT

<400> SEQUENCE: 30

Pro Leu Leu Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30
```

-continued

```
Asp Leu Glu Cys Met Ser Met Gly Cys Val Ser Gly Cys Leu Cys Pro
         35                  40                  45

Pro Gly Met Val Arg His Glu Asn Arg Cys Val Ala Leu Glu Arg Cys
 50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Arg Asp Arg Lys Trp Asn Cys Thr
                 85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
130                 135                 140

Leu Val Gly Asn Lys Gly Cys Ser His Pro Ser Val Lys Cys Lys Lys
145                 150                 155                 160

Arg Val Thr Ile Leu Val Glu Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
            195                 200                 205

Val Val Trp Asp Arg His Leu Ser Ile Ser Val Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445
```

```
Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly
465                 470                 475

<210> SEQ ID NO 31
<211> LENGTH: 1221
<212> TYPE: DNA
<213> ORGANISM: Homo sapiens

<400> SEQUENCE: 31
atgattcaca ccaacctgaa gaaaaagttc agctgctgcg tcctggtctt tcttctgttt        60
gcagtcatct gtgtgtggaa ggaaaagaag aaagggagtt actatgattc ctttaaattg       120
caaaccaagg aattccaggt gttaaagagt ctggggaaat tggccatggg gtctgattcc       180
cagtctgtat cctcaagcag cacccaggac ccccacaggg gccgccagac cctcggcagt       240
ctcagaggcc tagccaaggc caaccagagc gcctccttcc aggtgtggaa caaggacagc       300
tcttccaaaa accttatccc taggctgcaa aagatctgga agaattacct aagcatgaac       360
aagtacaaag tgtcctacaa ggggccagga ccaggcatca agttcagtgc agaggccctg       420
cgctgccacc tccgggacca tgtgaatgta tccatggtag aggtcacaga ttttcccttc       480
aatacctctg aatgggaggg ttatctgccc aaggagagca ttaggaccaa ggctgggcct       540
tggggcaggt gtgctgttgt gtcgtcagcg ggatctctga agtcctccca actaggcaga       600
gaaatcgatg atcatgacgc agtcctgagg tttaatgggg cacccacagc caacttccaa       660
caagatgtgg gcacaaaaac taccattcgc ctgatgaact ctcagttggt taccacagag       720
aagcgcttcc tcaaagacag tttgtacaat gaaggaatcc taattgtatg ggaccatct        780 gtataccact cagatatccc aaagtggtac cagaatccgg attataattt ctttaacaac       840
tacaagactt atcgtaagct gcaccccaat cagccctttt acatcctcaa gccccagatg       900
ccttgggagc tatgggacat tcttcaagaa atctccccag aagagattca gccaaacccc       960
ccatcctctg ggatgcttgg tatcatcatc atgatgacgc tgtgtgacca ggtggatatt      1020
tatgagttcc tcccatccaa gcgcaagact gacgtgtgct actactacca gaagttcttc      1080
gatagtgcct gcacgatggg tgcctaccac ccgctgctct atgagaagaa tttggtgaag      1140
catctcaacc agggcacaga tgaggacatc tacctgcttg aaaagccac actgcctggc       1200 ttccggacca ttcactgcta a                                                1221

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Tyr Lys Asp Asp Asp Asp Lys
1               5
```